United States Patent
Bouix-Peter et al.

(10) Patent No.: US 8,877,968 B2
(45) Date of Patent: Nov. 4, 2014

(54) MELANOCORTIN RECEPTOR MODULATORS, PROCESS FOR PREPARING THEM AND USE THERE IN HUMAN MEDICINE AND COSMETICS

(75) Inventors: Claire Bouix-Peter, Vallauris (FR); Itaru Suzuki, Fayence (FR); Isabelle Pelisson, Vallauris (FR); Pascal Collette, Le Cannet (FR); Samuel Tabet, Valbonne (FR); Guillaume Lafitte, Antibes (FR)

(73) Assignee: Galderma Research & Development, Biot (FR)

( * ) Notice: Subject to any disclaimer, the term of this patent is extended or adjusted under 35 U.S.C. 154(b) by 325 days.

(21) Appl. No.: 13/126,542

(22) PCT Filed: Nov. 4, 2009

(86) PCT No.: PCT/EP2009/064648
§ 371 (c)(1),
(2), (4) Date: Jul. 28, 2011

(87) PCT Pub. No.: WO2010/052255
PCT Pub. Date: May 14, 2010

(65) Prior Publication Data
US 2011/0275657 A1 Nov. 10, 2011

Related U.S. Application Data

(60) Provisional application No. 61/111,169, filed on Nov. 4, 2008.

(30) Foreign Application Priority Data

Nov. 4, 2008 (FR) ...................................... 08 57498

(51) Int. Cl.
| | |
|---|---|
| *C07C 273/00* | (2006.01) |
| *C07C 275/00* | (2006.01) |
| *A01N 43/40* | (2006.01) |
| *A61K 31/445* | (2006.01) |
| *A01N 47/28* | (2006.01) |
| *A61K 31/17* | (2006.01) |
| *C07D 401/12* | (2006.01) |
| *C07D 403/12* | (2006.01) |

(52) U.S. Cl.
CPC ............ *C07D 401/12* (2013.01); *C07D 403/12* (2013.01)
USPC ................ 564/57; 564/58; 514/315; 514/588

(58) Field of Classification Search
None
See application file for complete search history.

(56) References Cited

U.S. PATENT DOCUMENTS

2004/0006067 A1   1/2004   Fotsch et al.

FOREIGN PATENT DOCUMENTS

| EP | 1072591 A1 | 1/2001 |
| WO | 02/070511 A1 | 9/2002 |
| WO | 2005/047251 A1 | 5/2005 |
| WO | 2005/047253 A1 | 5/2005 |

OTHER PUBLICATIONS

Todorovic et al. "A review of melanocortin receptor small molecule ligands", Peptides, 2005, vol. 26, Issue 10, pp. 2026-2036.*
Langan et al. "Melanotropic peptides: more than just 'Barbie drugs' and 'sun-tan jabs'?" Br.J.Dermatol., 2010, vol. 163, No. 3, pp. 451-455.*
International Search Report issued on Jan. 22, 2010, by the European Patent Office as the International Searching Authority in International Patent Application No. PCT/EP2009/064648.
International Preliminary Report on Patentability (PCT/IB/373) and Written Opinion of the International Searching Authority (PCT/ISA/237) issued on May 10, 2011, in International Patent Application No. PCT/EP2009/064648.
Mogil et al., "Melanocortin-1 receptor gene variants affect pain and μ-opioid analgesia in mice and humans", J. Med. Genet 2005; 42: 583-587.
Valverde et al., "Variants of the melanocyte-stimulating hormone receptor gene are associated with red hair and fair skin in humans", Nature Genetics, vol. 11, Nov. 1995, 328-330.
Herpin et al., "Discovery of Tyrosine-Based Potent and Selective Melanocortin-1 Receptor Small-Molecule Agonists with Anti-Inflammatory Properties", J. Med. Chem., 2003, 46, 1123-1126.

* cited by examiner

*Primary Examiner* — James D Anderson
*Assistant Examiner* — Stephanie Springer
(74) *Attorney, Agent, or Firm* — Dentons US LLP

(57) ABSTRACT

Melanocortin receptor modulators, processes for preparing them and use thereof in human medicine and cosmetics are described. Melanocortin receptor modulators corresponding to formula (I):

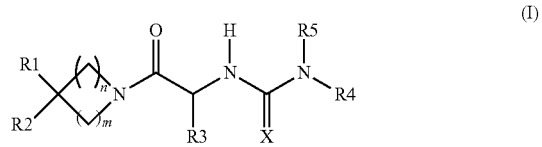

compositions containing them, processes for their preparation and their use in pharmaceutical or cosmetic compositions are also described.

36 Claims, 2 Drawing Sheets

MELANOCORTIN RECEPTOR MODULATORS, PROCESS FOR PREPARING THEM AND USE THERE IN HUMAN MEDICINE AND COSMETICS

This application the United States national phase of PCT/EP2009/064648, filed Nov. 4, 2009, and designating the United States (published in the English language on May 14, 2010, as WO 2010/052255 A1; the title and abstract were also published in English), which claims benefit of U.S. Provisional Application No. 61/111,169, filed Nov. 4, 2008, and also claims priority under 35 U.S.C. §119 of FR 0857498, filed Nov. 4, 2008, each earlier application hereby expressly incorporated by reference in its entirety and each assigned to the assignee hereof.

The invention relates to novel compounds as products modulating one or more melanocortin receptors. The invention also relates to a process for preparing them and to their therapeutic use.

Melanocortins form the family of regulatory peptides that are synthesized via a post-translational process of the hormone propiomelanocortin (POMC—131 amino acids long). POMC leads to the production of three classes of hormone: melanocortins, the hormone adrenocorticotropin and various endorphins, for instance lignotropin (Cone, et al., Recent Prog. Horm. Res., 51: 287-317, (1996); Cone et al., Ann. N.Y. Acad. Sc., 31: 342-363, (1993).

Melanocortin receptors (MCRs) form part of the superfamily of GPCRs with seven transmembrane domains. To date, five subtypes of receptor, MC1-5R, have been identified in mammals. An endogenous group of peptides binds to MCRs with agonist or antagonist effects, for instance the melanocyte-stimulating hormones (MSH), adrenocorticotropic hormone (ACTH), and the Agouti proteins and derivatives thereof. However, an exception is the MC2R receptor, which binds only with ACTH (Major pharmacological distinction of the ACTH receptor from other melanocortin receptors, Schioth et al., Life Sciences (1996), 59(10), 797-801).

MCRs have varied physiological roles. MC1R regulates the formation of melanin in the skin, and has a role in regulating the immune system. MC2R regulates the production of corticosteroids in the adrenal glands. The receptors MC3R and MC4R play a role in controlling food intake and sexual behaviour. MC5R is involved in regulating the exocrine glands (Wikberg, Jarl E. S., Melanocortin receptors: perspectives for novel drugs. European Journal of Pharmacology (1999), 375(1-3), 295-310. Wikberg, Jarl E. S., Melanocortin receptors: new opportunities in drug discovery. Expert Opinion on Therapeutic Patents (2001), 11(1), 61-76).

The potential use of MCRs as targets for medicaments for treating major pathologies such as obesity, diabetes, inflammatory conditions and sexual dysfunction raises the need for compounds that show high specificity towards a particular subtype. However, the modelling of selective medicaments, for slightly different receptor subtypes, is a difficult task that would be simplified in the light of detailed knowledge regarding the determinants of the ligand-receptor interaction.

The Applicant has now discovered, surprisingly and unexpectedly, that novel compounds of general formula (I) as defined hereinbelow show very good activity on the melanocortin receptors, and in particular certain compounds are active on MC1-R and have physicochemical properties suited to topical administration.

It has especially been demonstrated that MC1-R is one of the key proteins in regulating melanin synthesis in the melanocytes.

MC1-R is expressed in the melanocytes and is involved in skin pigmentation, the coloration of animal fur and the functions of the melanocyte. Melanocortins may thus be used for treating hypopigmentation and hyperpigmentation disorders. Polymorphism data for the MC1-R gene have been associated with the ginger hair phenotype and with malignant and non-malignant skin cancers (Xu X. et al., Nat. Genet. 1996; 14: 384; Van Der Velden P. A. et al., Am. J. Hum. Genet. 2001; 69; 774-779; Valverde P. et al., Hum. Mol. Genet. 1996; 5; 1663-1666; Schioth H. B., Biochem. Biophys. Res. Commun. 1999; 260: 488-491; Scott M. G. et al., J. Cell Sci. 2002; 115; 2349-2355). Thus, a connection exists between MC1-R and melanoma, and as a result MC1-R may be important in preventing and treating certain forms of skin cancer (Stockfleth E. et al., Recent Results in Cancer Res. 2002; 160; 259-268; Stander et al., Exp. Dermatol. 2002; 11:42-51). MC1-R is also expressed in macrophages and monocytes (Star et al., Proc. Natl. Acad. Sci. USA 92; 8016-8020; Hartmeyer et al., J. Immunol. 159; 1930-1937), neutrophils (Catania et al., Peptides 17; 675-679), endothelial cells (Hartmeyer et al., J. Immunol. 159; 1930-1937), gliomal cells and astrocytes (Wong et al., Neuroimmunomodulation 4, 37-41), fibroblasts (Boston and Cone, Endocrinology 137, 2043-2050) and keratinocytes (Luger et al., J. Invest. Dermatol. Symp. Proc. 2, 87-93). Localization of MC1-R in these cells is associated with the capacity of MSH-based peptides to inhibit inflammatory processes. Specifically, α-MSH has shown strong inhibition of inflammation in chronic models of intestinal inflammation, arthritis, ischaemia, contact hypersensitivity and dermatitis, and is also capable of inducing tolerance to haptenes (Ceriana et al., Neuroimmunomodulation, 1, 28-32; Chiao et al., Clin. Invest. 99, 1165-1172; Huh and Lipton, Neurosurgery, 40, 132-139; Luger et al J. Invest. Dermatol. Symp. Proc. 2, 87-93; Rajora et al., Peptides 18, 381-385; J. Neurosci. 17, 2181-2196; Lipton et al., Neuroimmunomodulation, 5, 178-183). Melanocortins may thus be used for treating inflammatory disorders and immune disorders. It has been suggested that the MC1-R signalling pathway plays a role in the perception of pain and that functional variations of MC1-R are linked to a high tolerance to pain (Mogil et al., J. Med. Genet. 2005 July; 42(7): 583-7).

There is a strong correlation between the colour of human hair and the variants of MC1-R (Valverde et al., Nat. Genet. 1995 November; 11(3): 328-30). Functional variations of MC1-R are associated with the ginger hair colour.

It is also known that the sebaceous gland expresses both MC1-R (Ganceviciene et al., Exp. Dermatol. 2007 July; 16(7): 547-52) and MC5-R (Zhang et al., Peptides, 2006 February; 27(2):413-20). It has also been reported that MC1-R is overexpressed in the sebaceous gland in the case of acne.

Thus, the compounds according to the present invention find applications in human medicine, especially in dermatology, and in the field of cosmetics.

Patents WO 96/35713, WO 96/38471 and WO 99/58501 disclose certain dipeptides and their use for stimulating the synthesis of growth hormone.

The publication in the Journal of Medicinal Chemistry (2003), 46, 1123-1126 describes the "discovery of small, powerful and selective tyrosine-based agonist molecules of the MC1-R receptor that have anti-inflammatory properties".

Patents WO 02/070 511, WO 02/079 146 and WO 02/069 905 claim the use of compounds as modulators of melanocortin receptors, more particularly MC1-R and MC4-R.

Patent WO 05/047 253 describes compounds and their use as melanocortin receptor agonists.

Now, the Applicant has found, surprisingly and unexpectedly, that certain compounds of structure (I), which is the subject of the present invention, are modulators of one or more melanocortin receptors, and in particular certain compounds are active on MC1-R and have physicochemical properties suited to topical administration.

Specifically, the compounds according to the invention advantageously have several advantages imparted by their physicochemical properties, allowing topical administration and especially making it possible to access the target rapidly and in a directed manner, to reduce the amounts of active agent required for activity on the target, to reduce the systemic exposure and also to have fewer side effects.

Thus, the present invention relates to compounds of general formula (I) below:

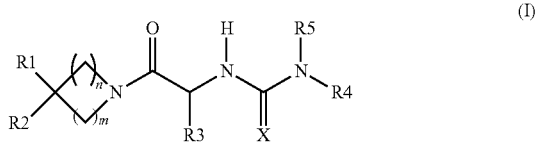

in which:

R1 represents a hydrogen atom, an aryl, a substituted aryl, an alkyl, a cycloalkyl, a cycloalkylalkyl or a cycloalkylalkylalkyl, R2 represents a hydrogen atom, a hydroxyl, a lower alkyl, a substituted lower alkyl, a higher alkyl, a substituted higher alkyl, a cycloalkyl, a cycloalkylalkyl, a lower alkoxy, a substituted lower alkoxy, a higher alkoxy, a substituted higher alkoxy, a cycloalkylalkoxy, an acyloxy, an acyl, an alkoxycarbonyl, a carboxamide, a carboxylic acid, a cyano, or an amino disubstituted with an acyl and an aryl or alkyl, R3 represents an aralkyl or a substituted aralkyl, R4 represents a heteroaralkyl or a substituted heteroaralkyl, R5 represents a hydrogen atom or an alkyl, X represents an oxygen atom or a sulfur atom, n, m may be equal to 1 or 2;

and also the corresponding salts and enantiomers.

Figure 1:
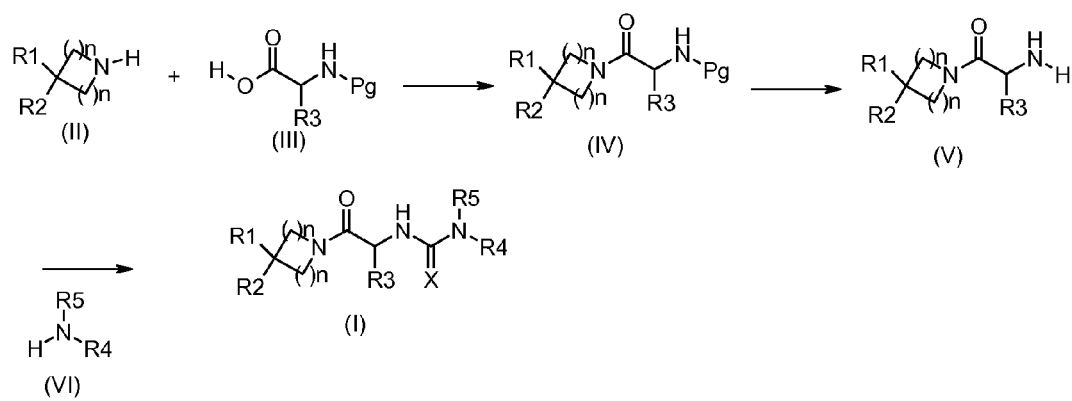
FIG. 1 is a general reaction scheme showing the preparation of the compounds of formula (I) as described in more detail below.

Among the addition salts of the compounds of general formula (I) with a pharmaceutically acceptable acid, mention may be made preferably of the salts with an organic acid or with a mineral acid.

The suitable mineral acids are, for example, hydrohalic acids, for instance hydrochloric acid or hydrobromic acid, sulfuric acid and nitric acid.

The suitable organic acids are, for example, picric acid, methanesulfonic acid, ethanesulfonic acid, para-toluenesulfonic acid, oxalic acid and tartaric acid.

The compounds of general formula (I) may also exist in the form of hydrates or solvates with water or with a solvent.

The suitable solvents for forming solvates or hydrates are, for example, alcohols, for instance ethanol or isopropanol, or water.

According to the present invention, the term "aryl" denotes an unsubstituted phenyl or naphthyl.

According to the present invention, the term "substituted aryl" denotes a phenyl or a naphthyl substituted with one or more groups of atoms chosen from an alkyl, an alkoxy, a halogen, a hydroxyl, a cyano, a trifluoromethyl and a nitro.

According to the present invention, the term "cycloalkyl" denotes a saturated cyclic hydrocarbon-based chain containing from 3 to 7 carbon atoms.

According to the present invention, the term "hydroxyl" means the OH group.

According to the present invention, the term "amino" means the $NH_2$ group.

According to the present invention, the term "cyano" denotes the CN group.

According to the present invention, the term "carboxylic acid" denotes the $CO_2H$ group.

According to the present invention, the term "acyl" denotes a formyl or a carbonyl substituted with an alkyl, a cycloalkyl or a cycloalkylalkyl.

According to the present invention, the term "alkyl" denotes a substituted or unsubstituted lower alkyl or higher alkyl.

According to the present invention, the term "lower alkyl" denotes a linear or branched, saturated or unsaturated hydrocarbon-based chain containing from 1 to 4 carbon atoms or an unsaturated chain containing from 2 to 4 carbon atoms and especially, for example, methyl, ethyl, propyl, isopropyl and butyl.

According to the present invention, the term "substituted lower alkyl" means a linear or branched, saturated or unsaturated hydrocarbon-based chain containing from 1 to 4 carbon atoms and substituted with one or more halogen atoms or with a hydroxyl, or an unsaturated hydrocarbon-based chain containing from 2 to 4 carbon atoms and substituted with one or more halogen atoms or with a hydroxyl.

According to the present invention, the term "higher alkyl" denotes a linear or branched, saturated or unsaturated hydrocarbon-based chain containing from 5 to 10 carbon atoms.

According to the present invention, the term "substituted higher alkyl" denotes a linear or branched, saturated or unsaturated hydrocarbon-based chain containing from 5 to 10 carbon atoms and substituted with one or more halogen atoms or with a hydroxyl.

According to the present invention, the term "halogen atom" denotes chlorine, fluorine, iodine and bromine atoms.

According to the present invention, the term "cycloalkylalkyl" denotes an alkyl substituted with a cycloalkyl.

According to the present invention, the term "lower alkoxy" denotes an oxygen atom substituted with a lower alkyl and especially, for example, methoxy, ethoxy, propoxy, isopropoxy or butoxy.

According to the present invention, the term "substituted lower alkoxy" denotes an oxygen atom substituted with a substituted lower alkyl.

According to the present invention, the term "higher alkoxy" denotes an oxygen atom substituted with a higher alkyl.

According to the present invention, the term "substituted higher alkoxy" denotes an oxygen atom substituted with a substituted higher alkyl.

According to the present invention, the term "cycloalkylalkoxy" denotes an oxygen atom substituted with a cycloalkylalkyl.

According to the present invention, the term "acyloxy" denotes an oxygen atom substituted with an acyl.

According to the present invention, the term "alkoxycarbonyl" denotes a carbonyl substituted with an alkoxy, cycloalkoxy or a cycloalkylalkoxy.

According to the present invention, the term "carboxamide" denotes a carbonyl substituted with a monoalkylamino or a dialkylamino.

According to the present invention, the term "aralkyl" denotes an alkyl substituted with an aryl.

According to the present invention, the term "substituted aralkyl" denotes an alkyl substituted with a substituted aryl.

According to the present invention, the term "heterocycle" denotes a saturated or unsaturated, cyclic or bicyclic hydrocarbon-based chain, comprising one or more heteroatoms chosen from O, S and N.

According to the present invention, the term "substituted heterocycle" denotes a saturated or unsaturated, cyclic or bicyclic hydrocarbon-based chain, comprising one or more heteroatoms chosen from O, S and N substituted with one or more alkyl groups.

According to the present invention, the term "heteroaryl" denotes an aromatic heterocycle.

According to the present invention, the term "substituted heteroaryl" denotes an aromatic heterocycle substituted with one or more alkyl groups.

According to the present invention, the term "heteroaralkyl" denotes an alkyl substituted with a heteroaryl.

According to the present invention, the term "substituted heteroaralkyl" denotes an alkyl substituted with a substituted heteroaryl.

Among the compounds of general formula (I) included in the context of the present invention, mention may be made especially of the following:

1-[(S)-2-(4-Butyryl-4-phenylpiperidin-1-yl)-1-(4-methoxybenzyl)-2-oxoethyl]-3-[2-(1H-imidazol-4-yl)ethyl]urea 1-[2-(1H-Imidazol-4-yl)ethyl]-3-[1-(4-methoxybenzyl)-2-oxo-2-(4-oxo-1-phenyl-1,3,8-triazaspiro[4.5]dec-8-yl)ethyl]urea 1-[2-(4-Cyano-4-phenylpiperidin-1-yl)-1-(4-methoxybenzyl)-2-oxoethyl]-3-[2-(1H-imidazol-4-yl)ethyl]urea 1-[2-(1H-Imidazol-4-yl)ethyl]-3-[1-(4-methoxybenzyl)-2-oxo-2-(4-phenylpiperidin-1-yl)ethyl]urea 1-[2-(1H-Imidazol-4-yl)ethyl]-3-[1-(4-methoxybenzyl)-2-oxo-2-piperidin-1-yl-ethyl]urea Ethyl 4-cyclohexyl-1-[2-{3-[2-(1H-imidazol-4-yl)ethyl]ureido}-3-(4-methoxyphenyl)-propionyl]piperidine-4-carboxylate N-{1-[2-{3-[2-(1H-Imidazol-4-yl)ethyl]ureido}-3-(4-methoxyphenyl)propionyl]piperidin-4-yl}-N-phenylpropionamide 1-[2-{3-[2-(1H-Imidazol-4-yl)ethyl]ureido}-3-(4-methoxyphenyl)propionyl]-3-phenyl-azetidin-3-yl butyrate Ethyl 1-[2-{3-[2-(1H-Imidazol-4-yl)ethyl]ureido}-3-(4-methoxyphenyl)propionyl]piperidine-4-carboxylate 1-[2-(1H-Imidazol-4-yl)ethyl]-3-{1-(4-methoxybenzyl)-2-[4-(2-methoxyphenyl)-piperidin-1-yl]-2-oxoethyl}urea 1-[2-(3-Butoxy-3-phenylazetidin-1-yl)-1-(4-methoxybenzyl)-2-oxoethyl]-3-[2-(1H-imidazol-4-yl)ethyl]urea Methyl 4-cyclohexyl-1-[2-{3-[2-(1H-imidazol-4-yl)ethyl]ureido}-3-(4-methoxyphenyl)-propionyl]piperidine-4-carboxylamide 1-[2-(3-Cyclohexanecarbonylazetidin-1-yl)-1-(4-methoxybenzyl)-2-oxoethyl]-3-[2-(1H-imidazol-4-yl)ethyl]urea Ethyl 4-cyclohexyl-1-[2-{3-ethyl-3-[2-(1H-imidazol-4-yl)ethyl]ureido}-3-(4-methoxy-phenyl)propionyl]piperidine-4-carboxylate N-Cyclopropyl-N-{1-[2-{3-[2-(1H-imidazol-4-yl)ethyl]ureido}-3-(4-methoxyphenyl)-propionyl]piperidin-4-yl}propionamide Ethyl 4-cyclohexyl-1-(2-{3-[2-(1H-imidazol-4-yl)ethyl]ureido}-3-phenylpropionyl)-piperidine-4-carboxylate 1-[2-(4-Butyryl-4-cyclohexylpiperidin-1-yl)-1-(4-methoxybenzyl)-2-oxoethyl]-3-[2-(3H-imidazol-4-yl)ethyl]urea 1-[2-(4-Butoxy-4-cyclohexylpiperidin-1-yl)-1-(4-methoxybenzyl)-2-oxoethyl]-3-[2-(1H-imidazol-4-yl)ethyl]urea Ethyl 4-cyclohexyl-1-(2-{3-[2-(1H-imidazol-4-yl)ethyl]ureido}-2-phenylacetyl)-piperidine-4-carboxylate Methyl 4-cyclohexyl-1-[2-{3-[2-(1H-imidazol-4-yl)ethyl]ureido}-3-(4-methoxyphenyl)-propionyl]piperidine-4-carboxylate 1-[2-(4-Cyclohexyl-4-ethoxypiperidin-1-yl)-1-(4-methoxybenzyl)-2-oxoethyl]-3-[2-(1H-imidazol-4-yl)ethyl]urea 1-[2-(4-Acetyl-4-cyclohexylpiperidin-1-yl)-1-(4-methoxybenzyl)-2-oxoethyl]-3-[2-(1H-imidazol-4-yl)ethyl]urea Methyl 4-cyclohexyl-1-(2-{3-[2-(1H-imidazol-4-yl)ethyl]ureido}-2-phenylacetyl)-piperidine-4-carboxylate Ethyl 4-ethyl-1-[2-{3-[2-(1H-imidazol-4-yl)ethyl]ureido}-3-(4-methoxyphenyl)-propionyl]piperidine-4-carboxylate 1-[2-(4-Cyclohexyl-4-propoxypiperidin-1-yl)-1-(4-methoxybenzyl)-2-oxoethyl]-3-[2-(1H-imidazol-4-yl)ethyl]urea 4-Cyclohexyl-1-[2-{3-[2-(1H-imidazol-4-yl)ethyl]ureido}-3-(4-methoxyphenyl)-propionyl]piperidine-4-carboxylic acid 1-[2-(1H-Imidazol-4-yl)ethyl]-3-{1-(4-methoxybenzyl)-2-[3-(2-methylcyclohexyl)-3-propoxyazetidin-1-yl]-2-oxoethyl}urea Propyl 4-cyclohexyl-1-[2-{3-[2-(1H-imidazol-4-yl)ethyl]ureido}-3-(4-methoxyphenyl)-propionyl]piperidine-4-carboxylate 1-[2-(1H-Imidazol-4-yl)ethyl]-3-[1-(4-methoxybenzyl)-2-oxo-2-(3-pentyl-3-phenyl-azetidin-1-yl)ethyl]urea Ethyl 1-((R)-3-(4-chlorophenyl)-2-{3-[2-(1H-imidazol-4-yl)ethyl]ureido}propionyl)-4-cyclohexylpiperidine-4-carboxylate Ethyl 1-((S)-3-(4-chlorophenyl)-2-{3-[2-(1H-imidazol-4-yl)ethyl]ureido}propionyl)-4-cyclohexylpiperidine-4-carboxylate 1-[2-(4-Cyclohexyl-4-propionylpiperidin-1-yl)-1-(4-methoxybenzyl)-2-oxoethyl]-3-[2-(1H-imidazol-4-yl)ethyl]urea 1-[2-(4-Cyclohexyl-4-propionylpiperidin-1-yl)-1-(4-methoxybenzyl)-2-oxoethyl]-3-(1H-imidazol-4-ylmethyl)urea Ethyl 4-cyclohexyl-1-[(R)-2-{3-[2-(1H-imidazol-4-yl)ethyl]ureido}-3-(4-methoxyphenyl)propionyl]piperidine-4-carboxylate Ethyl 4-cyclopropylmethyl-1-[2-{3-[2-(1H-imidazol-4-yl)ethyl]ureido}-3-(4-methoxy-phenyl)propionyl]piperidine-4-carboxylate Propyl 4-cyclohexyl-1-(2-{3-[2-(1H-imidazol-4-yl)ethyl]ureido}-3-phenylpropionyl)-piperidine-4-carboxylate Ethyl 4-cyclopentyl-1-(2-{3-[2-(1H-imidazol-4-yl)ethyl]ureido}-3-phenylpropionyl)-piperidine-4-carboxylate Ethyl 4-cyclopentyl-1-[2-{3-[2-(1H-imidazol-4-yl)ethyl]ureido}-3-(4-methoxyphenyl)-propionyl]piperidine-4-carboxylate Ethyl 4-cyclohexyl-1-[(S)-2-{3-[2-(1H-imidazol-4-yl)ethyl]ureido}-3-(4-methoxyphenyl)-propionyl]piperidine-4-carboxylate 1-[(R)-2-(4-Butyryl-4-cyclohexylpiperidin-1-yl)-1-(4-methoxybenzyl)-2-oxoethyl]-3-[2-(1H-imidazol-4-yl)ethyl]urea 1-[(R)-2-(4-Butyryl-4-cyclohexylpiperidin-1-yl)-1-(4-fluorobenzyl)-2-oxoethyl]-3-[2-(2H-imidazol-4-yl)ethyl]urea
1-[(R)-1-Benzyl-2-(4-butyryl-4-cyclohexylpiperidin-1-yl)-2-oxoethyl]-3-[2-(1H-imidazol-4-yl)ethyl]urea
1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea
1-[(R)-2-(4-Butyryl-4-cyclohexylpiperidin-1-yl)-1-(4-chlorobenzyl)-2-oxoethyl]-3-[2-(1H-imidazol-4-yl)ethyl]urea
Ethyl 4-cyclohexyl-1-((R)-3-(3,4-dichlorophenyl)-2-{3-[3-(1H-imidazol-4-yl)propyl]-ureido}propionyl)piperidine-4-carboxylate
Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate
Ethyl 4-cyclohexyl-1-[(R)-2-{3-[2-(1H-imidazol-4-yl)ethyl]thioureido}-3-(4-methoxy-phenyl)propionyl]piperidine-4-carboxylate
1-[(R)-2-(4-Butyryl-4-cyclohexylpiperidin-1-yl)-1-(4-methoxybenzyl)-2-oxoethyl]-3-[2-(1H-imidazol-4-yl)ethyl]thiourea
1-[(R)-2-(4-Cyclohexyl-4-propoxypiperidin-1-yl)-1-(4-methoxybenzyl)-2-oxoethyl]-3-[2-(1H-imidazol-4-yl)ethyl]thiourea
1-[(R)-1-Benzyl-2-(4-cyclohexyl-4-propoxypiperidin-1-yl)-2-oxoethyl]-3-[2-(1H-imidazol-4-yl)ethyl]thiourea
1-[(R)-1-Benzyl-2-(4-cyclohexyl-4-propoxypiperidin-1-yl)-2-oxoethyl]-3-[2-(1H-imidazol-4-yl)ethyl]urea
Ethyl 4-cyclohexyl-1-((R)-3-(4-methoxyphenyl)-2-{3-[2-(3-methyl-3H-imidazol-4-yl)ethyl]thioureido}propionyl)piperidine-4-carboxylate
Ethyl 4-cyclohexyl-1-((R)-2-{3-[2-(3-methyl-3H-imidazol-4-yl)ethyl]ureido}-3-phenyl-propionyl)piperidine-4-carboxylate
1-[(R)-2-(4-Cyclohexyl-4-propoxypiperidin-1-yl)-1-(4-methoxybenzyl)-2-oxoethyl]-3-[2-(3-methyl-3H-imidazol-4-yl)ethyl]urea
Ethyl 1-((R)-3-(4-chlorophenyl)-2-{3-[2-(3-methyl-3H-imidazol-4-yl)ethyl]ureido}-propionyl)-4-cyclohexylpiperidine-4-carboxylate
Ethyl 4-cyclohexyl-1-((R)-3-(4-fluorophenyl)-2-{3-[2-(3-methyl-3H-imidazol-4-yl)ethyl]-ureido}propionyl)piperidine-4-carboxylate
Ethyl 4-cyclohexyl-1-((R)-3-(4-fluorophenyl)-2-{3-[2-(1H-imidazol-4-yl)ethyl]ureido}-propionyl)piperidine-4-carboxylate
Ethyl 4-cyclohexyl-1-((R)-3-(4-fluorophenyl)-2-{3-[2-(1H-imidazol-4-yl)ethyl]thio-ureido}propionyl)piperidine-4-carboxylate
Ethyl 1-((R)-3-(4-chlorophenyl)-2-{3-[2-(1H-imidazol-4-yl)ethyl]thioureido}propionyl)-4-cyclohexylpiperidine-4-carboxylate
Ethyl 1-((R)-3-(4-chlorophenyl)-2-{3-[2-(3-methyl-3H-imidazol-4-yl)ethyl]thioureido}-propionyl)-4-cyclohexylpiperidine-4-carboxylate
1-[(R)-2-(4-Cyclohexyl-4-propoxypiperidin-1-yl)-1-(4-fluorobenzyl)-2-oxoethyl]-3-[2-(1H-imidazol-4-yl)ethyl]urea
1-[(R)-1-(4-Chlorobenzyl)-2-(4-cyclohexyl-4-propoxypiperidin-1-yl)-2-oxoethyl]-3-[2-(1H-imidazol-4-yl)ethyl]urea and also the respective salts and enantiomers thereof.

The compounds of general formula (I) are prepared according to the general reaction schemes presented in FIG. 1.

Using reaction scheme 1 (FIG. 1):

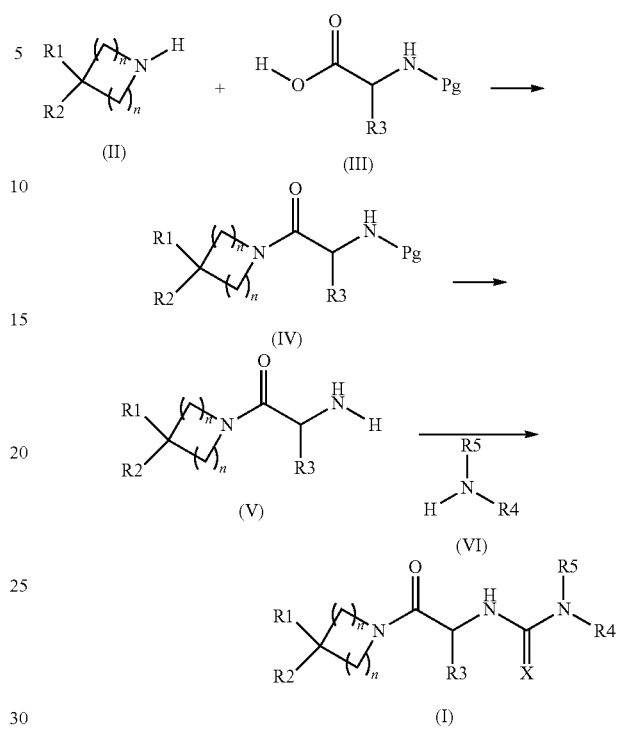

According to scheme 1, the compounds of formula (IV) may be prepared by coupling between the intermediates of formula (II) and an amino acid of formula (III) whose amine function is protected with a protecting group Pg (for example a Boc, CBz or Fmoc group), under standard peptide coupling conditions (Han, S., Kim, Y. *Tetrahedron*, 2004, 60, 2447-2467; Albericio, F. *Current Opinion in Chemical Biology*, 2004, 8, 211-221; Humphrey, J., Chamberlin, R. *Chem. Rev.*, 1997, 97, 2243-2266), using, for example, as coupling agent 1-(3-dimethylaminopropyl)-3-ethylcarbodiimide hydrochloride, hydroxybenzotriazole or TBTU, and as base triethylamine or diisopropylethylamine, in a solvent such as dichloromethane or dimethylformamide.

The amino acids of general formula (IV) are commercially available or may be prepared via methods described in the literature (Williams, R. M., Synthesis of optically active α-amino acids, Pergamon Press, Oxford, 1989).

The compounds of formula (V) are obtained by deprotection of the amine function of the compounds of formula (IV), via methods chosen from those known to a person skilled in the art. They include, inter alia, the use of trifluoroacetic acid or hydrochloric acid in dichloromethane, or ethyl acetate, for example in the case of a protection with a Boc group, hydrogenation with the appropriate metal in tetrahydrofuran or methanol, for example in the case of a protection with a CBz group, and piperidine in acetonitrile, for example in the case of a protection with an Fmoc group.

In a final step, the compounds of formula (I) may be prepared by adding the amines of formula (VI) to isocyanates or isothiocyanates obtained from the compounds (V) in dichloromethane or dimethylformamide, for example. The isocyanates may be prepared from the amines (V) in the presence of phosgene, diphosgene or triphosgene, for example. The isothiocyanates may be prepared from the amines (V) in the presence of thiophosgene (Nowick J. S. et al., JOC (1996)

3929-3934), or bis(2-pyridyl) thionocarbonate (WO 2008/008 954), for example. The compounds of formula (I) may also be synthesized by adding the amines of formula (VI) to activated carbamates obtained from the amines (V) in dichloromethane or dimethylformamide, for example. The term "activated carbamate" means, for example, a para-nitrophenyl carbamate group (Igarashi, T., Synlett (2007) 1436), which may be obtained by adding para-nitrophenyl chloroformate to the amine (V) in the presence of a base, which may be, for example, triethylamine in dichloromethane or dimethylformamide.

The compounds of formula (II) are commercially available or may be prepared according to the methods described in the literature or known to those skilled in the art, adapted as a function of the nature of the substituents R1 and R2. Schemes 1 to 9 below show examples of preparation of the compounds of formula (II).

For example, when R2 contains an acyloxy or carboxamide chain, the preparation of the compound (II, n, m=2) may be performed according to scheme 1:

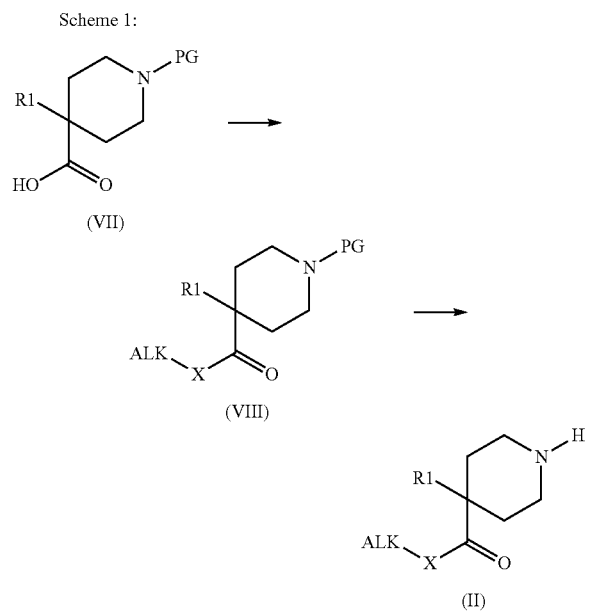

The compounds of formula (VIII) are obtained:
when X is an oxygen, for example, by esterification of the carboxylic acid function of the compounds (VII) using the methods described in the literature, or
when X is a nitrogen, for example by addition to an amine or to an acid chloride obtained from the carboxylic acid (VII) using methods chosen from those known to a person skilled in the art. It is especially possible to use oxalyl chloride or thionyl chloride in solvents such as dichloromethane or dimethylformamide.

The compounds of formula (II) are obtained by deprotection of the amine function of the compounds of formula (VIII), via methods chosen from those known to a person skilled in the art. They include, inter alia, the use of trifluoroacetic acid or hydrochloric acid in dichloromethane, or ethyl acetate, for example in the case of a protection with a Boc group, hydrogenation with the appropriate metal in tetrahydrofuran or methanol, for example in the case of a protection with a CBz group, and piperidine in acetonitrile, for example in the case of a protection with an Fmoc group.

For example, when R1 contains an alkyl, cycloalkyl or cycloalkylalkyl group and R2 contains an acyloxy chain, the preparation of the compound (II, n, m=2) may be performed according to scheme 2:

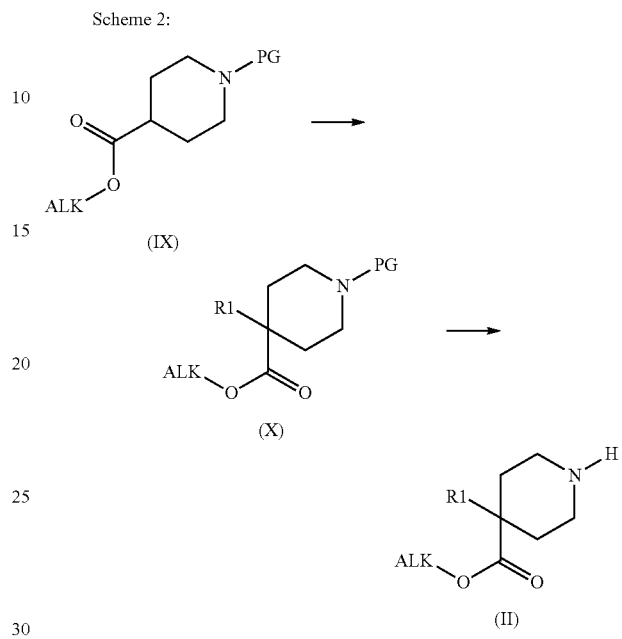

The introduction of the group R1 may be performed, for example, by alpha deprotonation of the ester function of compound (IX) in the presence of a base such as lithium diisopropylamide or lithium hexamethyldisilazide in solvents such as dichloromethane or tetrahydrofuran. The compounds of formula (II) are obtained by deprotection of the amine function of the compounds of formula (X), via methods chosen from those known to a person skilled in the art. They include, inter alia, the use of trifluoroacetic acid or hydrochloric acid in dichloromethane, or ethyl acetate, for example in the case of a protection with a Boc group, hydrogenation with the appropriate metal in tetrahydrofuran or methanol, for example in the case of a protection with a CBz group.

For example, when R2 contains an alkoxy or an alkoxycarbonyl chain, the preparation of the compound (II, n, m=1) may be performed according to scheme 3:

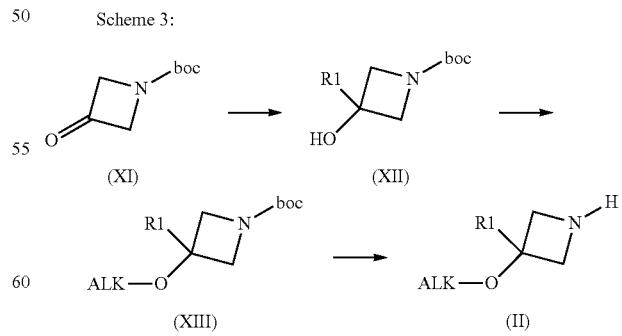

The compounds of formula (XII) are obtained, for example, by addition of a magnesium halide derived from R1 to the N-Boc-azetidinone (XI) followed by alkylation or acylation of the tertiary alcohol according to methods conventionally described in the literature, to lead to the compounds (XIII). The compounds of formula (II) are obtained by deprotection of the amine function of the compounds of formula (XIII), for example in the presence of trifluoroacetic acid or hydrochloric acid in dichloromethane or ethyl acetate.

For example, when R2 contains an acyl group, the preparation of the compound (II, n=m=1) may be performed according to scheme 4:

Scheme 4:

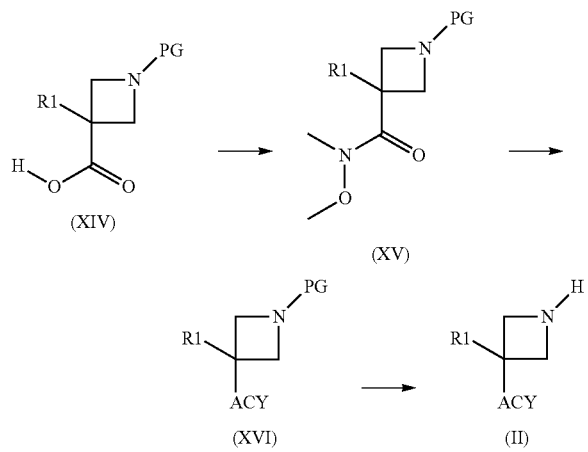

The compounds of formula (XV) may be obtained under peptide coupling conditions between compounds with a carboxylic acid (XIV) and the Weinreb amine, using, for example, as coupling agent, 1-(3-dimethylaminopropyl)-3-ethylcarbodiimide hydrochloride, hydroxybenzotriazole or TBTU, and, as base, triethylamine or diisopropylethylamine, in a solvent such as dichloromethane or dimethylformamide. The compounds of formula (XVI) are obtained, for example, by addition of a magnesium halide derived from R1 to the derivative of the Weinreb amide (XV). The compounds of formula (II) are obtained by deprotection of the amine function of the compounds of formula (X), via methods chosen from those known to a person skilled in the art. They include, inter alia, the use of trifluoroacetic acid or hydrochloric acid in dichloromethane, or ethyl acetate, for example in the case of a deprotection with a Boc group, hydrogenation with the appropriate metal in tetrahydrofuran or methanol, for example in the case of a protection with a CBz group.

For example, when R2 contains a disubstituted amine, the preparation of the compound (II, n=m=2) may be performed according to scheme 5:

Scheme 5:

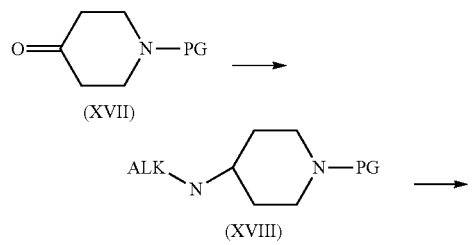

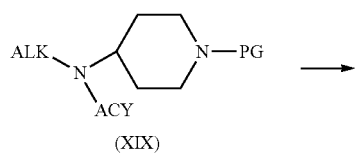

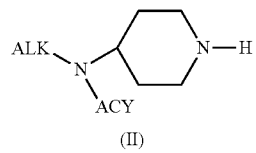

The compounds of formula (XVIII) may be obtained under reductive amination conditions between the commercially available ketone (XVII) and an amine in the presence of sodium borohydride or sodium cyanoborohydride, for example. The secondary amines (XVIII) may then be acylated in the presence of a base such as triethylamine and of an acid chloride, for example, to give the compounds (XIX). The compounds of formula (II) are obtained by deprotection of the amine function of the compounds of formula (VIII), via methods chosen from those known to a person skilled in the art. They include, inter alia, the use of trifluoroacetic acid or hydrochloric acid in dichloromethane or ethyl acetate, for example in the case of a protection with a Boc group, hydrogenation with the appropriate metal in tetrahydrofuran or methanol, for example in the case of a protection with a CBz group, and of piperidine in acetonitrile, for example in the case of a protection with an Fmoc group.

For example, when R1 contains a cyclohexyl and R2 contains an acyl group, the preparation of the compound (II, n=m=2) may be performed according to scheme 6:

Scheme 6:

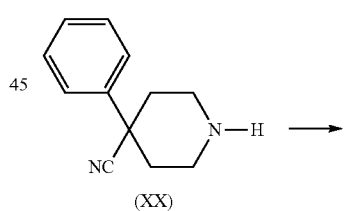

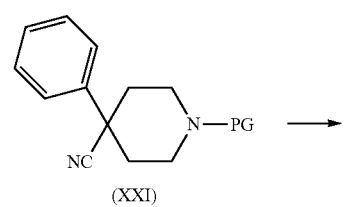

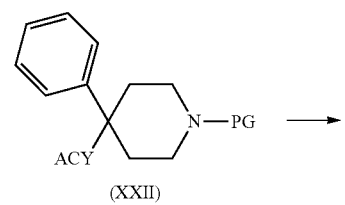

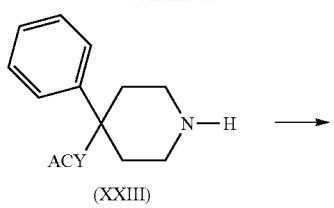

(XXIII)

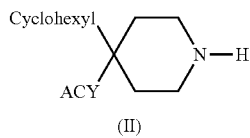

(II)

After protection of the commercially available amine (XX) with a tosylate group, for example by reacting tosyl chloride in the presence of a base such as triethylamine in dichloromethane, the compounds (XXI) are obtained. The compounds of formula (XXII) are obtained, for example, by addition of a magnesium halide derived from an alkyl in toluene to the nitrile function of the derivatives (XXI) followed by a hydrolysis in acidic medium of the intermediate imine, which may be hydrochloric acid. The compounds of formula (XXIII) are obtained by deprotection of the amine function in acidic medium, which may be sulfuric acid in the case of a tosylate group. The compounds (II) are obtained, for example, by hydrogenation of compound (X) in the presence of a catalyst, which may be rhodium on alumina or platinum oxide in dioxane, for example.

For example, when R1 contains a cyclohexyl and R2 contains an alkoxy group, the preparation of the compound (II, n=m=2) may be performed according to scheme 7:

Scheme 7:

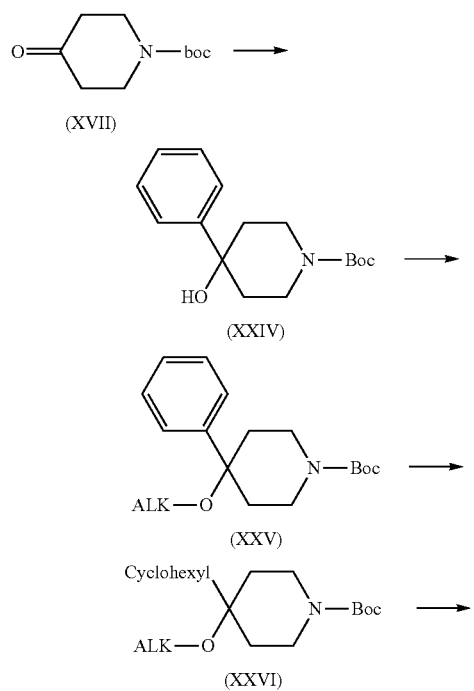

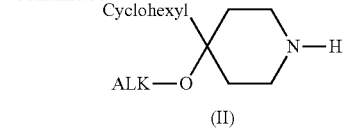

(II)

The compounds of formula (XXIV) are obtained, for example, by addition of a magnesium halide derived from a phenyl to the commercially available ketone (XVII) followed by alkylation of the tertiary alcohol according to methods conventionally described in the literature, to give the compounds (XXV). The compounds (XXVI) are obtained, for example, by hydrogenation of compound (XXV) in the presence of a catalyst, which may be rhodium on alumina or platinum oxide in dioxane, for example. The compounds of formula (II) are obtained by deprotection of the amine function of the compounds of formula (XXVI), for example in the presence of trifluoroacetic acid or hydrochloric acid in dichloromethane or ethyl acetate.

For example, when R1 is an aryl group and R2 contains an alkyl chain, the preparation of the compound (II, n=m=1) may be performed according to scheme 8:

Scheme 8:

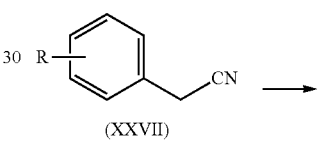

(XXVII)

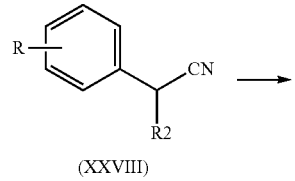

(XXVIII)

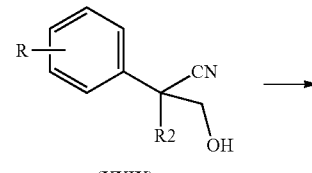

(XXIX)

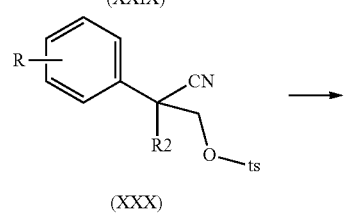

(XXX)

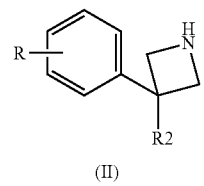

(II)

The compounds of formula (XXVIII) may be obtained, for example, by addition of a base, such as sodium hydride, in the presence of a halogenated derivative derived from R2 to the commercially available nitrile derivatives (XXVII). The primary alcohols (XXIX) may be synthesized from the nitrile derivatives (XXVIII) in the presence of a base, for example sodium hydride and paraformaldehyde. The primary alcohol function of the compounds (XXIX) may be converted into sulfonate in the presence of a base, which may be triethylamine, and of tosyl chloride, for example. The azetidine compounds (II) may be synthesized by intramolecular cyclization between an amine function obtained after reduction of the nitrile function, for example, in the presence of lithium aluminium hydride and the tosylate function.

The compounds of formula (VI) are commercially available or may be prepared according to the methods described in the literature or known to those skilled in the art, adapted as a function of the nature of the substituents R4 and R5. Schemes 9 to 11 below present examples of preparation of the compounds of formula (VI).

For example, when R5 is an alkyl group and R4 contains a heteroaralkyl group, the preparation of compound (VI) may be performed, for example, by following a protocol described in the literature (Durant G. J., Emmet J. C., Ganellin C. R., Roe A. M., (1973) Br. Pat. 1 341 375) as described in scheme 9:

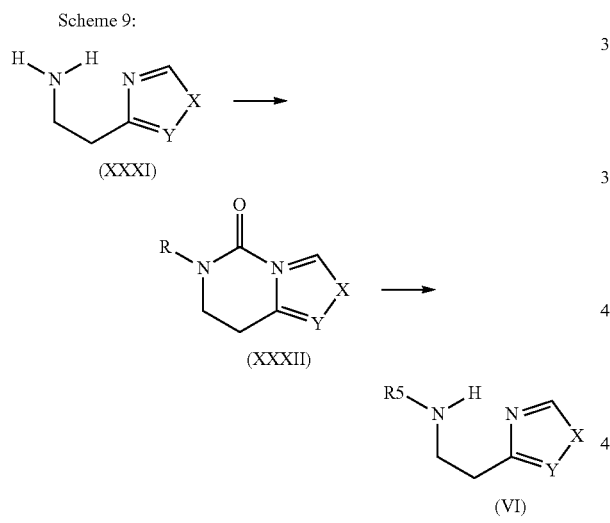

For example, when R4 contains a 1,2,3-triazole heterocycle, the preparation of compound (VI) may be performed according to scheme 10:

Scheme 10:

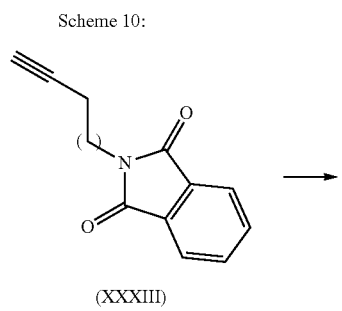

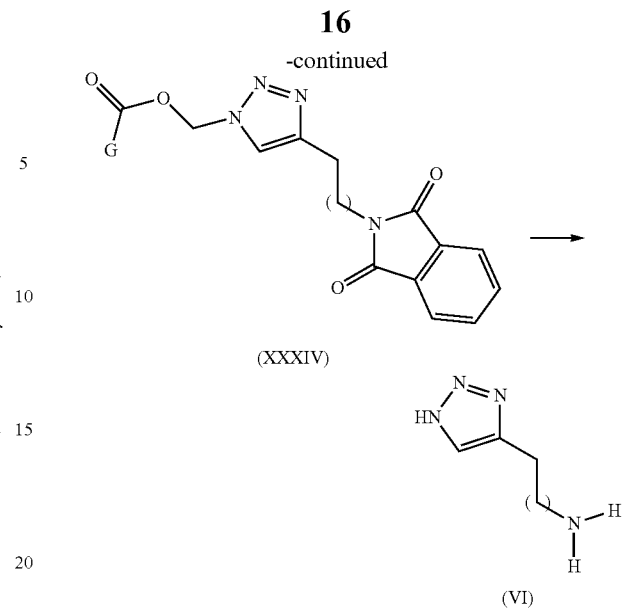

The compounds of formula (XXXIV) may be prepared via methods described in the literature (Loren J. C., Synlett, 2005, 2847-2850) followed by cleavage in basic medium in the presence, for example, of sodium hydroxide, to give the compounds (VI).

For example, when R4 contains a heteroaralkyl, the preparation of compound (VI) may be performed according to scheme 11:

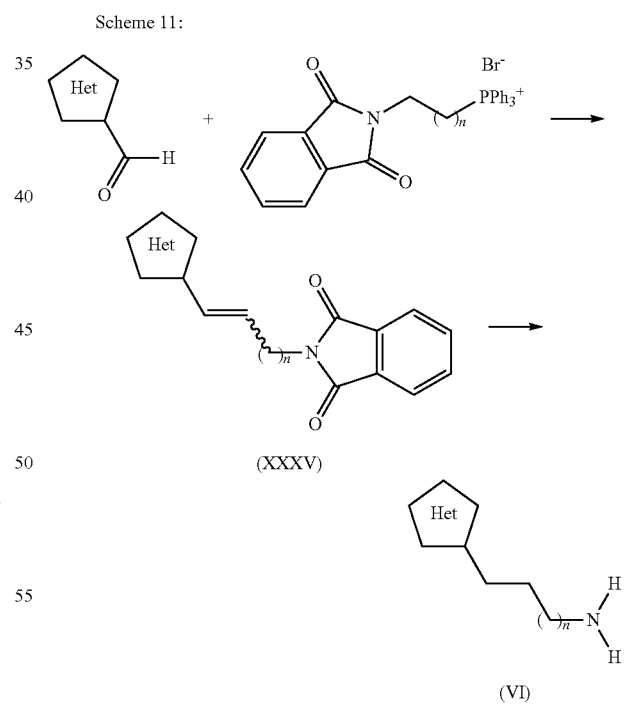

The compounds of formula (VI) may be prepared via methods described in the literature (Wolin R., BOMCL, 1998, 2157) via a Wittig reaction between aldehydes substituted with heteroaryls and commercially available ylides to form the alkenes (XXXV) followed by a hydrogenation of the double bond and hydrazinolysis of the phthalimide to generate the compounds (VI).

According to the present invention, the compounds of general formula (I) that are particularly preferred are those for which:

R1 represents a hydrogen atom, an aryl, a substituted aryl, an alkyl, a cycloalkyl or a cycloalkylalkyl, R2 represents a hydrogen atom, a lower alkyl, a substituted lower alkyl, a higher alkyl, a substituted higher alkyl, a cycloalkyl, a cycloalkylalkyl, a lower alkoxy, a substituted lower alkoxy, a higher alkoxy, a substituted higher alkoxy, a cycloalkylalkoxy, an acyloxy, an acyl, an alkoxycarbonyl, a carboxamide or a cyano, R3 represents an aralkyl or a substituted aralkyl, R4 represents a heteroaralkyl or a substituted heteroaralkyl, R5 represents a hydrogen atom, X represents an oxygen atom or a sulfur atom, n, m may be equal to 1 or 2; and also the corresponding salts and enantiomers.

Among the compounds of general formula (I) falling within the context of the present invention, mention may be made especially of the following:

1-[(S)-2-(4-Butyryl-4-phenylpiperidin-1-yl)-1-(4-methoxybenzyl)-2-oxoethyl]-3-[2-(1H-imidazol-4-yl)ethyl]urea
1-[2-(4-Cyano-4-phenylpiperidin-1-yl)-1-(4-methoxybenzyl)-2-oxoethyl]-3-[2-(1H-imidazol-4-yl)ethyl]urea
1-[2-(1H-Imidazol-4-yl)ethyl]-3-[1-(4-methoxybenzyl)-2-oxo-2-(4-phenylpiperidin-1-yl)ethyl]urea
Ethyl 4-cyclohexyl-1-[2-{3-[2-(1H-imidazol-4-yl)ethyl]ureido}-3-(4-methoxyphenyl)-propionyl]piperidine-4-carboxylate
Ethyl 1-[2-{3-[2-(1H-imidazol-4-yl)ethyl]ureido}-3-(4-methoxyphenyl)propionyl]-piperidine-4-carboxylate
1-[2-(1H-Imidazol-4-yl)ethyl]-3-{1-(4-methoxybenzyl)-2-[4-(2-methoxyphenyl)-piperidin-1-yl]-2-oxoethyl}urea
1-[2-(3-Butoxy-3-phenylazetidin-1-yl)-1-(4-methoxybenzyl)-2-oxoethyl]-3-[2-(1H-imidazol-4-yl)ethyl]urea
Methyl 4-cyclohexyl-1-[2-{3-[2-(1H-imidazol-4-yl)ethyl]ureido}-3-(4-methoxyphenyl)-propionyl]piperidine-4-carboxylamide
1-[2-(3-Cyclohexanecarbonylazetidin-1-yl)-1-(4-methoxybenzyl)-2-oxoethyl]-3-[2-(1H-imidazol-4-yl)ethyl]urea
Ethyl 4-cyclohexyl-1-[2-{3-ethyl-3-[2-(1H-imidazol-4-yl)ethyl]ureido}-3-(4-methoxy-phenyl)propionyl]piperidine-4-carboxylate
Ethyl 4-cyclohexyl-1-(2-{3-[2-(1H-imidazol-4-yl)ethyl]ureido}-3-phenylpropionyl)-piperidine-4-carboxylate
1-[2-(4-Butyryl-4-cyclohexylpiperidin-1-yl)-1-(4-methoxybenzyl)-2-oxoethyl]-3-[2-(3H-imidazol-4-yl)ethyl]urea
1-[2-(4-Butoxy-4-cyclohexylpiperidin-1-yl)-1-(4-methoxybenzyl)-2-oxoethyl]-3-[2-(1H-imidazol-4-yl)ethyl]urea
Ethyl 4-cyclohexyl-1-(2-{3-[2-(1H-imidazol-4-yl)ethyl]ureido}-2-phenylacetyl)-piperidine-4-carboxylate
Methyl 4-cyclohexyl-1-[2-{3-[2-(1H-imidazol-4-yl)ethyl]ureido}-3-(4-methoxyphenyl)-propionyl]piperidine-4-carboxylate
1-[2-(4-Cyclohexyl-4-ethoxypiperidin-1-yl)-1-(4-methoxybenzyl)-2-oxoethyl]-3-[2-(1H-imidazol-4-yl)ethyl]urea
1-[2-(4-Acetyl-4-cyclohexylpiperidin-1-yl)-1-(4-methoxybenzyl)-2-oxoethyl]-3-[2-(1H-imidazol-4-yl)ethyl]urea
Methyl 4-cyclohexyl-1-(2-{3-[2-(1H-imidazol-4-yl)ethyl]ureido}-2-phenylacetyl)-piperidine-4-carboxylate
Ethyl 4-ethyl-1-[2-{3-[2-(1H-imidazol-4-yl)ethyl]ureido}-3-(4-methoxyphenyl)-propionyl]piperidine-4-carboxylate
1-[2-(4-Cyclohexyl-4-propoxypiperidin-1-yl)-1-(4-methoxybenzyl)-2-oxoethyl]-3-[2-(1H-imidazol-4-yl)ethyl]urea
1-[2-(1H-Imidazol-4-yl)ethyl]-3-{1-(4-methoxybenzyl)-2-[3-(2-methylcyclohexyl)-3-propoxyazetidin-1-yl]-2-oxoethyl}urea
Propyl 4-cyclohexyl-1-[2-{3-[2-(1H-imidazol-4-yl)ethyl]ureido}-3-(4-methoxyphenyl)-propionyl]piperidine-4-carboxylate
1-[2-(1H-Imidazol-4-yl)ethyl]-3-[1-(4-methoxybenzyl)-2-oxo-2-(3-pentyl-3-phenyl-azetidin-1-yl)ethyl]urea
Ethyl 1-((R)-3-(4-chlorophenyl)-2-{3-[2-(1H-imidazol-4-yl)ethyl]ureido}propionyl)-4-cyclohexylpiperidine-4-carboxylate
Ethyl 1-((S)-3-(4-chlorophenyl)-2-{3-[2-(1H-imidazol-4-yl)ethyl]ureido}propionyl)-4-cyclohexylpiperidine-4-carboxylate
1-[2-(4-Cyclohexyl-4-propionylpiperidin-1-yl)-1-(4-methoxybenzyl)-2-oxoethyl]-3-[2-(1H-imidazol-4-yl)ethyl]urea
1-[2-(4-Cyclohexyl-4-propionylpiperidin-1-yl)-1-(4-methoxybenzyl)-2-oxoethyl]-3-(1H-imidazol-4-ylmethyl)urea
Ethyl 4-cyclohexyl-1-[(R)-2-{3-[2-(1H-imidazol-4-yl)ethyl]ureido}-3-(4-methoxyphenyl)-propionyl]piperidine-4-carboxylate
Ethyl 4-cyclopropylmethyl-1-[2-{3-[2-(1H-imidazol-4-yl)ethyl]ureido}-3-(4-methoxy-phenyl)propionyl]piperidine-4-carboxylate
Propyl 4-cyclohexyl-1-(2-{3-[2-(1H-imidazol-4-yl)ethyl]ureido}-3-phenylpropionyl)-piperidine-4-carboxylate
Ethyl 4-cyclopentyl-1-(2-{3-[2-(1H-imidazol-4-yl)ethyl]ureido}-3-phenylpropionyl)-piperidine-4-carboxylate
Ethyl 4-cyclopentyl-1-[2-{3-[2-(1H-imidazol-4-yl)ethyl]ureido}-3-(4-methoxyphenyl)-propionyl]piperidine-4-carboxylate
Ethyl 4-cyclohexyl-1-[(S)-2-{3-[2-(1H-imidazol-4-yl)ethyl]ureido}-3-(4-methoxyphenyl)-propionyl]piperidine-4-carboxylate
1-[(R)-2-(4-Butyryl-4-cyclohexylpiperidin-1-yl)-1-(4-methoxybenzyl)-2-oxoethyl]-3-[2-(1H-imidazol-4-yl)ethyl]urea
1-[(R)-2-(4-Butyryl-4-cyclohexylpiperidin-1-yl)-1-(4-fluorobenzyl)-2-oxoethyl]-3-[2-(1H-imidazol-4-yl)ethyl]urea
1-[(R)-1-Benzyl-2-(4-butyryl-4-cyclohexylpiperidin-1-yl)-2-oxoethyl]-3-[2-(1H-imidazol-4-yl)ethyl]urea
1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea
1-[(R)-2-(4-Butyryl-4-cyclohexylpiperidin-1-yl)-1-(4-chlorobenzyl)-2-oxoethyl]-3-[2-(1H-imidazol-4-yl)ethyl]urea
Ethyl 4-cyclohexyl-1-((R)-3-(3,4-dichlorophenyl)-2-{3-[3-(1H-imidazol-4-yl)propyl]-ureido}propionyl)piperidine-4-carboxylate
Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate
Ethyl 4-cyclohexyl-1-[(R)-2-{3-[2-(1H-imidazol-4-yl)ethyl]thioureido}-3-(4-methoxy-phenyl)propionyl]piperidine-4-carboxylate and also the respective salts and enantiomers thereof.

According to the present invention, the compounds of general formula (I) that are particularly preferred are those for which:

R1 represents a cycloalkyl or a cycloalkylalkyl,

R2 represents a lower alkoxy, a cycloalkylalkoxy, an acyl, an alkoxycarbonyl or a cyano, R3 represents an aralkyl or a substituted aralkyl, R4 represents a heteroaralkyl or a substituted heteroaralkyl, R5 represents a hydrogen atom, X represents an oxygen atom or a sulfur atom,
n, m is equal to 2; and also the corresponding salts and enantiomers.

The preferred compounds are:

Ethyl 4-cyclohexyl-1-[2-{3-[2-(1H-imidazol-4-yl)ethyl]ureido}-3-(4-methoxyphenyl)-propionyl]piperidine-4-carboxylate Ethyl 4-cyclohexyl-1-(2-{3-[2-(1H-imidazol-4-yl)ethyl]ureido}-3-phenylpropionyl)-piperidine-4-carboxylate 1-[2-(4-Butyryl-4-cyclohexylpiperidin-1-yl)-1-(4-methoxybenzyl)-2-oxoethyl]-3-[2-(3H-imidazol-4-yl)ethyl]urea 1-[2-(4-Butoxy-4-cyclohexylpiperidin-1-yl)-1-(4-methoxybenzyl)-2-oxoethyl]-3-[2-(2H-imidazol-4-yl)ethyl]urea Methyl 4-cyclohexyl-1-[2-{3-[2-(1H-imidazol-4-yl)ethyl]ureido}-3-(4-methoxyphenyl)-propionyl]piperidine-4-carboxylate 1-[2-(4-Cyclohexyl-4-ethoxypiperidin-1-yl)-1-(4-methoxybenzyl)-2-oxoethyl]-3-[2-(2H-imidazol-4-yl)ethyl]urea 1-[2-(4-Acetyl-4-cyclohexylpiperidin-1-yl)-1-(4-methoxybenzyl)-2-oxoethyl]-3-[2-(1H-imidazol-4-yl)ethyl]urea Ethyl 4-ethyl-1-[2-{3-[2-(1H-imidazol-4-yl)ethyl]ureido}-3-(4-methoxyphenyl)-propionyl]piperidine-4-carboxylate 1-[2-(4-Cyclohexyl-4-propoxypiperidin-1-yl)-1-(4-methoxybenzyl)-2-oxoethyl]-3-[2-(1H-imidazol-4-yl)ethyl]urea Propyl 4-cyclohexyl-1-[2-{3-[2-(1H-imidazol-4-yl)ethyl]ureido}-3-(4-methoxyphenyl)-propionyl]piperidine-4-carboxylate Ethyl 1-((R)-3-(4-chlorophenyl)-2-{3-[2-(1H-imidazol-4-yl)ethyl]ureido}propionyl)-4-cyclohexylpiperidine-4-carboxylate 1-[2-(4-Cyclohexyl-4-propionylpiperidin-1-yl)-1-(4-methoxybenzyl)-2-oxoethyl]-3-[2-(1H-imidazol-4-yl)ethyl]urea 1-[2-(4-Cyclohexyl-4-propionylpiperidin-1-yl)-1-(4-methoxybenzyl)-2-oxoethyl]-3-(1H-imidazol-4-ylmethyl)urea Ethyl 4-cyclohexyl-1-[(R)-2-{3-[2-(1H-imidazol-4-yl)ethyl]ureido}-3-(4-methoxyphenyl)-propionyl]piperidine-4-carboxylate Ethyl 4-cyclopropylmethyl-1-[2-{3-[2-(1H-imidazol-4-yl)ethyl]ureido}-3-(4-methoxy-phenyl)propionyl]piperidine-4-carboxylate Propyl 4-cyclohexyl-1-(2-{3-[2-(1H-imidazol-4-yl)ethyl]ureido}-3-phenylpropionyl)-piperidine-4-carboxylate Ethyl 4-cyclopentyl-1-[2-{3-[2-(1H-imidazol-4-yl)ethyl]ureido}-3-(4-methoxyphenyl)-propionyl]piperidine-4-carboxylate Ethyl 4-cyclohexyl-1-[(S)-2-{3-[2-(1H-imidazol-4-yl)ethyl]ureido}-3-(4-methoxyphenyl)-propionyl]piperidine-4-carboxylate 1-[(R)-2-(4-Butyryl-4-cyclohexylpiperidin-1-yl)-1-(4-methoxybenzyl)-2-oxoethyl]-3-[2-(1H-imidazol-4-yl)ethyl]urea 1-[(R)-2-(4-Butyryl-4-cyclohexylpiperidin-1-yl)-1-(4-fluorobenzyl)-2-oxoethyl]-3-[2-(1H-imidazol-4-yl)ethyl]urea 1-[(R)-1-Benzyl-2-(4-butyryl-4-cyclohexylpiperidin-1-yl)-2-oxoethyl]-3-[2-(1H-imidazol-4-yl)ethyl]urea 1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea 1-[(R)-2-(4-Butyryl-4-cyclohexylpiperidin-1-yl)-1-(4-methoxybenzyl)-2-oxoethyl]-3-[2-(1H-[1,2,3]triazol-4-yl)ethyl]urea 1-[(R)-2-(4-Butyryl-4-cyclohexylpiperidin-1-yl)-1-(4-chlorobenzyl)-2-oxoethyl]-3-[2-(1H-imidazol-4-yl)ethyl]urea Ethyl 4-cyclohexyl-1-((R)-3-(3,4-dichlorophenyl)-2-{3-[3-(1H-imidazol-4-yl)propyl]-ureido}propionyl)piperidine-4-carboxylate Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate Ethyl 4-cyclohexyl-1-[(R)-2-{3-[2-(1H-imidazol-4-yl)ethyl]thioureido}-3-(4-methoxy-phenyl)propionyl]piperidine-4-carboxylate and also the respective salts and enantiomers thereof.

According to the present invention, the compounds of general formula (I) that are particularly preferred are those for which:

R1 represents a cycloalkyl,
R2 represents a lower alkoxy, an acyl or an alkoxycarbonyl,
R3 represents an aralkyl or a substituted aralkyl,
R4 represents a heteroaralkyl,
R5 represents a hydrogen atom,
X represents an oxygen atom or a sulfur atom,
n, m is equal to 2; and also the corresponding salts and enantiomers.

The compounds that are particularly preferred are:

Ethyl 4-cyclohexyl-1-[2-{3-[2-(1H-imidazol-4-yl)ethyl]ureido}-3-(4-methoxyphenyl)-propionyl]piperidine-4-carboxylate Ethyl 4-cyclohexyl-1-(2-{3-[2-(1H-imidazol-4-yl)ethyl]ureido}-3-phenylpropionyl)-piperidine-4-carboxylate 1-[2-(4-Butyryl-4-cyclohexylpiperidin-1-yl)-1-(4-methoxybenzyl)-2-oxoethyl]-3-[2-(3H-imidazol-4-yl)ethyl]urea 1-[2-(4-Butoxy-4-cyclohexylpiperidin-1-yl)-1-(4-methoxybenzyl)-2-oxoethyl]-3-[2-(1H-imidazol-4-yl)ethyl]urea Methyl 4-cyclohexyl-1-[2-{3-[2-(1H-imidazol-4-yl)ethyl]ureido}-3-(4-methoxyphenyl)-propionyl]piperidine-4-carboxylate 1-[2-(4-Cyclohexyl-4-ethoxypiperidin-1-yl)-1-(4-methoxybenzyl)-2-oxoethyl]-3-[2-(1H-imidazol-4-yl)ethyl]urea 1-[2-(4-Acetyl-4-cyclohexylpiperidin-1-yl)-1-(4-methoxybenzyl)-2-oxoethyl]-3-[2-(1H-imidazol-4-yl)ethyl]urea 1-[2-(4-Cyclohexyl-4-propoxypiperidin-1-yl)-1-(4-methoxybenzyl)-2-oxoethyl]-3-[2-(1H-imidazol-4-yl)ethyl]urea Propyl 4-cyclohexyl-1-[2-{3-[2-(1H-imidazol-4-yl)ethyl]ureido}-3-(4-methoxyphenyl)-propionyl]piperidine-4-carboxylate Ethyl 1-((R)-3-(4-chlorophenyl)-2-{3-[2-(1H-imidazol-4-yl)ethyl]ureido}propionyl)-4-cyclohexylpiperidine-4-carboxylate 1-[2-(4-Cyclohexyl-4-propionylpiperidin-1-yl)-1-(4-methoxybenzyl)-2-oxoethyl]-3-[2-(1H-imidazol-4-yl)ethyl]urea Ethyl 4-cyclohexyl-1-[(R)-2-{3-[2-(1H-imidazol-4-yl)ethyl]ureido}-3-(4-methoxyphenyl)-propionyl]piperidine-4-carboxylate Propyl 4-cyclohexyl-1-(2-{3-[2-(1H-imidazol-4-yl)ethyl]ureido}-3-phenylpropionyl)-piperidine-4-carboxylate Ethyl 4-cyclopentyl-1-[2-{3-[2-(1H-imidazol-4-yl)ethyl]ureido}-3-(4-methoxyphenyl)-propionyl]piperidine-4-carboxylate Ethyl 4-cyclohexyl-1-[(S)-2-{3-[2-(1H-imidazol-4-yl)ethyl]ureido}-3-(4-methoxyphenyl)-propionyl]piperidine-4-carboxylate 1-[(R)-2-(4-Butyryl-4-cyclohexylpiperidin-1-yl)-1-(4-methoxybenzyl)-2-oxoethyl]-3-[2-(1H-imidazol-4-yl)ethyl]urea 1-[(R)-2-(4-Butyryl-4-cyclohexylpiperidin-1-yl)-1-(4-fluorobenzyl)-2-oxoethyl]-3-[2-(1H-imidazol-4-yl)ethyl]urea 1-[(R)-1-Benzyl-2-(4-butyryl-4-cyclohexylpiperidin-1-yl)-2-oxoethyl]-3-[2-(1H-imidazol-4-yl)ethyl]urea 1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea 1-[(R)-2-(4-Butyryl-4-cyclohexylpiperidin-1-yl)-1-(4-chlorobenzyl)-2-oxoethyl]-3-[2-(1H-imidazol-4-yl)ethyl]urea Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate Ethyl 4-cyclohexyl-1-[(R)-2-{3-[2-(1H-imidazol-4-yl)ethyl]thioureido}-3-(4-methoxy-phenyl)propionyl]piperidine-4-carboxylate and also the respective salts and enantiomers thereof.

According to the present invention, the compounds of general formula (I) that are particularly preferred are those for which:
R1 represents a cycloalkyl,
R2 represents an acyl or an alkoxycarbonyl,
R3 represents an aralkyl or a substituted aralkyl,
R4 represents a substituted or unsubstituted imidazole,
R5 represents a hydrogen atom,
X represents an oxygen atom or a sulfur atom,
n, m is equal to 2; and also the corresponding salts and enantiomers.

The compounds that are particularly preferred are:
Ethyl 4-cyclohexyl-1-[2-{3-[2-(1H-imidazol-4-yl)ethyl]ureido}-3-(4-methoxyphenyl)-propionyl]piperidine-4-carboxylate Ethyl 4-cyclohexyl-1-(2-{3-[2-(1H-imidazol-4-yl)ethyl]ureido}-3-phenylpropionyl)-piperidine-4-carboxylate 1-[2-(4-Butyryl-4-cyclohexylpiperidin-1-yl)-1-(4-methoxybenzyl)-2-oxoethyl]-3-[2-(3H-imidazol-4-yl)ethyl]urea Methyl 4-cyclohexyl-1-[2-{3-[2-(1H-imidazol-4-yl)ethyl]ureido}-3-(4-methoxyphenyl)-propionyl]piperidine-4-carboxylate 1-[2-(4-Acetyl-4-cyclohexylpiperidin-1-yl)-1-(4-methoxybenzyl)-2-oxoethyl]-3-[2-(1H-imidazol-4-yl)ethyl]urea Propyl 4-cyclohexyl-1-[2-{3-[2-(1H-imidazol-4-yl)ethyl]ureido}-3-(4-methoxyphenyl)-propionyl]piperidine-4-carboxylate Ethyl 1-((R)-3-(4-chlorophenyl)-2-{3-[2-(1H-imidazol-4-yl)ethyl]ureido}propionyl)-4-cyclohexylpiperidine-4-carboxylate 1-[2-(4-Cyclohexyl-4-propionylpiperidin-1-yl)-1-(4-methoxybenzyl)-2-oxoethyl]-3-[2-(1H-imidazol-4-yl)ethyl]urea Ethyl 4-cyclohexyl-1-[(R)-2-{3-[2-(1H-imidazol-4-yl)ethyl]ureido}-3-(4-methoxyphenyl)-propionyl]piperidine-4-carboxylate Propyl 4-cyclohexyl-1-(2-{3-[2-(1H-imidazol-4-yl)ethyl]ureido}-3-phenylpropionyl)-piperidine-4-carboxylate 1-[(R)-2-(4-Butyryl-4-cyclohexylpiperidin-1-yl)-1-(4-methoxybenzyl)-2-oxoethyl]-3-[2-(1H-imidazol-4-yl)ethyl]urea 1-[(R)-2-(4-Butyryl-4-cyclohexylpiperidin-1-yl)-1-(4-fluorobenzyl)-2-oxoethyl]-3-[2-(1H-imidazol-4-yl)ethyl]urea 1-[(R)-1-Benzyl-2-(4-butyryl-4-cyclohexylpiperidin-1-yl)-2-oxoethyl]-3-[2-(1H-imidazol-4-yl)ethyl]urea 1-[(R)-2-(4-Butyryl-4-cyclohexylpiperidin-1-yl)-1-(4-chlorobenzyl)-2-oxoethyl]-3-[2-(1H-imidazol-4-yl)ethyl]urea Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate Ethyl 4-cyclohexyl-1-[(R)-2-{3-[2-(1H-imidazol-4-yl)ethyl]thioureido}-3-(4-methoxy-phenyl)propionyl]piperidine-4-carboxylate and also the respective salts and enantiomers thereof.

The compounds according to the invention have modulatory properties on the melanocortin receptors. The expression "modulatory properties on the melanocortin receptors" means agonist or antagonist properties on the melanocortin receptors. This activity on the MCR receptors is measured in a transactivation test and quantified by the 50% effective concentration (EC 50), as described in Example 10.

Preferably, the compounds are at least modulators of the MCR receptors, and have properties suited to topical administration, i.e. they have a half-life of less than or equal to 10 minutes in human microsomes, they have a log D at pH 6.5 of greater than or equal to 3 and they are active topically in in vivo models.

Advantageously, the compounds of the present invention have a 50% effective concentration (EC50) with respect to the MC1 receptor of less than or equal to 10 μM and more particularly less than or equal to 1 μM.

The invention is thus directed towards the use of at least one compound of general formula (I) as defined above for the preparation of a pharmaceutical or cosmetic composition in which the said compound has modulatory activity on one or more melanocortin receptors and in particular on the subtypes 1, 3, 4 and 5.

In one particular mode of the invention, certain compounds of formula (I) in the present invention have activity on the MC1R receptor and are particularly useful for treating pigmentary disorders and inflammatory and immune disorders. Certain compounds of the invention have activity on the MC4R receptor and are particularly useful for treating eating behaviour and metabolism disorders and also neurodegenerative disorders.

The invention also relates to a therapeutic or cosmetic treatment method, comprising the administration of a pharmaceutical or cosmetic composition comprising the said compound, as modulator of one or more melanocortin receptors and in particular of the subtypes 1, 3, 4 and 5. In one particular mode, the invention also relates to a therapeutic or cosmetic method, comprising the administration of a pharmaceutical or cosmetic composition comprising the said compound, for treating pigmentary disorders and inflammatory and immune disorders. In one particular mode of the invention, the compounds are modulators of the subtype 1 and have properties suited to topical administration.

The invention also relates to the use of a compound of general formula (I) as defined above, and also to the corresponding salts and enantiomers thereof, for the preparation of a medicament for treating disorders associated with a dysfunction of the MC1 R receptor.

Finally, the compounds used according to the invention are particularly suitable for treating and/or preventing disorders and/or diseases such as inflammatory diseases:
of the digestive apparatus, especially including the intestine (and particularly the colon in the case of irritable bowel syndrome, ulcero-haemorrhagic rectocolitis or Crohn's disease); pancreatitis, hepatitis (acute and chronic), inflammatory bladder pathologies and gastritis;
of the locomotor apparatus, including rheumatoid arthritis, osteoarthritis, osteoporosis, traumatic arthritis, post-infection arthritis, muscular degeneration and dermatomyositis;
of the urogenital apparatus and especially glomerulonephritis;

of the cardiac apparatus and especially pericarditis and myocarditis and diseases including those for which inflammation is an underlying factor. These diseases include, but are not limited to, atherosclerosis, transplant atherosclerosis, peripheral vascular diseases, inflammatory vascular diseases, intermittent claudication or limping, restenosis, strokes, transient ischaemic attacks, myocardial ischaemia and myocardial infarction. These compounds may also be used for treating hypertension, hyperlipidaemia, coronary diseases, unstable angina (or angina pectoris), thrombosis, platelet aggregation induced by thrombin and/or the consequences of thrombosis and/or of the formation of atheroma plaques;

of the respiratory and ORL apparatus, especially including asthma, acute respiratory distress syndrome, hayfever, allergic rhinitis and chronic obstructive pulmonary disease. The compounds according to the invention may also be used for treating allergies;

of the central nervous system and especially Alzheimer's disease and any other form of dementia, Parkinson's disease, Creutzfeldt-Jakob disease, multiple sclerosis and meningitis;

of the skin, and especially urticaria, scleroderma, contact dermatitis, atopic dermatitis, psoriasis, ichthyosis, acne and other forms of folliculitis, rosacea and alopecia;

also immune diseases and especially lupus erythematosus, thyroid complaints, autoimmune diseases of the adrenal glands and autoimmune gastritis, vitiligo and alopecia areata;

inflammations accompanying bacterial, viral or fungal infections, especially tuberculosis, septicaemia, fever, HIV, irrespective of the location of the infection, herpes, cytomegalovirus, and hepatites A, B and C;

transplant or graft rejections, such as of the kidney, liver, heart, lung, pancreas, bone marrow, cornea, intestine or skin (skin allograft, homograft or heterograft, etc).

Furthermore, these compounds may be used for treating pain, irrespective of its origin: post-operative pain, neuromuscular pain, headaches, cancer-related pain, dental pain, osteoarticular pain.

These compounds may be used for modulating pigmentation, and, as a result, for:

treating diseases with pigmentation disorders and especially benign dermatoses such as vitiligo, albinism, melasma, lentigo, ephelides, melanocytic naevus and all post-inflammatory pigmentations; and also pigmented tumours such as melanomas and their local (permeation molecules), regional or systemic metastases;

antisun protection for the purpose of preventing:
the harmful effects of sunlight, such as actinic erythema, cutaneous ageing, skin cancer (spinocellular, basocellular and melanoma) and especially diseases that accelerate its occurrence (xeroderma pigmentosum, basocellular naevus syndrome and familial melanoma);

photodermatoses caused by exogenous photosensitizers and especially those caused by contact photosensitizers (for example furocoumarins, halogenated salicylanilides and derivatives, and local sulfamides and derivatives) or those caused by systemic photosensitizers (for example psoralenes, tetracyclines, sulfamides, phenothiazines, nalidixic acid and tricyclic antidepressants);

bouts of dermatosis with photosensitivity and especially light-aggravated dermatoses (for example lupus erythematosus, recurrent herpes, congenital poikilodermal or telangiectatic conditions with photosensitivity (Bloom's syndrome, Cockayne's syndrome or Rothmund-Thomson syndrome), actinic lichen planus, actinic granuloma, superficial disseminated actinic porokeratosis, acne rosacea, juvenile acne, bullous dermatosis, Darier's disease, lymphoma cutis, psoriasis, atopic dermatitis, contact eczema, follicular mucinosis, erythema multiforme, fixed drug eruption, cutaneous lymphocytoma, reticular erythematous mucinosis, and melasma);

dermatoses with photosensitivity by deficiency of the protective system with anomalies of melanin formation or distribution (for example oculocutaneous albinism, phenylketonuria, hypopituitarism, vitiligo and piebaldism) with deficiency of the DNA repair systems (for example xeroderma pigmentosum and Cockayne's syndrome), dermatoses with photosensitivity via metabolic anomalies, for instance cutaneous porphyria (for example tardive cutaneous porphyria, mixed porphyria, erythropoietic protoporphyria, congenital erythropoietic porphyria (Günther's disease), and erythropoietic coproporphyria), pellagra or pellagroid erythema (for example pellagra, pellagroid erythemas and tryptophan metabolism disorders);

bouts of idiopathic photodermatoses and especially PMLE (polymorphic light eruption), benign summer light eruption, actinic prurigo, persistent photosensitizations (actinic reticuloid, remanent photosensitizations and photosensitive eczema), solar urticaria, hydroa vacciniforme, juvenile spring eruption and solar pruritus);

modifying the colour of the skin or head hair and bodily hair, and especially by tanning the skin by increasing melanin synthesis or bleaching it by interfering with melanin synthesis, but also by preventing the bleaching or greying of head hair or bodily hair (for example canities and piebaldism);

modifying the colour of head hair and bodily hair in cosmetic indications.

These compounds may be useful for modifying the sebaceous function for:

treating hyperseborrhoea complaints and especially acne, seborrhoeic dermatitis, greasy skin and greasy hair, hyperseborrhoea in Parkinson's disease and epilepsy and hyperandrogenism;

treating complaints with reduction of sebaceous secretion and especially xerosis and all forms of dry skin;

regulating the benign or malignant proliferation of sebocytes and the sebaceous glands;

treating inflammatory complaints of the pilosebaceous follicles and especially acne, boils, carbuncles and folliculitis.

The invention also relates to the use of a compound of general formula (I) as defined above for the preparation of a medicament for treating disorders associated with a dysfunction of the MC4R receptor.

The compounds of the invention may also be used for treating neurodegenerative disorders, including depression, anxiety, compulsive disorders (such as compulsive obsessive disorders), neuroses, psychoses, insomnia and sleeping disorder, sleep apnoea, and drug abuse.

These compounds may be used for treating male or female sexual dysfunctions. The male sexual dysfunctions include, but are not limited to, impotence, loss of libido and erectile dysfunction.

The female sexual dysfunctions include, but are not limited to, sexual stimulation disorders or desire-related disorders, sexual receptivity, orgasm, and disturbances of the major points of sexual function. The female sexual dysfunctions may also include pain, premature labour, dysmenorrhoea, excessive menstruation, and endometriosis.

The compounds according to the invention may also be used for treating disorders related to weight but not limited to obesity and anorexia (such as modification or impairment of appetite, metabolism of the spleen, or the vocable irreproachable taking of fat or carbohydrates); diabetes mellitus (by tolerance to glucose doses and/or reduction of insulin resistance).

The compounds may also be used for treating cancer and in particular lung cancer, prostate cancer, bowel cancer, breast cancer, ovarian cancer, bone cancer or angiogenesis disorders including the formation or growth of solid tumours.

A subject of the present invention is also a pharmaceutical composition intended especially for treating the abovementioned complaints, which is characterized in that it comprises, in a pharmaceutically acceptable support that is compatible with the mode of administration selected therefor, a compound of general formula (I) in one of its tautomeric forms, or a salt thereof with a pharmaceutically acceptable acid.

The term "pharmaceutically acceptable support" means a medium that is compatible with the skin, mucous membranes and the integuments.

The administration of the composition according to the invention may be performed orally, enterally, parenterally, topically or ocularly. Preferably, the pharmaceutical composition is packaged in a form that is suitable for topical application.

Via the oral route, the composition may be in the form of tablets, gel capsules, coated tablets, syrups, suspensions, solutions, powders, granules, emulsions, suspensions, or microspheres, nanospheres or lipid or polymeric vesicles allowing controlled release. Via the parenteral route, the composition may be in the form of solutions or suspensions for perfusion or for injection.

The compounds according to the invention are generally administered at a daily dose from about 0.01 mg/kg to 100 mg/kg of body weight, in one or more dosage intakes.

The compounds are used systemically at a concentration generally of between 0.001% and 10% by weight and preferably between 0.01% and 5% by weight relative to the weight of the composition.

Via the topical route, the pharmaceutical composition according to the invention is more particularly intended for treating the skin and mucous membranes, and may be in liquid, pasty or solid form, and more particularly in the form of ointments, creams, milks, pomades, powders, impregnated pads, syndets, solutions, gels, sprays, mousses, suspensions, sticks, shampoos or washing bases. They may also be in the form of suspensions of microspheres or nanospheres or lipid or polymeric vesicles or of polymeric or gelled patches allowing controlled release.

The compositions used for topical application have a concentration of compound according to the invention generally of between 0.001% and 10% by weight and preferably between 0.01% and 5% by weight relative to the total weight of the composition.

The compounds of general formula (I) according to the invention also find an application in the cosmetic field, in particular in protecting against the harmful aspects of sunlight, for preventing and/or combating photoinduced or chronological ageing of the skin and the integuments.

A subject of the invention is thus also a composition comprising, in a cosmetically acceptable support, at least one of the compounds of general formula (I). The term "cosmetically acceptable medium" means a medium that is compatible with the skin, mucous membranes and the integuments.

A subject of the invention is also the cosmetic use of a composition comprising at least one compound of general formula (I), for preventing and/or treating the signs of ageing of the skin.

A subject of the invention is also the cosmetic use of a composition comprising at least one compound of general formula (I) for body or hair hygiene.

The cosmetic composition according to the invention containing, in a cosmetically acceptable support, a compound of general formula (I), or a tautomeric form thereof or a salt thereof with a pharmaceutically acceptable acid, may especially be in the form of a cream, a milk, a gel, suspensions of microspheres or nanospheres or lipid or polymeric vesicles, impregnated pads, solutions, sprays, mousses, sticks, soaps, washing bases or shampoos.

The concentration of compound of general formula (I) in the cosmetic composition is preferably between 0.001% and 10% by weight relative to the total weight of the composition.

The pharmaceutical and cosmetic compositions as described previously may also contain inert additives or even pharmacodynamically active additives as regards the pharmaceutical compositions, or combinations of these additives, and especially:

wetting agents;
flavour enhancers;
preserving agents such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase or ubiquinol;
emollients;
moisturizers such as glycerol, PEG-400, thiamorpholinone and derivatives thereof, or urea;
antiseborrhoeic or antiacne agents, such as S-carboxymethylcysteine, S-benzylcysteamine, salts thereof or derivatives thereof, or benzoyl peroxide.

Needless to say, a person skilled in the art will take care to select the optional compound(s) to be added to these compositions such that the advantageous properties intrinsically associated with the present invention are not, or are not substantially, adversely affected by the envisaged addition.

Several examples of production of compounds of general formula (I) according to the invention and of the results of biological activity of these compounds will now be given, by way of illustration and without any limiting nature.

The examples that follow describe the preparation of certain compounds in accordance with the invention. These examples are not limiting, and serve merely to illustrate the present invention. The numbers of the presented compounds refer to those given in the table hereinbelow, which illustrates the chemical structures and the physical properties of a number of compounds according to the invention.

The following abbreviations are used:
DMAP: dimethylaminopyridine
EDC: 1-Ethyl-(3-Dimethylaminopropyl)Carbodiimide hydrochloride HOBt: 1-HydrOxy-1,2,3-Benzotriazole
TBTU: N,N,N',N'-TetraMethyl-O-(BenzoTriazol-1-yl)Uronium Tetrafluoroborate
Fmoc: 6-FluorenylMethOxyCarbonyl
DBU: 1,5-DiazaBicyclo(5,4,0)Undec-5-ene
$NaBH_3CN$: Sodium cyanoborohydride
LiAlH4: Lithium aluminium hydride
$Rh/Al_2O_3$: Rhodium on alumina
$NaHCO_3$: Sodium hydrogen carbonate
$NH_4Cl$: Ammonium chloride
NaCl: Sodium chloride
$MgSO_4$: Magnesium sulfate
$Na_2SO_4$: Sodium sulfate
$CuSO_4$: Copper sulfate
NaOH: Sodium hydroxide
EtOAc: Ethyl acetate
DCM: DiChloroMethane
DMF: DiMethylFormamide
MeOH: Methanol
THF: Tetrahydrofuran
TLC: Thin Layer Chromatography
Materials and Methods:
Preparative HPLC Method:
  Modulo-cart strategy C18 100×21.2 mm, 5 μm column
  UV detector: 210-400 nm
  Flow rate: 17 mL/min
  Solvent A: $H_2O+0.05$ TFA
  Solvent B: $CH_3CN+0.05$ TFA
  Gradient:

| Time | composition |
| --- | --- |
| 0.0 min | A = 90%, B = 10% |
| 10.0 min | A = 2%, B = 98% |
| 12.0 min | A = 2%, B = 98% |
| 12.1 min | A = 90%, B = 10% |
| 15.0 min | A = 90%, B = 10% |

HPLC Methods:
Method A1
  Atlantis C18 150×2.1 mm, 3 μm column
  UV detector: 190-450 nm
  Flow rate: 0.3 mL/min
  Solvent A: $CH_3CN+0.1$ TFA
  Solvent B: $H_2O+0.1$ TFA
  Gradient:

| Time | composition |
| --- | --- |
| 0.0 min | A = 10%, B = 90% |
| 25.0 min | A = 90%, B = 10% |
| 30.0 min | A = 90%, B = 10% |

Method A
  Gemini 150×3 mm, 3 μm column
  UV detector: 190-450 nm
  Flow rate: 0.5 mL/min
  Solvent A: $CH_3CN+0.05$ TFA
  Solvent B: $H_2O+0.05$ TFA
  Gradient:

| Time | composition |
| --- | --- |
| 0.0 min | A = 5%, B = 95% |
| 5.0 min | A = 5%, B = 95% |
| 20.0 min | A = 95%, B = 5% |
| 30.0 min | A = 95%, B = 5% |

Method B
  Gemini 150×3 mm, 3 μm column
  UV detector: 190-450 nm
  Flow rate: 0.5 mL/min
  Solvent A: $CH_3CN+0.05$ TFA
  Solvent B: $H_2O+0.05$ TFA
  Gradient:

| Time | composition |
| --- | --- |
| 0.0 min | A = 5%, B = 95% |
| 20.0 min | A = 90%, B = 10% |
| 30.0 min | A = 90%, B = 10% |

Method C
  Gemini 150×3 mm, 3 μm column
  UV detector: 190-450 nm
  Flow rate: 0.5 mL/min
  Solvent A: $CH_3CN$
  Solvent B: $H_2O+0.02$ TFA
  Gradient:

| Time | composition |
| --- | --- |
| 0.0 min | A = 5%, B = 95% |
| 20.0 min | A = 90%, B = 10% |
| 30.0 min | A = 90%, B = 10% |

Method D
  Gemini 150×3 mm, 3 μm column
  UV detector: 190-450 nm
  Flow rate: 0.5 mL/min
  Solvent A: $CH_3CN$
  Solvent B: $H_2O+0.02$ TFA
  Gradient:

| Time | composition |
| --- | --- |
| 0.0 min | A = 10%, B = 90% |
| 15.0 min | A = 95%, B = 5% |
| 30.0 min | A = 95%, B = 5% |

Method E
  Column ?
  UV detector: 190-450 nm
  Flow rate: 0.5 mL/min
  Solvent A: MeOH+0.1 TFA
  Solvent B: $H_2O+0.02$ TFA
  Gradient:

| Time | composition |
| --- | --- |
| 0.0 min | A = 10%, B = 90% |
| 15.0 min | A = 95%, B = 5% |
| 30.0 min | A = 95%, B = 5% |

Method F
  Xbridge phenyl 250*4.6 mm 5 μm column
  UV detector: 190-450 nm
  Flow rate: 0.6 mL/min
  Solvent A: MeOH+25 mM NH$_4$OAc
  Solvent B: H$_2$O+25 mM NH$_4$OAc
  Gradient:

| Time | composition |
|---|---|
| 0.0 min | A = 50%, B = 50% |
| 15.0 min | A = 95%, B = 5% |
| 30.0 min | A = 95%, B = 5% |

Method G
  Xbridge phenyl 150*2.1 mm 3.5 μm column
  UV detector: 190-450 nm
  Flow rate: 1.0 mL/min
  Solvent A: MeOH 95%+H$_2$O 5%+25 mM NH$_4$OAc
  Solvent B: H$_2$O+25 mM NH$_4$OAc
  Gradient:

| Time | composition |
|---|---|
| 0.0 min | A = 5%, B = 95% |
| 20.0 min | A = 98%, B = 2% |
| 30.0 min | A = 98%, B = 2% |

Method I
  Gemini 150×3 mm, 3 μm column
  UV detector: 190-450 nm
  Flow rate: 0.5 mL/min
  Solvent A: CH$_3$CN+0.02 TFA
  Solvent B: H$_2$O+0.02 TFA
  Gradient:

| Time | composition |
|---|---|
| 0.0 min | A = 10%, B = 90% |
| 15.0 min | A = 90%, B = 10% |
| 30.0 min | A = 90%, B = 10% |

Method J
  Atlantis dC18 250×4.6 mm, 5 μm column
  UV detector: 190-450 nm
  Flow rate: 1.0 mL/min
  Solvent A: CH$_3$CN+0.02 TFA
  Solvent B: H$_2$O+0.02 TFA
  Gradient:

| Time | composition |
|---|---|
| 0.0 min | A = 2%, B = 98% |
| 5.0 min | A = 2%, B = 98% |
| 25.0 min | A = 90%, B = 10% |
| 30.0 min | A = 90%, B = 10% |

Method K
  Gemini C18 150×3 mm, 3 μm column
  UV detector: 190-450 nm
  Flow rate: 0.3 mL/min
  Solvent A: MeOH 94%+H$_2$O 6%+10 mM (NH$_4$)$_2$CO$_3$
  Solvent B: H$_2$O+10 mM (NH$_4$)$_2$CO$_3$
  Gradient:

| Time | composition |
|---|---|
| 0.0 min | A = 20%, B = 80% |
| 15.0 min | A = 95%, B = 5% |
| 30.0 min | A = 95%, B = 5% |

Method L
  Gemini C18 150×3 mm, 3 μm column
  UV detector: 190-450 nm
  Flow rate: 0.3 mL/min
  Solvent A: MeOH 94%+H$_2$O 6%+10 mM (NH$_4$)$_2$CO$_3$
  Solvent B: H$_2$O+10 mM (NH$_4$)$_2$CO$_3$
  Gradient:

| Time | composition |
|---|---|
| 0.0 min | A = 5%, B = 95% |
| 10.0 min | A = 95%, B = 5% |
| 30.0 min | A = 95%, B = 5% |

Method M
  Gemini C18 150×3 mm, 3 μm column
  UV detector: 190-450 nm
  Flow rate: 0.5 mL/min
  Solvent A: CH$_3$CN+0.05 TFA
  Solvent B: H$_2$O+0.05 TFA
  Gradient:

| Time | composition |
|---|---|
| 0.0 min | A = 10%, B = 90% |
| 15.0 min | A = 90%, B = 10% |
| 30.0 min | A = 90%, B = 10% |

Method N
  Gemini C18 150×3 mm, 3 μm column
  UV detector: 190-450 nm
  Flow rate: 0.5 mL/min
  Solvent A: CH$_3$CN+0.1% HCOOH
  Solvent B: H$_2$O+0.1% HCOOH
  Gradient:

| Time | composition |
|---|---|
| 0.0 min | A = 5%, B = 95% |
| 20.0 min | A = 95%, B = 5% |
| 30.0 min | A = 95%, B = 5% |

Method O
  Gemini C18 150×3 mm, 3 μm column
  UV detector: 190-450 nm
  Flow rate: 0.3 mL/min
  Solvent A: CH$_3$CN+0.05 TFA
  Solvent B: H$_2$O+0.05 TFA
  Gradient:

| Time | composition |
|---|---|
| 0.0 min | A = 5%, B = 95% |
| 5.0 min | A = 5%, B = 95% |
| 20.0 min | A = 85%, B = 15% |
| 30.0 min | A = 85%, B = 15% |

Method P
Phenomenex Gemini C6-Phenyl 150×3 mm, 3 μm column
UV detector: 190-450 nm
Flow rate: 0.5 mL/min
Solvent A: H$_2$O+0.05 TFA
Solvent B: CH$_3$CN+0.05 TFA
Gradient:

| Time | composition |
|---|---|
| 0.0 min | A = 95%, B = 5% |
| 20.0 min | A = 5%, B = 95% |
| 30.0 min | A = 5%, B = 95% |

Method Q
Gemini C18 150×3 mm, 3 μm column
UV detector: 190-450 nm
Flow rate: 0.5 mL/min
Solvent A: CH$_3$CN+0.1% HCOOH
Solvent B: H$_2$O+0.1% HCOOH
Gradient:

| Time | composition |
|---|---|
| 0.0 min | A = 5%, B = 95% |
| 10.0 min | A = 5%, B = 95% |
| 30.0 min | A = 70%, B = 30% |

Method R
Thermohypersil Hypurity C18 150×4.6 mm, 5 μm column
UV detector: 190-450 nm
Flow rate: 0.5 mL/min
Solvent A: H$_2$O+0.05 TFA
Solvent B: CH$_3$CN+0.05 TFA
Gradient:

| Time | composition |
|---|---|
| 0.0 min | A = 95%, B = 5% |
| 20.0 min | A = 5%, B = 95% |
| 30.0 min | A = 5%, B = 95% |

Method S
Atlantis T3 150×4.6 mm, 5 μm column
UV detector: 190-450 nm
Flow rate: 0.3 mL/min
Solvent A: H$_2$O+0.05 TFA
Solvent B: CH$_3$CN+0.05 TFA
Gradient:

| Time | composition |
|---|---|
| 0.0 min | A = 95%, B = 5% |
| 20.0 min | A = 5%, B = 95% |
| 30.0 min | A = 5%, B = 95% |

Method U
Atlantis T3 C18 150×2.1 mm, 3 μm column
UV detector: 190-900 nm
Flow rate: 0.3 mL/min
Solvent A: CH$_3$CN+0.02 TFA
Solvent B: H$_2$O+0.02 TFA
Gradient:

| Time | composition |
|---|---|
| 0.0 min | A = 5%, B = 95% |
| 20.0 min | A = 98%, B = 2% |
| 30.0 min | A = 98%, B = 2% |

EXAMPLE 1

1-[(S)-2-(4-Butyryl-4-phenylpiperidin-1-yl)-1-(4-methoxy-benzyl)-2-oxoethyl]-3-[2-(1H-imidazol-4-yl)ethyl]urea (Compound 1)

1-1 1-{1-[(S)-2-Amino-3-(4-methoxyphenyl)propionyl]-4-phenylpiperidin-4-yl}butan-1-one To a solution containing 11.9 g (28.5 mmol) of (S)-2-Fmoc-amino-3-(4-methoxy-phenyl)propionic acid dissolved in 120 mL of dichloromethane and 10 mL of dimethylformamide are added 5.51 g (38.9 mmol) of EDC and 5.25 g (38.9 mmol) of HOBt. After stirring for 30 minutes at room temperature, a solution of 6.95 g (26.1 mmol) of 1-(4-phenylpiperidin-4-yl)-butan-1-one hydrochloride and 18 mL of triethylamine in 150 mL of dichloromethane is added. The reaction medium is stirred for 2 hours, and saturated aqueous sodium hydrogen carbonate solution is then added. The organic compounds are extracted with dichloromethane. The organic phase is dried over magnesium sulfate and then filtered, and the solvents are evaporated off. The crude product is chromatographed on silica gel (eluent: 9/1 dichloromethane/methanol). 4.7 g of 1-{1-[(S)-2-amino-3-(4-methoxyphenyl)-propionyl]-4-phenylpiperidin-4-yl}butan-1-one in the form of an orange oil are obtained in a yield of 44%.

1-2 1-[(S)-2-(4-Butyryl-4-phenylpiperidin-1-yl)-1-(4-methoxybenzyl)-2-oxoethyl]-3-[2-(1H-imidazol-4-yl)ethyl]urea To a solution containing 100 mg (0.245 mmol) of 1-{1-[(S)-2-amino-3-(4-methoxy-phenyl)propionyl]-4-phenylpiperidin-4-yl}butan-1-one in 10 mL of dichloromethane are added 64 μL of diisopropylethylamine and then 74 mg (0.368 mmol) of 4-nitrophenyl chloroformate. The medium is stirred at room temperature for 1 hour 30 minutes. A solution containing 90 mg (0.489 mmol) of histamine dihydrochloride and 0.15 mL of diisopropylethylamine in 5 mL of dichloromethane and 2 mL of dimethylformamide is added to this mixture.

After stirring at room temperature for 3 hours, the solvents are evaporated off and the crude product obtained is purified by preparative HPLC (conditions cf. page 38). 37 mg of 1-[(S)-2-(4-butyryl-4-phenylpiperidin-1-yl)-1-(4-methoxy-benzyl)-2-oxoethyl]-3-[2-(1H-imidazol-4-yl)ethyl]urea trifluoroacetate in the form of a white powder are obtained in a yield of 37%.

HPLC: (method A1); retention time: 15.87 min, 98%, M+H: 545

EXAMPLE 2

1-[2-(4-Cyano-4-phenylpiperidin-1-yl)-1-(4-methoxybenzyl)-2-oxoethyl]-3-[2-(1H-imidazol-4-yl)ethyl]urea (Compound 3)

2-1 Methyl(S)-2-amino-3-(4-methoxyphenyl)propionate

To 10 g (33.8 mmol) of (S)-2-tert-butoxycarbonylamino-3-(4-methoxyphenyl)propionic acid are added 75 mL of methanol and then 10 mL of sulfuric acid dropwise over 30 minutes. After 30 hours, the reaction medium is basified to pH 8-9 by adding aqueous 10N sodium hydroxide solution followed by saturated sodium hydrogen carbonate solution. The organic products are extracted with dichloromethane. The organic phase is dried over magnesium sulfate and then filtered, and the solvents are evaporated off. 6.36 g of methyl (S)-2-amino-3-(4-methoxyphenyl)propionate in the form of a brown oil are obtained in a yield of 90%.

2-2 Methyl(S)-2-{3-[2-(1H-imidazol-4-yl)ethyl]ureido}-3-(4-methoxyphenyl)-propanoate To 5.08 g (24.3 mmol) of methyl(S)-2-amino-3-(4-methoxyphenyl)propionate are added 15 mL of dichloromethane. The reaction medium is immersed in a bath of cold water. 7.34 g (36.4 mmol) of 4-nitrophenyl chloroformate are added, followed by 6.33 mL of diisopropylethylamine. After warming to room temperature, the reaction medium is stirred for 2 hours. The reaction is stopped by adding water, followed by extraction with dichloromethane. The organic phase is dried over magnesium sulfate, filtered and concentrated on a rotary evaporator. 12 g of a yellow oil are obtained. To these 12 g are added 10 mL of dimethylformamide and the mixture is then heated to 80° C. 8.95 g (48.6 mmol) of histamine dihydrochloride are added, followed by dropwise addition of 14.8 mL (85.1 mmol) of diisopropylethylamine. After cooling to room temperature, the solvents are evaporated off and the crude product is chromatographed on silica gel (eluent: 85/15 dichloromethane/methanol). 5.6 g of methyl(S)-2-{3-[2-(1H-imidazol-4-yl)ethyl]ureido}-3-(4-methoxyphenyl)propanoate in the form of a yellow oil are obtained in a yield of 67%.

2-3 2-{3-[2-(1H-Imidazol-4-yl)ethyl]ureido}-3-(4-methoxyphenyl)propanoic acid

To 500 mg (1.44 mmol) of methyl(S)-2-{3-[2-(1H-imidazol-4-yl)ethyl]ureido}-3-(4-methoxyphenyl)propanoate are added 500 mg of lithium hydroxide, 7 mL of tetrahydrofuran and 2 mL of water. The reaction medium is placed in a microwave reactor with stirring, at 100° C. for 10 minutes. Seven other identical tests are performed. The various tests are combined and concentrated to dryness. The crude product obtained is purified by filtration on a pad of silica (eluent: 1/1 dichloromethane/methanol). 2.73 g of 2-{3-[2-(1H-imidazol-4-yl)ethyl]ureido}-3-(4-methoxyphenyl)propanoic acid in the form of a pale yellow powder are obtained in a yield of 70%.

2-4 1-[2-(4-Cyano-4-phenylpiperidin-1-yl)-1-(4-methoxybenzyl)-2-oxoethyl]-3-[2-(1H-imidazol-4-yl)ethyl]urea To 300 mg (0.90 mmol) of 2-{3-[2-(1H-imidazol-4-yl)ethyl]ureido}-3-(4-methoxy-phenyl)propanoic acid dissolved in 3.5 mL of dichloromethane and 1.5 mL of dimethylformamide are added 0.46 mL (2.7 mmol) of diisopropylethylamine, 318 mg (0.99 mmol) of TBTU and 220 mg (0.99 mmol) of 4-cyano-4-phenylpiperidine hydrochloride. After 16 hours, the solution is washed with saturated sodium hydrogen carbonate solution and the organic products are extracted with dichloromethane. The organic phase is dried over magnesium sulfate, filtered and concentrated. The crude product obtained is purified by filtration on a pad of silica (eluent: 7/3 dichloromethane/methanol). 75 mg of 1-[2-(4-cyano-4-phenylpiperidin-1-yl)-1-(4-methoxybenzyl)-2-oxoethyl]-3-[2-(1H-imidazol-4-yl)ethyl]urea in the form of a white powder are obtained in a yield of 17%.

$^1$H NMR/DMSO$_{D6}$ 100° C.: δ=1.92-2.13 (m, 2H); 2.62 (t, J=7.2 Hz, 2H); 2.72-2.99 (m, 8H); 3.26 (bq, J=5.6-7.2 Hz, 2H); 3.67 (s, 3H); 4.87 (bq, J=8.4 Hz, 1H); 5.95 (bt, 1H); 6.10 (d, J=8.4 Hz, 1H); 6.74 (s, 1H); 6.83 (d, J=8.8 Hz, 2H); 7.11-7.14 (m, 2H); 7.34-7.53 (m, 7H).

EXAMPLE 3

Ethyl 4-cyclohexyl-1-[2-{3-[2-(1H-imidazol-4-yl)ethyl]ureido}-3-(4-methoxyphenyl)propionyl]piperidine-4-carboxylate trifluoroacetate (Compound 6)

3-1-1 Ethyl piperidine-1-tert-butoxycarbonyl-4-cyclohexyl-4'-carboxylate

To 2.00 g (6.42 mmol) of piperidine-1-tert-butoxycarbonyl-4-cyclohexyl-4'-carboxylic acid in 10 mL of toluene are added 1.92 mL (12.8 mmol) of DBU and 1.04 mL (12.8 mmol) of iodoethane. The medium is stirred in a microwave reactor for 10 minutes at 120° C. Dichloromethane is added to the reaction medium and the organic phase is washed with saturated aqueous NaHCO$_3$ solution. The organic phase is dried over MgSO$_4$, filtered and concentrated. The crude product obtained is chromatographed on silica gel (eluent: 9/1 heptane/ethyl acetate). 1.92 g of ethyl piperidine-1-tertbutoxycarbonyl-4-cyclohexyl-4'-carboxylate in the form of a colourless oil are obtained in a yield of 88%.

3-1-2 Ethyl piperidine-4-cyclohexyl-4'-carboxylate

To 1.90 g (5.60 mmol) dissolved in 8 mL of dichloromethane are added, at 0° C., 6 mL of trifluoroacetic acid. After 4 hours, the solvents are evaporated off and the reaction medium is taken up in EtOAc and then washed with 1N sodium hydroxide. The organic phase is dried over MgSO$_4$, filtered and evaporated. 1.21 g of ethyl piperidine-4-cyclohexyl-4'-carboxylate in the form of a white powder are obtained in a yield of 90%.

3-2 Ethyl 4-cyclohexyl-1-[2-{3-[2-(1H-imidazol-4-yl)ethyl]ureido}-3-(4-methoxyphenyl)-propionyl]piperidine-4-carboxylate trifluoroacetate To 2.0 g (6.02 mmol) of 2-{3-[2-(1H-imidazol-4-yl)ethyl]ureido}-3-(4-methoxy-phenyl)propanoic acid (cf. preparation 2-3) dissolved in 90 mL of dimethylformamide are added 1.93 g (6.02 mmol) of TBTU, 2.1 mL (12.0 mmol) of diisopropylethylamine and 2.05 g (5.80 mmol) of ethyl piperidine-4-cyclohexyl-4'-carboxylate. After 6 hours, the solution is washed with 1N sodium hydroxide solution and the organic products are extracted with dichloromethane. The organic phase is dried over magnesium sulfate, filtered and concentrated. The crude product obtained is purified by preparative HPLC (conditions cf. page 74). 530 mg of 1-[2-(4-cyano-4-phenylpiperidin-1-yl)-1-(4-methoxybenzyl)-2-oxoethyl]-3-[2-(1H-imidazol-4-yl)ethyl]-urea trifluoroacetate in the form of a white powder are obtained in a yield of 14%.

$^1$H NMR/DMSO$_{D6}$ 100° C.: δ=0.87-0.90 (m, 2H); 1.07-1.37 (m, 13H); 1.57-1.64 (m, 3H); 1.72-1.75 (m, 2H), 1.92-1.96 (m, 2H); 2.66-2.82 (m, 4H); 3.29-3.35 (m, 2H); 3.74 (s, 3H); 4.13 (q, J=6.8-7.2 Hz, 2H); 4.80 (m, 1H); 6.00-6.10 (m, 2H); 6.82 (d, J=8.4 Hz, 2H); 7.07 (d, J=8.4 Hz, 2H); 7.30 (s, 1H); 8.80 (s, 1H).

EXAMPLE 4

1-[2-{3-[2-(1H-Imidazol-4-yl)ethyl]ureido}-3-(4-methoxy-phenyl)propionyl]-3-phenylazetidin-3-yl butyrate (Compound 8)

4-1-1
3-Hydroxy-3-phenylazetidine-1-tert-butoxycarbonyl

To a solution immersed in a bath at −50° C. containing 500 mg (2.92 mmol) of 3-oxo-azetidine-1-tert-butoxycarbonyl in 10 mL of THF are added dropwise 3.9 mL (11.7 mmol) of a 3M solution of phenylmagnesium bromide in diethyl ether. The medium is stirred for 1 hour at −50° C. and hydrolysed by addition of saturated ammonium chloride solution. After warming to room temperature, 1N hydrochloric acid solution is added, followed by extraction with ethyl acetate. The organic phase is dried and evaporated to dryness. The crude product obtained is chromatographed on silica gel (eluent: 7/3 heptane/ethyl acetate). 253 mg in the form of a white powder are obtained in a yield of 35%.

4-1-2 3-Butyryloxy-3-phenylazetidine-1-tert-butoxycarbonyl

To a solution containing 200 mg (0.80 mmol) of 3-hydroxy-3-phenylazetidine-1-tert-butoxycarbonyl in 4 mL of dichloromethane are added 98 mg (0.80 mmol) of DMAP and 0.13 mL of pyridine. After stirring at room temperature for 10 minutes, 0.26 mL of butyric anhydride is added. After 4 hours, saturated ammonium chloride solution is added, followed by extraction with dichloromethane. The organic phase is dried and evaporated to dryness. The crude product obtained is chromatographed on silica gel (eluent: 7/3 heptane/ethyl acetate). 186 mg in the form of an oil are obtained in a yield of 73%.

4-1-3 3-Phenylazetidin-3-yl trifluoroacetate butyrate

To a solution containing 183 mg (0.57 mmol) of 3-butyryloxy-3-phenylazetidine-1-tert-butoxycarbonyl dissolved in 8 mL of dichloromethane are added 2 mL of trifluoroacetic acid. The reaction medium is stirred at room temperature for 1 hour and then concentrated. The crude product obtained is chromatographed on silica gel (eluent: 90/10 dichloromethane/methanol). 88 mg in the form of a pale yellow oil are obtained in a yield of 46%.

4-2 1-[2-{3-[2-(1H-Imidazol-4-yl)ethyl]ureido}-3-(4-methoxyphenyl)propionyl]-3-phenylazetidin-3-yl butyrate To 80 mg (0.24 mmol) of 2-{3-[2-(1H-imidazol-4-yl)ethyl]ureido}-3-(4-methoxyphenyl)-propanoic acid (cf. preparation 2-3) dissolved in 2.75 mL of dichloromethane and 1.25 mL of dimethylformamide are added 0.08 mL (0.48 mmol) of diisopropylethylamine, 84 mg (0.26 mmol) of TBTU and 88 mg (0.26 mmol) of 3-phenylazetidin-3-yl butyrate trifluoroacetate. After 2 hours, the solution is washed with 1N sodium hydroxide solution and the organic products are extracted with dichloromethane. The organic phase is dried over magnesium sulfate, filtered and concentrated. The crude product obtained is chromatographed by preparative TLC (eluent: 9/1 dichloromethane/methanol). 5.4 mg of 1-[2-{3-[2-(1H-imidazol-4-yl)ethyl]-ureido}-3-(4-methoxyphenyl)propionyl]-3-phenylazetidin-3-yl butyrate are obtained in a yield of 2%.

HPLC: (method B); retention time: 12.15 min, 86%, M+H: 534.

EXAMPLE 5

1-[2-(3-Butoxy-3-phenylazetidin-1-yl)-1-(4-methoxybenzyl)-2-oxoethyl]-3-[2-(1H-imidazol-4-yl)ethyl]urea (Compound 11)

5-1-1
3-Hydroxy-3-phenylazetidine-1-tert-butoxycarbonyl

To a solution immersed in a bath at −50° C. containing 500 mg (2.92 mmol) of 3-oxo-azetidine-1-tert-butoxycarbonyl in 10 mL of THF are added dropwise 3.9 mL (11.7 mmol) of a 3M solution of phenylmagnesium bromide in diethyl ether. The medium is stirred for 1 hour at −50° C. and hydrolysed by addition of saturated ammonium chloride solution. After warming to room temperature, 1N hydrochloric acid solution is added, followed by extraction with ethyl acetate. The organic phase is dried and evaporated to dryness. The crude product obtained is chromatographed on silica gel (eluent: 7/3 heptane/ethyl acetate). 253 mg in the form of a white powder are obtained in a yield of 35%.

5-1-2
3-Butoxy-3-phenylazetidine-1-tert-butoxycarbonyl

To a suspension of 300 mg of 60% NaH in 3 mL of DMF immersed in a bath at 0° C. is added dropwise a solution of 1 g (4.0 mmol) of 3-hydroxy-3-phenylazetidine-1-tert-butoxycarbonyl dissolved in 5 mL of DMF. 2.5 mL of n-iodobutane are added dropwise. The reaction medium is stirred at 0° C. for 15 minutes and for 72 hours at room temperature. The medium is hydrolysed by adding saturated ammonium chloride solution, followed by extraction with ethyl acetate. The organic phase is dried and evaporated to dryness. The crude product obtained is chromatographed on silica gel (eluent: 7/3 heptane/ethyl acetate). 500 mg in the form of a pale yellow oil are obtained in a yield of 41%.

5-1-3 3-Butoxy-3-phenylazetidine trifluoroacetate

To a solution containing 500 mg (1.64 mmol) of 3-butoxy-3-phenylazetidine-1-tert-butoxycarbonyl dissolved in 5 mL of dichloromethane is added 1 mL of trifluoroacetic acid. The reaction medium is stirred at room temperature for 3 hours and then concentrated. The crude product obtained is chromatographed on silica gel (eluent: 90/10 dichloromethane/methanol). 400 mg in the form of a pale yellow powder are obtained in a yield of 76%.

5-2 1-[2-(3-Butoxy-3-phenylazetidin-1-yl)-1-(4-methoxybenzyl)-2-oxoethyl]-3-[2-(1H-imidazol-4-yl)ethyl]urea To 57 mg (0.17 mmol) of 2-{3-[2-(1H-imidazol-4-yl)ethyl]ureido}-3-(4-methoxyphenyl)-propanoic acid (cf. preparation 2-3) dissolved in 4 mL of dichloromethane and 1.5 mL of dimethylformamide are added 0.12 mL (0.68 mmol) of diisopropylethylamine, 61 mg (0.19 mmol) of TBTU and 55 mg (0.17 mmol) of 3-butoxy-3-phenylazetidine trifluoroacetate. After 3 hours, the solution is washed with 1N sodium hydroxide solution and the organic products are extracted with dichloromethane. The organic phase is dried over magnesium sulfate, filtered and concentrated. The crude product obtained is purified by preparative TLC (eluent: 9/1 dichloromethane/methanol). 3 mg of 1-[2-(3-butoxy-3-phenylazetidin-1-yl)-1-(4-methoxybenzyl)-2-oxoethyl]-3-[2-(1H-imidazol-4-yl)ethyl]urea are obtained in a yield of 3%.

HPLC: (method C); retention time: 11.6 min, 93%, M+H: 520.

EXAMPLE 6

Methyl 4-cyclohexyl-1-[2-{3-[2-(1H-imidazol-4-yl)ethyl]ureido}-3-(4-methoxyphenyl)propionyl]piperidine-4-carboxylamide (Compound 12)

6-1 4-Methylcarbamoyl-4-cyclohexylpiperidine

To 70 mg (0.22 mmol) of piperidine-1-tert-butoxycarbonyl-4-cyclohexyl-4'-methylcarbamoyl dissolved in 2 mL of dichloromethane is added, at 0° C., 1 mL of trifluoroacetic acid. After 1 hour, the solvents are evaporated off and the reaction medium is taken up in dichloromethane and washed with 1N sodium hydroxide. The organic phase is dried over $MgSO_4$, filtered and evaporated. 44 mg of 4-methylcarbamoyl-4-cyclohexylpiperidine in the form of a yellow oil are obtained in a yield of 90%.

6-2 Methyl 4-cyclohexyl-1-[2-{3-[2-(1H-imidazol-4-yl)ethyl]ureido}-3-(4-methoxy-phenyl)propionyl]piperidine-4-carboxylamide To 66 mg (0.20 mmol) of 2-{3-[2-(1H-imidazol-4-yl)ethyl]ureido}-3-(4-methoxyphenyl)-propanoic acid (cf. preparation 2-3) dissolved in 2 mL of dichloromethane and 0.5 mL of dimethylformamide are added 0.06 mL (0.40 mmol) of diisopropylethylamine, 71 mg (0.22 mmol) of TBTU and 44 mg (0.20 mmol) of 4-methylcarbamoyl-4-cyclohexylpiperidine. After 2 hours, the solution is washed with 1N sodium hydroxide solution and the organic products are extracted with dichloromethane. The organic phase is dried over magnesium sulfate, filtered and concentrated. The crude product obtained is purified by preparative TLC (eluent: 8/2 dichloromethane/methanol). 11 mg of methyl 4-cyclohexyl-1-[2-{3-[2-(1H-imidazol-4-yl)ethyl]ureido}-3-(4-methoxy-phenyl)propionyl]piperidine-4-carboxylamide in the form of a white powder are obtained in a yield of 10%.

HPLC: (method D); retention time: 11.82 min, 97%, M+H: 539.

EXAMPLE 7

1-[2-(3-Cyclohexanecarbonylazetidin-1-yl)-1-(4-methoxy-benzyl)-2-oxoethyl]-3-[2-(1H-imidazol-4-yl)ethyl]urea (Compound 13)

7-1-1 3-(Methoxymethylcarbamoyl)azetidine-1-tert-butoxycarbonyl 2 g (9.94 mmol) of 1-tert-butoxycarbonyl-3-azetidinecarboxylic acid are dissolved in 8 mL of dichloromethane, and 3.19 g (9.94 mmol) of TBTU and then 4 mL of dimethylformamide are added. 0.97 g (9.94 mmol) of N,O-dimethylhydroxylamine in 10 mL of dichloromethane and 5.17 mL (29.8 mmol) of diisopropylethylamine are added. After stirring for 2 hours, dichloromethane is added and the medium is washed with saturated $NaHCO_3$ solution and then with 5% citric acid solution. The organic phase is dried over $MgSO_4$, filtered and concentrated on a rotary evaporator. The crude product obtained is chromatographed on silica gel (eluent: 7/3 heptane/ethyl acetate). 1.9 g in the form of a colourless oil are obtained in a yield of 78%.

7-1-2 3-Cyclohexanecarbonylazetidine-1-tert-butoxycarbonyl

To 301 mg (1.23 mmol) of 3-(methoxymethylcarbamoyl)azetidine-1-tert-butoxycarbonyl in 5 mL of THF at 0° C. are added 1.48 mL (1.48 mmol) of a 1M solution of cyclohexylmagnesium bromide in THF. A further 3.35 mL (3.35 mmol) of magnesium reagent are necessary for the disappearance of the starting material. Dichloromethane is added, the organic phases are washed with saturated $NH_4Cl$ solution and then with saturated NaCl solution, and then dried over $MgSO_4$, filtered and concentrated. The crude product obtained is chromatographed on silica gel (eluent: 7/3 heptane/ethyl acetate). 205 mg in the form of a colourless oil are obtained in a yield of 62%.

7-1-3 3-Cyclohexanecarbonylazetidine

To a solution containing 192 mg (0.72 mmol) of 3-cyclohexanecarbonylazetidine-1-tert-butoxycarbonyl dissolved in 8 mL of dichloromethane are added 2 mL of trifluoroacetic acid. The reaction medium is stirred at room temperature for 2 hours and then concentrated. The reaction medium is extracted with dichloromethane in the presence of 1N sodium hydroxide solution. The organic phase is dried over $MgSO_4$, filtered and concentrated. 95 mg in the form of a white powder are obtained in a yield of 79%.

7-2 1-[2-(3-Cyclohexanecarbonylazetidin-1-yl)-1-(4-methoxybenzyl)-2-oxoethyl]-3-[2-(1H-imidazol-4-yl)ethyl]urea To 189 mg (0.57 mmol) of 2-{3-[2-(1H-imidazol-4-yl)ethyl]ureido}-3-(4-methoxy-phenyl)propanoic acid (cf. preparation 2-3) dissolved in 3.5 mL of dichloromethane and 1.0 mL of dimethylformamide are added 0.2 mL (1.14 mmol) of diisopropylethylamine, 202 mg (0.63 mmol) of TBTU and 95 mg (0.57 mmol) of 3-cyclohexanecarbonylazetidine. After 5 hours, the solution is washed with 1N sodium hydroxide solution and the organic products are extracted with dichloromethane. The organic phase is dried over magnesium sulfate, filtered and concentrated. The crude product obtained is purified by preparative TLC (9/1 dichloromethane/methanol). 8.5 mg of 1-[2-(3-cyclohexanecarbonylazetidin-1-yl)-1-(4-methoxybenzyl)-2-oxoethyl]-3-[2-(1H-imidazol-4-yl)ethyl]urea are obtained in a yield of 3%.

HPLC: (method E); retention time: 12.36 min, 86%, M+H: 482.

EXAMPLE 8

Ethyl 4-cyclohexyl-1-[2-{3-ethyl-3-[2-(1H-imidazol-4-yl)ethyl]-ureido}-3-(4-methoxyphenyl)propionyl]piperidine-4-carboxylate (Compound 14)

8-1-1 2,6,7,8-Tetrahydroimidazo[1,5-c]pyrimidin-5-one

To a suspension containing 500 mg (4.5 mmol) of histamine in 5 mL of acetonitrile are added 730 mg (4.5 mmol) of N,N'-carbonyldiimidazole and the mixture is heated at 80° C. for 16 hours. After cooling to room temperature, the solvent is evaporated off and 2.5 mL of ethanol are added. The product precipitates and is left stirring at 0° C. for 1 hour. The product is filtered off, rinsed with ice-cold ethanol and dried overnight in a vacuum oven. 370 mg of 2,6,7,8-tetrahydroimidazo[1,5-c]pyrimidin-5-one are obtained in a yield of 60%.

8-1-2 6-Ethyl-7,8-dihydro-6H-imidazo[1,5-c]pyrimidin-5-one

To 500 mg (3.6 mmol) of 5,6,7,8-tetrahydro-5-oxoimidazo [1,5-c]pyrimidine dissolved in 5 mL of DMF are added cautiously at room temperature 173 mg (4.32 mmol) of sodium hydride. The reaction medium is stirred for 1 hour at room temperature, and 0.35 mL (4.32 mmol) of iodoethane is then added dropwise. The reaction medium is stirred for 2 hours at room temperature and the solvents are then evaporated off. The residue is treated with 1N NaHCO₃ solution and extracted with chloroform. The combined organic phases are dried with MgSO₄, filtered and evaporated. The oil obtained is used directly in the following step.

8-1-3 Ethyl[2-(1H-imidazol-4-yl)ethyl]amine hydrochloride

To the crude product obtained from the preceding step is added aqueous potassium hydroxide solution (173 mg (6.16 mmol) in 5 mL of water) and the medium is refluxed for one hour. After cooling to room temperature, concentrated hydrochloric acid solution is added to pH 1. The water is evaporated off and the residue is taken up in ethanol. The ethanolic solution is heated to 80° C. and filtered while hot. The filtrate is evaporated. The solid obtained is then precipitated from a 1/1 ether/ethanol mixture and then filtered off under a nitrogen atmosphere. 160 mg of ethyl[2-(1H-imidazol-4-yl)ethyl]amine hydrochloride are obtained in a yield of 21% over the last two steps.

8-2 Methyl(S)-3-(4-methoxyphenyl)-2-(4-nitrophenoxycarbonylamino)propionate 1 g (4.8 mmol) of methyl(S)-2-amino-3-(4-methoxyphenyl)propionate (cf. preparation 2-1) is diluted in 30 mL of dichloromethane. The solution is cooled in a bath of cold water, and 1.4 g (7.2 mmol) of 4-nitrophenyl chloroformate and 1.2 mL (7.2 mmol) of diisopropylethylamine are then added. After warming to room temperature, the reaction medium is stirred for 2 hours. The solution is poured into water and then extracted with dichloromethane. The organic phase is dried and then evaporated. The crude product obtained is used in the following step without further purification.

8-3 Methyl(S)-2-{3-ethyl-3-[2-(1H-imidazol-4-yl)ethyl]ureido}-3-(4-methoxyphenyl)-propionate 0.14 g (0.38 mmol) of methyl(S)-3-(4-methoxyphenyl)-2-(4-nitrophenoxycarbonyl-amino)propionate is diluted in 2 mL of DMF. The solution is heated to 80° C. and 0.16 g (0.76 mmol) of ethyl[2-(1H-imidazol-4-yl)ethyl]amine hydrochloride and 0.13 mL (1.3 mmol) of diisopropylethylamine are then added. After 5 minutes, the reaction medium is cooled to room temperature and stirred for 15 minutes. Toluene is added and the solvents are evaporated off. The crude product obtained is chromatographed on silica gel (eluent: 8/2 dichloromethane/methanol). 0.15 g of methyl(S)-2-{3-ethyl-3-[2-(1H-imidazol-4-yl)ethyl]ureido}-3-(4-methoxyphenyl)-propionate in the form of a colourless oil is obtained in a yield of 100%.

8-4 2-{3-Ethyl-3-[2-(1H-imidazol-4-yl)ethyl]ureido}-3-(4-methoxyphenyl)propionic acid 150 mg (0.4 mmol) of methyl(S)-2-{3-ethyl-3-[2-(1H-imidazol-4-yl)ethyl]ureido}-3-(4-methoxyphenyl)propionate are diluted in 4 mL of THF and 1 mL of water, and 150 mg (6 mmol) of lithium hydroxide are added. The mixture is heated for 10 minutes at 100° C. in a microwave reactor. The solvents are evaporated off and the residue is then purified on a pad of silica (eluent: 1/1 dichloromethane/methanol). 100 mg of 2-{3-ethyl-3-[2-(1H-imidazol-4-yl)ethyl]ureido}-3-(4-methoxyphenyl)propionic acid in the form of a pale yellow powder are obtained in a yield of 69%.

8-5 Ethyl 4-cyclohexylpiperidine-4-carboxylate trifluoroacetate 0.34 g (1 mmol) of ethyl piperidine-1-tert-butoxycarbonyl-4-cyclohexyl-4'-carboxylate (cf. preparation 3-1-1) is dissolved in 4 mL of an 80/20 dichloromethane/trifluoroacetic acid mixture. The solution is stirred for 2 hours at room temperature and is then evaporated under nitrogen. 0.5 g in the form of a colourless oil is obtained and used in the following step without further purification.

8-6 Ethyl 4-cyclohexyl-1-[2-{3-ethyl-3-[2-(1H-imidazol-4-yl)ethyl]ureido}-3-(4-methoxy-phenyl)propionyl]piperidine-4-carboxylate 66 mg (0.19 mmol) of ethyl 4-cyclohexylpiperidine-4-carboxylate trifluoroacetate are diluted in 3 mL of dichloromethane and 3 mL of dimethylformamide, and 67 mg (0.21 mmol) of TBTU and 75 mg (0.21 mmol) of 2-{3-ethyl-3-[2-(1H-imidazol-4-yl)ethyl]ureido}-3-(4-methoxyphenyl)propionic acid and 0.06 mL (0.38 mmol) of diisopropylethylamine are added. After 2 hours of stirring at room temperature, aqueous 1N NaOH solution is added and the organic products are extracted with dichloromethane. The organic phase is dried and then evaporated. The crude product obtained is chromatographed on silica gel (eluent: 95/5 dichloromethane/methanol). 34 mg of ethyl 4-cyclohexyl-1-[2-{3-ethyl-3-[2-(1H-imidazol-4-yl)ethyl]ureido}-3-(4-methoxyphenyl)propionyl]piperidine-4-carboxylate in the form of a yellow oil are obtained in a yield of 30%.

HPLC: (method F); retention time: 20.72 min, 91%, M+H: 582.

EXAMPLE 9

N-Cyclopropyl-N-{1-[2-{3-[2-(1H-imidazol-4-yl)ethyl]ureido}-3-(4-methoxyphenyl)propionyl]piperidin-4-yl}propionamide (Compound 15)

9-1-1 tert-Butyl 4-cyclopropylaminopiperidine-1-carboxylate 1 g (5 mmol) of tert-butyl 4-oxopiperidine-1-carboxylate is dissolved in 40 mL of ethanol with 10% of acetic acid. 0.28 mL (4.2 mmol) of cyclopropylamine is added. After 30 minutes, 0.53 g (36 mmol) of NaBH₃CN is added and the reaction medium is stirred for one hour at room temperature. The reaction is stopped by addition of aqueous ammonia solution and the organic products are then extracted with ethyl acetate. The organic phase is dried and then evaporated. The crude product obtained is chromatographed on silica gel (eluent: 55/45 heptane/ethyl acetate). 0.8 g of tert-butyl 4-cyclopropylamino-piperidine-1-carboxylate in the form of a colourless oil is obtained in a yield of 79%.

9-1-2 tert-Butyl 4-(cyclopropylpropionylamino)piperidine-1-carboxylate 0.8 g (3.3 mmol) of tert-butyl 4-cyclopropylaminopiperidine-1-carboxylate, 0.48 mL (3.3 mmol) of triethylamine and 0.56 mL (3.3 mmol) of propionyl chloride are dissolved in 50 mL of THF. The reaction medium is stirred for 2 hours at room temperature. The reaction is stopped by adding water and the organic products are then extracted with dichloromethane. The organic phase is dried and then evaporated. The crude product obtained is chromatographed on silica gel (eluent: 6/4 heptane/ethyl acetate). 0.87 g of tert-butyl 4-(cyclopropylpropionylamino)piperidine-1-carboxylate in the form of a colourless oil is obtained in a yield of 89%.

9-1-3 N-Cyclopropyl-N-piperidin-4-ylpropionamide 0.87 g (2.9 mmol) of tert-butyl 4-(cyclopropylpropionylamino)piperidine-1-carboxylate is dissolved in 8 mL of an 80/20 DCM/MeOH mixture. The solution is stirred for 2 hours at room temperature and then poured into 1N NaOH solution and extracted with dichloromethane. The organic phase is dried over magnesium sulfate and then evaporated. 290 mg of crude product are obtained and used in the following step without further purification.

9-2 N-Cyclopropyl-N-{1-[2-{3-[2-(1H-imidazol-4-yl)ethyl]ureido}-3-(4-methoxyphenyl)-propionyl]piperidin-4-yl}propionamide 100 mg (0.51 mmol) of N-cyclopropyl-N-piperidin-4-ylpropionamide, 170 mg (0.51 mmol) of 2-{3-[2-(1H-imidazol-4-yl)ethyl]ureido}-3-(4-methoxyphenyl)propanoic acid (cf. preparation 2-3), 108 mg (0.56 mmol) of EDC and 76 mg (0.56 mmol) of HOBT are dissolved in 5 mL of DMF under nitrogen. The mixture is stirred at room temperature overnight, and the solution is then washed with aqueous 5% citric acid solution and extracted with ethyl acetate. The organic phase is washed with aqueous 1N NaOH solution and then dried and evaporated. The crude product obtained is purified by preparative HPLC (conditions cf. page 38). 2 mg of N-cyclopropyl-N-{1-[2-{3-[2-(1H-imidazol-4-yl)ethyl]ureido}-3-(4-methoxyphenyl)propionyl]piperidin-4-yl}-propionamide are obtained in a yield of 8%.

HPLC: (method G); retention time: 12.46 min, 92%, M+H: 511.

EXAMPLE 10

1-[-2-(4-Butyryl-4-cyclohexylpiperidin-1-yl)-1-(4-methoxy-benzyl)-2-oxoethyl]-3-[2-(1H-imidazol-4-yl)ethyl]urea trifluoroacetate (Compound 17)

10-1-1 4-Phenyl-1-(toluene-4-sulfonyl)piperidine-4-carbonitrile 17.2 g (89.8 mmol) of 4-methylbenzenesulfonyl chloride dissolved in 150 mL of dichloromethane are added to a solution of 20 g (89.8 mmol) of 4-phenylpiperidine-4-carbonitrile and 28 mL of triethylamine in 200 mL of dichloromethane. The reaction mixture is stirred for 1 hour at room temperature. The reaction is stopped by adding 200 mL of water, and is then extracted with dichloromethane. The organic phases are combined and dried over sodium sulfate. The solvents are evaporated off and the residue is then taken up in diethyl ether and filtered off. 30.3 g of 4-phenyl-1-(toluene-4-sulfonyl)piperidin-4-carbonitrile in the form of a white powder are obtained in a yield of 99%.

10-1-2 1-[4-Phenyl-1-(toluene-4-sulfonyl)piperidin-4-yl]-butan-1-one 88 mL (176 mmol) of n-propylmagnesium chloride are added to a solution of 30 g (88 mmol) of 4-phenyl-1-(toluene-4-sulfonyl)piperidine-4-carbonitrile in 500 mL of toluene. The reaction mixture is stirred for 6 hours at 65-70° C. and then overnight at room temperature. The reaction is stopped by adding 100 mL of tetrahydrofuran, and is then hydrolysed with 1N hydrochloric acid solution and extracted with ethyl acetate. The organic phases are combined and dried over sodium sulfate. The solvents are evaporated off and the residue is then taken up in diethyl ether and filtered off. 1.38 g of starting material are recovered. The filtrate is concentrated to dryness and then chromatographed on silica gel (eluent: 80/20 heptane/ethyl acetate). 17.8 g of 1-[4-phenyl-1-(toluene-4-sulfonyl)piperidin-4-yl]-butan-1-one in the form of a white powder are obtained in a yield of 50%.

10-1-3 4-Butyryl-4-phenylpiperidine hydrochloride 10 g (26 mmol) of 1-[4-phenyl-1-(toluene-4-sulfonyl)piperidin-4-yl]-butan-1-one are suspended in 64 mL of sulfuric acid and 32 mL of water. The reaction mixture is stirred at reflux for 48 hours. The reaction is monitored by HPLC. 50 mL of ethanol are added to homogenize the reaction medium, followed by 40 mL of sulfuric acid, and heating is continued for 24 hours. The reaction is stopped by addition to ice and basified with sodium hydroxide solution, and then extracted with ethyl acetate. The organic phases are combined and dried over sodium sulfate. The solvents are evaporated off and the residue is then taken up in diethyl ether and precipitated with a 4N solution of hydrogen chloride in ethyl acetate. 3.8 g of 4-butyryl-4-phenylpiperidine hydrochloride in the form of a white powder are obtained in a yield of 55%.

10-1-4 1-(4-Cyclohexylpiperidin-4-yl)butan-1-one

In a Parr bomb under a hydrogen pressure of 6 bar, 100 mg of rhodium on alumina and 0.2 mL of acetic acid are added to a solution of 100 mg (0.5 mmol) of 4-butyryl-4-phenylpiperidine hydrochloride in 10 mL of dioxane. The reaction medium is heated at 80° C. for 12 hours. The reaction is stopped and then filtered through Celite and washed with dichloromethane. The solvents are evaporated off and the residue is taken up in water, basified with 1N sodium hydroxide solution and extracted with ethyl acetate. The organic phases are dried over sodium sulfate. The solvents are evaporated off and the residue is chromatographed on silica gel (eluent: 9/1 dichloromethane/methanol). 51.2 mg of 1-(4-cyclohexylpiperidin-4-yl)-butan-1-one in the form of a white powder are obtained in a yield of 61%.

10-2 1-[2-(4-Butyryl-4-cyclohexylpiperidin-1-yl)-1-(4-methoxybenzyl)-2-oxoethyl]-3-[2-(1H-imidazol-4-yl)ethyl]urea trifluoroacetate 29 mg (0.22 mmol) of HOBt and 41 mg (0.22 mmol) of EDC are added to a solution of 62.5 mg (0.19 mmol) of 2-{3-[2-(1H-imidazol-4-yl)ethyl]ureido}-3-(4-methoxyphenyl)propanoic acid (cf. preparation 2-3) and 43.7 mg (0.19 mmol) of 1-(4-cyclohexylpiperidin-4-yl)butan-1-one in 2 mL of dimethylformamide. The reaction mixture is stirred for 16 hours at room temperature. The reaction is stopped by adding 10 mL of water, and is then extracted with ethyl acetate. The organic phases are combined and dried over sodium sulfate. The solvents are evaporated off and the residue is then purified by preparative HPLC (conditions cf. page 38). 63.7 mg of 1-[2-(4-butyryl-4-cyclohexylpiperidin-1-yl)-1-(4-methoxybenzyl)-2-oxoethyl]-3-[2-(1H-imidazol-4-yl)ethyl]urea trifluoroacetate in the form of a white foam are obtained in a yield of 59%.

HPLC: (method J); retention time: 21.49 min, 97%, M+H: 552.

EXAMPLE 11

1-[2-(4-Butoxy-4-cyclohexylpiperidin-1-yl)-1-(4-methoxy-benzyl)-2-oxoethyl]-3-[2-(1H-imidazol-4-yl)ethyl]urea (Compound 18)

11-1-1
4-Hydroxy-4-phenylpiperidine-1-tert-butoxycarbonyl 2.5 g (12.5 mmol) of tert-butyl 4-oxopiperidine-1-carboxylate are dissolved in 100 mL of THF and immersed in a bath at −50° C. 40 mL (40 mmol) of a phenylmagnesium bromide solution are added. After stirring for 1 hour 30 minutes, saturated $NH_4Cl$ solution is added and the reaction medium is then extracted with ethyl acetate. The organic phase is washed with 5% citric acid and then dried over $MgSO_4$, filtered and concentrated. The crude product obtained is chromatographed on silica gel (eluent: 7/3 heptane/ethyl acetate). 1.84 g in the form of a white powder are obtained in a yield of 53%.

11-1-2
4-Butoxy-4-phenylpiperidine-1-tert-butoxycarbonyl

A solution of 500 mg (1.80 mmol) of 4-hydroxy-4-phenylpiperidine-1-tert-butoxycarbonyl dissolved in 7.5 mL of DMF is immersed in a bath at 0° C., to which are added 196 mg (4.90 mmol) of 60% NaH and then 1 mL (8.7 mmol) of n-iodobutane. After stirring for 3 hours, a further 206 mg of 60% NaH and 1 mL of n-iodobutane are added. After 5 days, the reaction medium is extracted with ethyl acetate and washed with saturated $NH_4Cl$ solution. The organic phase is dried over $MgSO_4$, filtered and concentrated. The crude product obtained is chromatographed on silica gel (eluent: 9/1 heptane/ethyl acetate). 233 mg in the form of a colourless oil are obtained in a yield of 39%.

11-1-3 4-Butoxy-4-cyclohexylpiperidine-1-tert-butoxycarbonyl

A solution containing 178 mg of 5% $Rh/Al_2O_3$, 0.35 mL of acetic acid and 220 mg (0.66 mmol) of 4-butoxy-4-phenylpiperidine-1-tert-butoxycarbonyl in 18 mL of dioxane is placed under 6 bar of hydrogen at 80° C. for 18 hours. The reaction medium is filtered, washed with dichloromethane and concentrated. The crude product obtained is chromatographed on silica gel (eluent: 95/5 heptane/EtOAc). 139 mg in the form of a colourless oil are obtained in a yield of 62%.

11-1-4 4-Butoxy-4-cyclohexylpiperidine trifluoroacetate

To a solution containing 139 mg (0.41 mmol) of 4-butoxy-4-cyclohexylpiperidine-1-tert-butoxycarbonyl dissolved in 8 mL of dichloromethane are added 2 mL of trifluoroacetic acid. The reaction medium is stirred at room temperature for 2 hours and then concentrated. 241 mg in the form of a colourless oil are obtained and used in the following step without further purification.

11-2 1-[2-(4-Butoxy-4-cyclohexylpiperidin-1-yl)-1-(4-methoxybenzyl)-2-oxoethyl]-3-[2-(1H-imidazol-4-yl)ethyl]urea To 69 mg (0.21 mmol) of 2-{3-[2-(1H-imidazol-4-yl)ethyl]ureido}-3-(4-methoxyphenyl)-propanoic acid (cf. preparation 2-3) dissolved in 2 mL of DMF is added a solution of 71 mg (0.20 mmol) of 4-butoxy-4-cyclohexylpiperidine trifluoroacetate in 1.5 mL of DMF, 44 mg (0.23 mmol) of EDC and 33 mg (0.24 mmol) of HOBt. After 2 hours 30 minutes, the reaction medium is hydrolysed with aqueous 2% citric acid solution and then extracted with dichloromethane. The organic phase is then washed with aqueous 1N sodium hydroxide solution. The organic phase is dried over $MgSO_4$, filtered and concentrated. This oil is chromatographed on silica gel (eluent: 8/2 DCM/MeOH). 25 mg of 1-[2-(4-butoxy-4-cyclohexylpiperidin-1-yl)-1-(4-methoxy-benzyl)-2-oxoethyl]-3-[2-(1H-imidazol-4-yl)ethyl]urea are obtained in a yield of 22%.

$^1$H NMR/$DMSO_{D6}$ 100° C.: δ=0.87-0.94 (m, 4H); 1.06-1.23 (m, 5H); 1.33-1.68 (m, 12H); 1.72-1.80 (m, 3H); 2.63 (t, J=7.6 Hz, 2H); 2.71-2.83 (m, 4H); 2.91-3.09 (m, 2H); 3.19-3.28 (m, 4H); 3.73 (s, 3H); 4.84 (bq, J=6.4-8.4 Hz, 1H); 5.96-6.02 (m, 2H); 6.79 (d, J=5.6 Hz, 2H); 6.82 (s, 1H); 7.08 (d, J=8.0 Hz, 2H); 7.58 (s, 1H).

EXAMPLE 12

Ethyl 4-ethyl-1-[2-{3-[2-(1H-imidazol-4-yl)ethyl]ureido}-3-(4-methoxyphenyl)propionyl]piperidine-4-carboxylate (Compound 24)

12-1-1 tert-Butyl 4-ethyl-4-ethoxycarbonylpiperidine-1-carboxylate 0.2 g (0.78 mmol) of tert-butyl 4-ethoxycarbonylpiperidine-1-carboxylate is dissolved in 4 mL of THF at −10° C. 0.8 mL (1.56 mmol) of lithium diisopropylamide is added dropwise. After 15 minutes, 0.09 mL (1.2 mmol) of iodoethane is added and the mixture is warmed to room temperature. It is stirred for 30 minutes and then poured into saturated ammonium chloride solution and extracted with ethyl acetate. The organic phase is dried and then concentrated to dryness. The oil obtained is chromatographed on silica gel (eluent: 95/5 heptane/ethyl acetate). 183 mg of tert-butyl 4-ethyl-4-ethoxycarbonylpiperidine-1-carboxylate in the form of a yellow oil are obtained in a yield of 82%.

12-1-2 4-Ethoxycarbonyl-4-ethylpiperidine trifluoroacetate 183 mg (0.64 mmol) of tert-butyl 4-ethyl-4-ethoxycarbonylpiperidine-1-carboxylate are diluted in 4 mL of an 8/2 dichloromethane/trifluoroacetic acid mixture. The solution is stirred at room temperature for 1 hour and the solvents are then evaporated off. 140 mg of 4-ethoxycarbonyl-4-ethylpiperidine trifluoroacetate in the form of an oil are obtained in a yield of 73%.

12-2 Ethyl 4-ethyl-1-[2-{3-[2-(1H-imidazol-4-yl)ethyl]ureido}-3-(4-methoxyphenyl)-propionyl]piperidine-4-carboxylate 0.194 g (0.59 mmol) of 2-{3-[2-(1H-imidazol-4-yl)ethyl]ureido}-3-(4-methoxyphenyl)-propanoic acid (cf. preparation 2-3), 140 mg (0.47 mmol) of 4-ethoxycarbonyl-4-ethylpiperidine trifluoroacetate, 124 mg (0.65 mmol) of EDC and 88 mg (0.65 mmol) of HOBt are dissolved in 4 mL of DMF. The mixture is stirred at room temperature for 72 hours. The reaction medium is washed with aqueous 1N NaOH solution and then extracted with dichloromethane. The organic phase is dried and evaporated.

The oil obtained is chromatographed on silica gel (eluent: 90/10 DCM/MeOH). 89 mg of ethyl 4-ethyl-1-[2-{3-[2-(1H-imidazol-4-yl)ethyl]ureido}-3-(4-methoxyphenyl)-propionyl]piperidine-4-carboxylate in the form of a colourless oil are obtained in a yield of 30%.

HPLC: (method M); retention time: 9.32 min, 93%, M+H: 500.

EXAMPLE 13

Cyclohexyl-1-[2-{3-[2-(1H-imidazol-4-yl)ethyl]ureido}-3-(4-methoxyphenyl)propionyl]piperidine-4-carboxylic acid trifluoroacetate (Compound 26)

13-1 4-Cyclohexylpiperidine-4-carboxylic acid trifluoroacetate

To a solution containing 480 mg (1.54 mmol) of piperidine-1-tert-butoxycarbonyl-4-cyclohexyl-4'-carboxylic acid dissolved in 3 mL of dichloromethane is added at room temperature 1 mL of trifluoroacetic acid. After evaporating off the solvents, the oil obtained is used in the following step.

13-2 Cyclohexyl-1-[2-{3-[2-(1H-imidazol-4-yl)ethyl]ureido}-3-(4-methoxyphenyl)-propionyl]piperidine-4-carboxylic acid trifluoroacetate To a solution containing 93 mg (0.28 mmol) of 2-{3-[2-(1H-imidazol-4-yl)ethyl]ureido}-3-(4-methoxyphenyl)propanoic acid and 100 mg (0.31 mmol) of 4-cyclohexyl-piperidine-4-carboxylic acid trifluoroacetate in 0.8 mL of dimethylformamide are added 0.16 mL of diisopropylethylamine and 90 mg (0.28 mmol) of TBTU. The reaction medium is stirred at room temperature for 18 hours. The reaction is stopped by adding water, and the organic compounds are extracted with dichloromethane. The organic phase is dried and evaporated. The oil obtained is purified by preparative HPLC (conditions cf. page 38). 35 mg of cyclohexyl-1-[2-{3-[2-(1H-imidazol-4-yl)ethyl]ureido}-3-(4-methoxyphenyl)propionyl]piperidine-4-carboxylic acid trifluoroacetate are obtained in a yield of 19%.

HPLC: (method L); retention time: 14.75 min, 96%, M+H: 526.

EXAMPLE 14

1-[2-(1H-Imidazol-4-yl)ethyl]-3-{1-(4-methoxybenzyl)-2-[3-(2-methylcyclohexyl)-3-propoxyazetidin-1-yl]-2-oxoethyl}urea trifluoroacetate (Compound 27)

14-1-1 tert-Butyl 3-(2-methylcyclohexyl)-3-propoxyazetidine-1-carboxylate 170 mg (0.56 mmol) of tert-butyl 3-(2-methylcyclohexyl)-3-propoxyazetidine-1-carboxylate prepared as described in Example 6-1-2, 48 mg of 5% rhodium on alumina, 5 mL of methanol and 0.6 mL of acetic acid are introduced into a Parr bomb. The medium is stirred under 4 bar of hydrogen at 90° C. for 7 days. The reaction medium is filtered and rinsed with dichloromethane, and then concentrated to dryness. The crude product is chromatographed on silica gel (eluent: 95/5 heptane/ethyl acetate). 96 mg of tert-butyl 3-(2-methylcyclohexyl)-3-propoxy-azetidine-1-carboxylate in the form of a colourless oil are obtained in a yield of 55%.

14-1-2 3-(2-Methylcyclohexyl)-3-propoxyazetidine trifluoroacetate 91 mg (0.29 mmol) of tert-butyl 3-(2-methylcyclohexyl)-3-propoxyazetidine-1-carboxylate are dissolved in 8 mL of dichloromethane. The reaction medium is immersed in an ice bath. 2 mL of trifluoroacetic acid are added. After 1 hour, the solvents are evaporated off. 113 mg in the form of a brown oil are used in the following step without further purification.

14-2 1-[2-(1H-Imidazol-4-yl)ethyl]-3-{1-(4-methoxybenzyl)-2-[3-(2-methylcyclohexyl)-3-propoxyazetidin-1-yl]-2-oxoethyl}urea trifluoroacetate To 97 mg (0.29 mmol) of 2-{3-[2-(1H-imidazol-4-yl)ethyl]ureido}-3-(4-methoxyphenyl)-propanoic acid (cf. preparation 2-3) dissolved in 2 mL of DMF are added 94 mg (0.29 mmol) of 3-(2-methylcyclohexyl)-3-propoxyazetidine trifluoroacetate, 70 mg (0.37 mmol) of EDC and 45 mg (0.33 mmol) of HOBt. After 3 hours, the reaction medium is hydrolysed with aqueous 1N sodium hydroxide solution and then extracted with dichloromethane. The organic phase is dried over MgSO$_4$, filtered and concentrated. The crude product obtained is purified by preparative HPLC. 33 mg of 1-[2-(1H-imidazol-4-yl)ethyl]-3-{1-(4-methoxybenzyl)-2-[3-(2-methylcyclohexyl)-3-propoxyazetidin-1-yl]-2-oxoethyl}urea trifluoroacetate are obtained in a yield of 18%.

$^1$H NMR/DMSO$_{D6}$ 100° C.: δ=0.79-0.86 (m, 3H); 0.88-0.95 (m, 3H); 1.10-1.30 (m, 2H); 1.40-1.50 (m, 8H); 1.63-1.73 (m, 2H); 1.98-2.05 (m, 1H); 2.78 (bq, J=6.8-8.8 Hz, 5H); 3.22-3.38 (m, 2H); 3.56-3.70 (m, 3H); 3.75 (s, 3H); 3.80-4.20 (m, 1H); 4.34 (bt, J=7.2 Hz, 1H); 5.90-6.20 (m, 2H); 6.85 (bd, 2H); 7.10 (d, J=8.0 Hz, 2H); 7.31 (s, 1H); 8.82 (s, 1H).

EXAMPLE 15

1-[2-(1H-Imidazol-4-yl)ethyl]-3-[1-(4-methoxybenzyl)-2-oxo-2-(3-pentyl-3-phenylazetidin-1-yl)ethyl]urea (Compound 29)

15-1-1 2-Phenylheptanenitrile

To a suspension of 2 g of 60% NaH in 50 mL of DMF cooled to 0° C. are added dropwise 5 g (42.7 mmol) of phenylacetonitrile. After stirring for 30 minutes at 0° C., 5.32 mL (42.7 mmol) of bromopentane are added dropwise. The reaction medium is stirred for 16 hours at room temperature and then treated with ice and extracted with ethyl ether. The organic phase is washed with saturated aqueous sodium hydrogen carbonate solution, dried over sodium sulfate, filtered and evaporated under pressure. An orange-yellow oil is obtained and purified by fractional distillation under reduced pressure (70-75° C. at 1×10$^{-1}$ mbar). 5.14 g in the form of an orange-coloured oil are obtained in a yield of 64%.

15-1-2 2-Hydroxymethyl-2-phenylheptanenitrile

To a suspension of 1.34 g of 60% NaH in 50 mL of DMF cooled to 0° C. are added 5.14 g (27.4 mmol) of 2-phenylheptanenitrile. After stirring for 30 minutes, 7.6 g (220 mmol) of paraformaldehyde are added portionwise. The reaction medium is stirred at room temperature for 6 hours and then hydrolysed with ice and extracted with diethyl ether. The organic phase is washed with saturated aqueous sodium hydrogen carbonate solution, dried over sodium sulfate, filtered and evaporated under pressure. The crude product obtained is chromatographed on silica gel (eluent: 8/2 heptane/ethyl acetate). 4.24 g in the form of a pale yellow oil are obtained in a yield of 71%.

15-1-3 Toluene-4-sulfonic acid 2-cyano-2-phenylheptyl ester

To a solution containing 4.24 g (19.5 mmol) of 2-hydroxymethyl-2-phenyl-heptanenitrile in 25 mL of dichloromethane are added 4.1 g (21.5 mmol) of p-toluenesulfonyl chloride and 6 mL of triethylamine. The reaction medium is stirred for 15 hours at room temperature and then treated with 1N hydrochloric acid solution and extracted with dichloromethane. The organic phase is dried over sodium sulfate, filtered and evaporated under pressure. A yellow oil is obtained and precipitated from a 9/1 heptane/diisopropyl ether mixture. The precipitate formed is filtered off and rinsed with diisopropyl ether. 5.26 g in the form of a beige-coloured powder are obtained in a yield of 72%.

15-1-4 3-Pentyl-3-phenylazetidine

To a solution containing 5.26 g (14.1 mmol) of toluene-4-sulfonic acid 2-cyano-2-phenylheptyl ester in 25 mL of THF under nitrogen are added cautiously 600 mg (15.5 mmol) of LiAlH$_4$ powder. The reaction medium is stirred for 1 hour at room temperature and then treated with a sodium sulfate paste (hot water+Na$_2$SO$_4$). After stirring for 30 minutes at room temperature, the salts formed are filtered off and the filtrate is evaporated under reduced pressure. The residue is taken up in dichloromethane and washed with aqueous 1N sodium hydroxide solution. The organic phase is dried over sodium sulfate, filtered and evaporated under reduced pressure. 2.90 g of a colourless oil are obtained and used in the following step without further purification.

15-2 1-[2-(1H-Imidazol-4-yl)ethyl]-3-[1-(4-methoxybenzyl)-2-oxo-2-(3-pentyl-3-phenyl-azetidin-1-yl)ethyl]urea 170 mg (0.837 mmol) of 3-pentyl-3-phenylazetidine are dissolved in 2 mL of DMF with 50 mg of 2-{3-[2-(1H-imidazol-4-yl)ethyl]ureido}-3-(4-methoxyphenyl)propanoic acid (cf. preparation 2-3). To this solution are added 177 mg (0.920 mmol) of EDC and then 125 mg (0.920 mmol) of HOBt. The reaction medium is stirred for 4 hours and then treated with 1N sodium hydroxide and extracted with dichloromethane. The combined organic phases are dried over Na$_2$SO$_4$, filtered and evaporated. The crude product obtained is chromatographed on silica gel (eluent: 90/10 DCM/methanol).

180 mg of 1-[2-(1H-imidazol-4-yl)ethyl]-3-[1-(4-methoxybenzyl)-2-oxo-2-(3-pentyl-3-phenylazetidin-1-yl)ethyl]urea in the form of a white powder are obtained in a yield of 41%.

$^1$H NMR/DMSO$_{D6}$ 100° C.: δ=7.45 (s, 1H); 7.30 (m, 3H); 7.22 (m, 1H); 7.19 (m, 4H); 6.82 (m, 2H); 6.72 (s, 1H); 5.99 (d, J=9.2 Hz, 1H); 5.90 (m, 1H); 4.38 (q, J=7.2 Hz, 1H); 3.73 (m, 4H); 3.23 (m, 2H); 2.93 (m, 3H); 2.75 (d, J=6 Hz, 2H); 2.61 (t, J=6.80 Hz, 2H); 1.18 (m, 4H); 0.98 (m, 2H); 0.78 (t, J=6.4 Hz, 3H).

EXAMPLE 16

Ethyl 1-((R)-3-(4-chlorophenyl)-2-{3-[2-(1H-imidazol-4-yl)ethyl]ureido}propionyl)-4-cyclohexylpiperidine-4-carboxylate (Compound 30)

16-1 Ethyl 1-[(R)-2-tert-butoxycarbonylamino-3-(4-chlorophenyl)propionyl]-4-cyclohexylpiperidine-4-carboxylate 3.1 g (10 mmol) of (R)-2-tert-butoxycarbonylamino-3-(4-chlorophenyl)propionic acid, 1.9 g (11 mmol) of EDC, 1.5 g (11 mmol) of HOBt and 1.7 mL (20 mmol) of diisopropylethylamine are dissolved in 80 mL of DMF. The mixture is stirred at room temperature for 15 minutes, and 2.6 g (10 mmol) of ethyl piperidine-4-cyclohexyl-4'-carboxylate (cf. preparation 9-2) diluted in 20 mL of DMF are then added. After stirring for 2 hours, a further 1.7 mL (20 mmol) of diisopropylethylamine are added. The reaction is stopped by adding aqueous 5% citric acid solution. The organic products are extracted with ethyl acetate and the organic phase is washed with aqueous 1N NaOH solution. The organic phase is dried and evaporated. 5.2 g of ethyl 1-[(R)-2-tert-butoxycarbonylamino-3-(4-chlorophenyl)propionyl]-4-cyclohexylpiperidine-4-carboxylate in the form of a colourless oil are obtained in a yield of 75%.

16-2 Ethyl 1-[(R)-2-amino-3-(4-chlorophenyl)propionyl]-4-cyclohexylpiperidine-4-carboxylate 0.26 g (0.5 mmol) of ethyl 1-[(R)-2-tert-butoxycarbonylamino-3-(4-chlorophenyl)-propionyl]-4-cyclohexylpiperidine-4-carboxylate is diluted in 4 mL of DCM and 1 mL of trifluoroacetic acid, and the solution is stirred for 2 hours at room temperature and then quenched by adding aqueous 1N NaOH solution and extracted with dichloromethane. The organic phase is dried and then evaporated. 200 mg of ethyl 1-[(R)-2-amino-3-(4-chlorophenyl)propionyl]-4-cyclohexylpiperidine-4-carboxylate in the form of a colourless oil are obtained in a yield of 95%.

16-3 Ethyl 1-((R)-3-(4-chlorophenyl)-2-{3-[2-(1H-imidazol-4-yl)ethyl]ureido}propionyl)-4-cyclohexylpiperidine-4-carboxylate 200 mg (0.48 mmol) of ethyl 1-[(R)-2-amino-3-(4-chlorophenyl)propionyl]-4-cyclohexylpiperidine-4-carboxylate and 105 mg (0.52 mmol) of para-nitrophenyl chloroformate are dissolved in 5 mL of dichloromethane. The mixture is stirred for 2 hours at room temperature and the solution is then poured into aqueous 20% NH$_4$OH solution and extracted with dichloromethane. The organic phase is washed with water and then dried over sodium sulfate and evaporated. The colourless oil obtained is diluted in 5 mL of DMF, the mixture is heated to 80° C., 58 mg (0.52 mmol) of histamine are then added and the solution is stirred for 5 minutes at 80° C. and for 10 minutes at room temperature. The reaction is stopped by adding aqueous 5% citric acid solution, and the organic products are extracted with DCM. The organic phase is washed with aqueous 1N NaOH solution and then with water. After drying over sodium sulfate and evaporation, the crude product obtained is chromatographed on silica gel (eluent: 80/20 DCM/MeOH). 40 mg of ethyl 1-((R)-3-(4-chlorophenyl)-2-

{3-[2-(1H-imidazol-4-yl)ethyl]ureido}propionyl)-4-cyclohexylpiperidine-4-carboxylate in the form of a colourless oil are obtained in a yield of 15%.

HPLC: (method N); retention time: 11.01 min, 96%, M+H: 558.

EXAMPLE 17

1-[2-(4-Acetyl-4-cyclohexylpiperidin-1-yl)-1-(4-methoxy-benzyl)-2-oxoethyl]-3-(1H-imidazol-4-ylmethyl)urea trifluoroacetate (Compound 32)

17-1-1 1-[4-Phenyl-1-(toluene-4-sulfonyl)piperidin-4-yl]propan-1-one 3.9 mL (2.94 mmol) of a 3M solution of ethylmagnesium bromide are added to a solution of 2 g (5.9 mmol) of 4-phenyl-1-(toluene-4-sulfonyl)piperidine-4-carbonitrile in 40 mL of toluene. The reaction mixture is stirred overnight at 65-70° C. The reaction is stopped and hydrolysed with 1N hydrochloric acid solution, and then extracted with ethyl acetate. The organic phases are combined and dried over sodium sulfate. The solvents are evaporated off and the residue is then taken up in ethyl acetate, to which is added 1N hydrochloric acid solution, and the mixture is stirred at room temperature for 72 hours. 2.16 g of 1-[4-phenyl-1-(toluene-4-sulfonyl)-piperidin-4-yl]propan-1-one in the form of a yellow oil are obtained in a yield of 99%.

17-1-2 1-(4-Phenylpiperidin-4-yl)propan-1-one hydrochloride 2.1 g (5.6 mmol) of 1-[4-phenyl-1-(toluene-4-sulfonyl)piperidin-4-yl]propan-1-one are suspended in 14 mL of sulfuric acid and 7 mL of water. The reaction mixture is stirred at reflux for 72 hours. The reaction is stopped by addition to ice, and basified with sodium hydroxide solution and then extracted with ethyl acetate. The organic phases are combined and dried over sodium sulfate. The solvents are evaporated off and the residue is then taken up in diethyl ether and precipitated with a 4N solution of hydrogen chloride in ethyl acetate. 1.04 g of 1-(4-phenylpiperidin-4-yl)propan-1-one hydrochloride in the form of a beige-coloured powder are obtained in a yield of 73%.

17-1-3 tert-Butyl 4-phenyl-4-propionylpiperidine-1-carboxylate 470 mg (2.17 mmol) of di-tert-butyl dicarbonate dissolved in 5 mL of dichloromethane are added to a solution of 500 mg (1.97 mmol) of 1-(4-phenylpiperidin-4-yl)propan-1-one hydrochloride and 0.7 mL (4.93 mmol) of triethylamine in 5 mL of dichloromethane. The reaction mixture is stirred for 2 hours at room temperature. The reaction is stopped by adding 10 mL of water. The organic phase is dried over sodium sulfate. The solvents are evaporated off and the residue is then chromatographed on silica gel (eluent: 80/20 heptane/ethyl acetate). 582 mg of tert-butyl 4-phenyl-4-propionylpiperidine-1-carboxylate in the form of a white powder are obtained in a yield of 93%.

17-1-4 tert-Butyl 4-cyclohexyl-4-propionylpiperidine-1-carboxylate

The following are introduced into a Parr bomb: 582 mg (1.83 mmol) of tert-butyl 4-phenyl-4-propionylpiperidine-1-carboxylate, 300 mg of rhodium on alumina and 0.5 mL of acetic acid in 15 mL of dioxane. The reaction mixture is placed under a hydrogen pressure of 6 bar and stirred at 80° C. for 16 hours. The reaction is stopped, filtered through Celite and washed with dichloromethane. The solvents are evaporated off and the residue is then chromatographed on silica gel (eluent: 95/5 heptane/ethyl acetate). 549 mg of tert-butyl 4-cyclohexyl-4-propionylpiperidine-1-carboxylate in the form of a colourless oil are obtained in a yield of 93%.

17-1-5 4-Cyclohexyl-4-propionylpiperidine hydrochloride 549 mg (1.7 mmol) of tert-butyl 4-cyclohexyl-4-propionylpiperidine-1-carboxylate are dissolved in 2 mL (17 mmol) of 4N hydrogen chloride in ethyl acetate. The reaction mixture is stirred for 6 hours at room temperature. The solvents are evaporated off. The residue is taken up in ether and filtered off. 395 mg of 4-cyclohexyl-4-propionylpiperidine hydrochloride in the form of a white powder are obtained in a yield of 90%.

17-2 1-[2-(4-Acetyl-4-cyclohexylpiperidin-1-yl)-1-(4-methoxybenzyl)-2-oxoethyl]-3-(1H-imidazol-4-ylmethyl)urea trifluoroacetate 58 mg (0.42 mmol) of HOBt and 81 mg (0.42 mmol) of EDC and then 0.2 mL (1.15 mmol) of diisopropylethylamine are added to a solution of 128 mg (0.38 mmol) of 2-{3-[2-(1H-imidazol-4-yl)ethyl]ureido}-3-(4-methoxyphenyl)pro-pionic acid (cf. preparation 2-3) and 62.9 mg (0.38 mmol) of 4-cyclohexyl-4-propionylpiperidine hydrochloride in 5 mL of dimethylformamide. The reaction mixture is stirred overnight at room temperature. The reaction is stopped by adding 10 mL of water and is then extracted with ethyl acetate. The organic phases are combined and dried over sodium sulfate. The solvents are evaporated off and the residue is then purified by preparative HPLC (conditions cf. page 38). 98.5 mg of 1-[2-(4-acetyl-4-cyclohexylpiperidin-1-yl)-1-(4-methoxy-benzyl)-2-oxoethyl]-3-(1H-imidazol-4-ylmethyl)-urea trifluoroacetate in the form of a white powder are obtained in a yield of 48%.

HPLC: (method N); retention time: 9.98 min, 97%, M+H: 538.

EXAMPLE 18

1-[2-(4-Cyclohexyl-4-propionylpiperidin-1-yl)-1-(4-methoxy-benzyl)-2-oxoethyl]-3-(1H-imidazol-4-ylmethyl)urea trifluoroacetate (Compound 33)

18-1-1 1-Trityl-1H-imidazole-4-carbaldehyde

To a solution containing 1 g (10.4 mmol) of 1H-imidazole-4-carbaldehyde and 3.18 g (11.4 mmol) of trityl chloride suspended in 28 mL of acetonitrile are added dropwise 2.5 mL (17.7 mmol) of triethylamine. After stirring for 2 hours at room temperature, 30 mL of water are added and the crude reaction product is filtered. 3.2 g in the form of a beige-coloured powder are obtained and used in the following step without further purification.

18-1-2 Piperidin-1-yl-(1-trityl-1H-imidazol-4-ylmethylene)amine

To a solution containing 342 mg (1.01 mmol) of 1-trityl-1H-imidazole-4-carbaldehyde and 100 mg (1.0 mmol) of piperidin-1-ylamine are added 3.5 mL of ethanol and 1.5 mL of dichloromethane. The reaction medium is heated at 80° C. for 1 hour. The solvents are evaporated off and 450 mg of a powder are obtained and used in the following step without further purification.

18-1-3 C-(1H-Imidazol-4-yl)methylamine dihydrochloride

To a solution containing 450 mg of piperidin-1-yl-(1-trityl-1H-imidazol-4-yl-methylene)amine in 3.5 mL of 3N hydrogen chloride in ethyl acetate are added 90 mg of 10% Pd/C, 0.5 mL of THF and 0.9 mL of ethanol. The reaction medium is placed under a hydrogen pressure of 6 bar and heated at 80° C. for 3 hours. After filtering off the catalyst and evaporating off the solvents, the crude product obtained is chromatographed on silica gel (eluent: 6/4 DCM/MeOH). 50 mg of C-(1H-imidazol-4-yl)methylamine dihydrochloride in the form of a white powder are obtained in a yield of 29%.

18-2 Methyl(S)-2-[3-(1H-imidazol-4-yl-methyl)ureido]-3-(4-methoxyphenyl)-propanoate 1.1 g (0.37 mmol) of methyl(S)-3-(4-methoxyphenyl)-2-(4-nitrophenoxycarbonyl-amino)propanoate (cf. preparation 2-2) and 0.7 mL (0.37 mmol) of diisopropyl-ethylamine in 5 mL of dimethylformamide are added at 80° C. to a solution of 500 mg (0.37 mmol) of C-(1H-imidazol-4-yl)methylamine dihydrochloride in 15 mL of dimethylformamide. The reaction mixture is stirred for 2 hours at 80° C. The reaction is stopped by adding 30 mL of water and then extracted with ethyl acetate. The organic phases are combined and dried over sodium sulfate. The solvents are evaporated off and the residue is then chromatographed on silica gel (eluent: 80/20 dichloromethane/methanol). 279 mg of methyl (S)-2-[3-(1H-imidazol-4-yl-methyl)-ureido]-3-(4-methoxyphenyl)propanoate in the form of a yellow oil are obtained in a yield of 63%.

18-3 2-[3-(1H-Imidazol-4-ylmethyl)ureido]-3-(4-methoxyphenyl)propionic acid 351 mg (84 mmol) of lithium hydroxide monohydrate are added to a solution of 278 mg (8.4 mmol) of methyl(S)-2-[3-(1H-imidazol-4-ylmethyl)ureido]-3-(4-methoxy-phenyl)propanoate in 5 mL of tetrahydrofuran and 1 mL of water. The reaction mixture is heated at 100° C. for 10 minutes in a microwave reactor. The reaction is stopped by adding 2 mL of water and 0.5 mL of acetic acid and is then extracted with ethyl acetate. The aqueous phase is concentrated to dryness and the residue is then chromatographed on silica gel (eluent: 7/3 dichloromethane/methanol). 261 mg of 2-[3-(1H-imidazol-4-ylmethyl)ureido]-3-(4-methoxyphenyl)propionic acid in the form of a white foam are obtained in a yield of 98%.

18-4 1-[2-(4-Cyclohexyl-4-propionylpiperidin-1-yl)-1-(4-methoxybenzyl)-2-oxoethyl]-3-(1H-imidazol-4-ylmethyl)urea trifluoroacetate 70 mg (0.52 mmol) of HOBt and 99.4 mg (0.52 mmol) of EDC and then 0.25 mL (1.4 mmol) of diisopropylethylamine are added to a solution of 150 mg (0.47 mmol) of 2-[3-(1H-imidazol-4-ylmethyl)ureido]-3-(4-methoxyphenyl)propionic acid and 123 mg (0.47 mmol) of 1-(4-cyclohexylpiperidin-4-yl)propan-1-one in 5 mL of dimethylformamide. The reaction mixture is stirred for 16 hours at room temperature. The reaction is stopped by adding 10 mL of water and is then extracted with ethyl acetate. The organic phases are combined and dried over sodium sulfate. The solvents are evaporated off and the residue is then purified by preparative HPLC (conditions cf. page 38). 8.5 mg of 1-[2-(4-cyclohexyl-4-propionylpiperidin-1-yl)-1-(4-methoxybenzyl)-2-oxoethyl]-3-(1H-imidazol-4-ylmethyl)urea trifluoroacetate in the form of a colourless oil are obtained in a yield of 4%.

HPLC: (method N); retention time: 9.93 min, 98%, M+H: 524.

EXAMPLE 19

Ethyl 4-cyclohexyl-1-[(R)-2-{3-[2-(1H-imidazol-4-yl)ethyl]-ureido}-3-(4-methoxyphenyl)propionyl]piperidine-4-carboxylate (Compound 34)

19-1 Ethyl 1-[(R)-2-tert-butoxycarbonylamino-3-(4-methoxyphenyl)propionyl]-4-cyclohexylpiperidine-4-carboxylate To 3.22 g (10.9 mmol) of (R)-2-tert-butoxycarbonylamino-3-(4-methoxyphenyl)-propionic acid dissolved in 20 mL of DMF are added 2.29 g (12.0 mmol) of EDC, 1.62 g (12.0 mmol) of HOBt, 2.62 g (10.9 mmol) of ethyl 4-cyclohexylpiperidine-4-carboxylate (cf. preparation 3-1-2) and 4.6 mL (32.7 mmol) of triethylamine. After stirring for 2 hours 30 minutes, the reaction is stopped by adding aqueous 1N sodium hydroxide solution and the organic products are extracted with dichloromethane. The organic phase is dried over MgSO$_4$, filtered and evaporated. The crude product obtained is chromatographed on silica gel (eluent: 7/3 heptane/EtOAc). 3.70 g of ethyl 1-[(R)-2-tert-butoxycarbonylamino-3-(4-methoxyphenyl)propionyl]-4-cyclohexyl-piperidine-4-carboxylate in the form of a white powder are obtained in a yield of 66%.

19-2 Ethyl 1-[(R)-2-amino-3-(4-methoxyphenyl)propionyl]-4-cyclohexylpiperidine-4-carboxylate To 3.7 g (7.16 mmol) of ethyl 1-[(R)-2-tert-butoxycarbonylamino-3-(4-methoxy-phenyl)propionyl]-4-cyclohexylpiperidine-4-carboxylate dissolved in 30 mL of DCM immersed in a bath at 0° C. are added 10 mL of trifluoroacetic acid. After stirring for 1 hour 30 minutes, the solvents are evaporated off. The reaction medium is washed with aqueous 1N sodium hydroxide solution and extracted with DCM. The organic phase is then washed with water and then dried over MgSO$_4$, filtered and concentrated. 2.74 g of ethyl 1-[(R)-2-amino-3-(4-methoxyphenyl)propionyl]-4-cyclohexylpiperidine-4-carboxylate in the form of a white powder are obtained in a yield of 92%.

19-3 Ethyl 4-cyclohexyl-1-[(R)-2-{3-[2-(1H-imidazol-4-yl)ethyl]ureido}-3-(4-methoxy-phenyl)propionyl]piperidine-4-carboxylate To 2.35 g (5.64 mmol) of ethyl 1-[(R)-2-amino-3-(4-methoxyphenyl)propionyl]-4-cyclohexylpiperidine-4-carboxylate dissolved in 25 mL of DCM immersed in a bath of cold water are added 1.25 g (6.21 mmol) of 4-nitrophenyl chloroformate. After warming to room temperature, the reaction medium is stirred for 1 hour. The reaction is stopped by adding aqueous NH$_4$OH solution and the organic compounds are extracted with DCM. The organic phase is then washed with water and then dried over MgSO$_4$, filtered and concentrated. The crude product obtained is dissolved in 25 mL of DMF at 80° C., and 0.70 g (6.3 mmol) of histamine is then added. After 15 minutes, the reaction is stopped by adding aqueous 1N sodium hydroxide solution and the organic compounds are extracted with DCM. The organic phase is dried over MgSO$_4$, filtered and concentrated. The crude product obtained is chromatographed on silica gel (eluent: 86/14 DCM/MeOH). 1.48 g of ethyl 4-cyclohexyl-1-[(R)-2-{3-[2-(1H-imidazol-4-yl)ethyl]ureido}-3-(4-methoxyphenyl)propionyl]piperidine-4-carboxylate in the form of a white powder are obtained in a yield of 47%.

$^1$H NMR/DMSO$_{D6}$ 100° C.: δ=0.87-1.28 (m, 10H); 1.50-1.70 (m, 3H); 1.71-1.74 (m, 2H); 1.80-2.00 (m, 2H); 2.54-2.63 (m, 2H); 2.71-2.83 (m, 2H); 3.24 (bq, J=6.4-6.8 Hz, 1H); 3.74 (s, 3H); 3.75-4.05 (m, 4H); 4.12 (bq, J=6.8-7.2 Hz, 2H); 4.81 (bq, J=6.8-8.0 Hz, 1H); 5.93 (bt, J=4.8-5.6 Hz, 1H); 6.01 (bd, J=8.0 Hz, 1H); 6.73 (s, 1H); 6.82 (bd, J=8.4 Hz, 2H); 7.08 (bd, J=7.6 Hz, 2H); 7.44 (s, 1H); 11.45 (bs, 1H).

EXAMPLE 20

1-[(R)-2-(4-Butyryl-4-cyclohexylpiperidin-1-yl)-1-(4-methoxy-benzyl)-2-oxoethyl]-3-[2-(1H-imidazol-4-yl)ethyl]urea (Compound 40)

20-1 1-(4-Cyclohexylpiperidin-4-yl)butan-1-one 2.5 g (7.4 mmol) of tert-butyl 4-butyryl-4-cyclohexylpiperidine-1-carboxylate (cf. preparation 17-1-4) are diluted in a mixture comprising 40 mL of dichloromethane and 8 mL of trifluoroacetic acid. The mixture is stirred at room temperature for 2 hours and the reaction is then stopped by adding aqueous 1N NaOH solution and the organic compounds are extracted with dichloromethane. The organic phase is dried and then concentrated. 2.1 g of 1-(4-cyclohexylpiperidin-4-yl)butan-1-one in the form of a colourless oil are obtained in a yield of 100%.

20-2 tert-Butyl[(R)-2-(4-butyryl-4-cyclohexylpiperidin-1-yl)-1-(4-methoxybenzyl)-2-oxoethyl]carbamate 2.1 g (8.9 mmol) of 1-(4-cyclohexylpiperidin-4-yl)butan-1-one, 2.6 g (8.9 mmol) of (R)-2-tert-butoxycarbonylamino-3-(4-methoxyphenyl)propionic acid, 1.88 g (9.8 mmol) of EDC and 1.2 g (9.8 mmol) of HOBT are dissolved in 30 mL of DMF. The mixture is stirred at room temperature for 2 hours. The solution is washed with aqueous 2.5% citric acid solution and extracted with ethyl acetate. The organic phase is washed with aqueous 10N NaOH solution and then dried over sodium sulfate, filtered and concentrated. The crude product is chromatographed on silica gel (eluent: 70/30 heptane/ethyl acetate). 1.4 g of tert-butyl[(R)-2-(4-butyryl-4-cyclohexylpiperidin-1-yl)-1-(4-methoxybenzyl)-2-oxoethyl]carbamate in the form of a colourless oil are obtained in a yield of 31%.

20-3 1-{1-[(R)-2-Amino-3-(4-methoxyphenyl)propionyl]-4-cyclohexylpiperidin-4-yl}-butan-1-one 1.4 g (2.7 mmol) of tert-butyl[(R)-2-(4-butyryl-4-cyclohexylpiperidin-1-yl)-1-(4-methoxybenzyl)-2-oxoethyl]carbamate are placed in a mixture composed of 40 mL of DCM and 8 mL of trifluoroacetic acid. The reaction medium is stirred for 2 hours at room temperature and the reaction is then stopped by adding aqueous 1N sodium hydroxide solution. After extracting with dichloromethane, the organic phase is dried over sodium sulfate and then filtered and concentrated. 1.24 g of 1-{1-[(R)-2-amino-3-(4-methoxyphenyl)propionyl]-4-cyclohexylpiperidin-4-yl}butan-1-one in the form of a colourless oil are obtained in a yield of 100%.

20-4 1-[(R)-2-(4-Butyryl-4-cyclohexylpiperidin-1-yl)-1-(4-methoxybenzyl)-2-oxoethyl]-3-[2-(1H-imidazol-4-yl)ethyl]urea 1.24 g (3 mmol) of 1-{1-[(R)-2-amino-3-(4-methoxyphenyl)propionyl]-4-cyclohexyl-piperidin-4-yl}butan-1-one and 660 mg (3.3 mmol) of para-nitrophenyl chloroformate are dissolved in 40 mL of dichloromethane at 0° C. The reaction mixture is stirred for 1 hour at room temperature and the reaction is then stopped by adding 20% aqueous ammonia solution and the organic products are extracted with dichloromethane. The organic phase is washed with water and then dried over sodium sulfate, filtered and concentrated. The white solid obtained is dissolved in 20 mL of DMF, the mixture is heated to 80° C., 0.367 g (3.3 mmol) of histamine is then added and the solution is stirred for 5 minutes at 80° C. and for 10 minutes at room temperature. The reaction is stopped by adding aqueous 1N NaOH solution and the reaction medium is extracted with DCM. The organic phase is washed with water and then dried over sodium sulfate, filtered and concentrated. The crude product obtained is chromatographed on silica gel (eluent: 80/20 DCM/MeOH). 1.1 g of 1-[(R)-2-(4-butyryl-4-cyclo-hexylpiperidin-1-yl)-1-(4-methoxybenzyl)-2-oxoethyl]-3-[2-(1H-imidazol-4-yl)ethyl]urea in the form of a white powder are obtained in a yield of 67%.

$^1$H NMR/DMSO$_{D6}$ 100° C.: δ=0.87-1.22 (m, 10H); 1.38-1.54 (m, 5H); 1.59-1.62 (m, 2H); 1.70-1.73 (m, 2H); 1.85-1.98 (m, 2H); 2.40 (t, J=7.2 Hz, 2H); 2.61 (t, J=7.2 Hz, 2H); 2.70-2.94 (m, 2H); 3.24 (bq, J=6.4-6.8 Hz, 2H); 3.73 (s, 3H); 3.75-4.05 (m, 4H); 4.79 (bq, J=6.8-8.0 Hz, 1H); 5.92 (bt, J=4.8-5.6 Hz, 1H); 5.99 (bd, J=8.0 Hz, 1H); 6.72 (s, 1H); 6.81 (bd, J=8.4 Hz, 2H); 7.07 (bd, J=7.6 Hz, 2H); 7.44 (s, 1H); 11.45 (bs, 1H).

EXAMPLE 21

Ethyl 4-cyclohexyl-1-((R)-3-(3,4-dichlorophenyl)-2-{3-[3-(1H-imidazol-4-yl)propyl]ureido}propionyl)piperidine-4-carboxylate (Compound 45)

21-1 Ethyl 1-[(R)-2-tert-butoxycarbonylamino-3-(3,4-dichlorophenyl)propionyl]-4-cyclohexylpiperidine-4-carboxylate 0.5 g (2.1 mmol) of ethyl piperidine-4-cyclohexyl-4'-carboxylate (cf. preparation 3-1-2), 0.7 g (2.1 mmol) of Boc-3,4-dichloro-D-phenylalanine, 0.31 g (2.3 mmol) of HOBT, 0.44 g (2.3 mmol) of EDC and 0.73 mL (4.2 mmol) of diisopropylethylamine are placed in 5 mL of dimethylformamide. The mixture is stirred for 2 hours at room temperature and then washed with aqueous 5% citric acid solution and extracted with ethyl acetate. The organic phase is washed with aqueous 1N sodium hydroxide solution and then with water and dried over sodium sulfate, filtered and finally concentrated to dryness. The oil obtained is chromatographed (eluent: 5/5 heptane/ethyl acetate). 300 mg of ethyl 1-[(R)-2-tert-butoxycarbonylamino-3-(3,4-dichlorophenyl)propionyl]-4-cyclohexylpiperidine-4-carboxylate are obtained in a yield of 26%.

21-2 Ethyl 1-[(R)-2-amino-3-(3,4-dichlorophenyl) propionyl]-4-cyclohexylpiperidine-4-carboxylate 300 mg (0.54 mmol) of ethyl 1-[(R)-2-tert-butoxycarbonylamino-3-(3,4-dichloro-phenyl)propionyl]-4-cyclohexylpiperidine-4-carboxylate are diluted in 5 mL of a 2/1 dichloromethane/trifluoroacetic acid solution. After 2 hours, the mixture is poured into aqueous 1N sodium hydroxide solution and then extracted with dichloromethane. The organic phase is dried over sodium sulfate and then filtered and concentrated to dryness. 210 mg of ethyl 1-[(R)-2-amino-3-(3,4-dichlorophenyl)propionyl]-4-cyclo-hexylpiperidine-4-carboxylate are obtained in a yield of 86%.

21-3 4-(3-Aminopropyl)-1H-imidazol-1-ium bis(trifluoroacetate)

0.5 g (1.4 mmol) of 3-(1-trityl-1H-imidazol-4-yl)propylamine is dissolved in 8 mL of dichloromethane with 2 mL of trifluoroacetic acid. After 2 hours, the medium is concentrated. The beige-coloured solid obtained is taken up in EtOAc and water, and the aqueous phase is then concentrated to dryness. 0.3 g of 4-(3-aminopropyl)-1H-imidazol-1-ium bis(trifluoroacetate) is obtained in a yield of 61%.

21-4 Ethyl 4-cyclohexyl-1-((R)-3-(3,4-dichlorophenyl)-2-{3-[3-(1H-imidazol-4-yl)-propyl]ureido}propionyl)piperidine-4-carboxylate 0.07 g (0.15 mmol) of ethyl 1-[(R)-2-amino-3-(3,4-dichlorophenyl)propionyl]-4-cyclohexylpiperidine-4-carboxylate and 34 mg (0.17 mmol) of para-nitrophenyl chloroformate are dissolved in 5 mL of dichloromethane. The mixture is stirred for 2 hours at room temperature and the solution is then poured into water and extracted with dichloromethane. The organic phase is dried over sodium sulfate, filtered and concentrated to dryness. The colourless oil obtained is diluted in 5 mL of dimethylformamide, the mixture is heated to 80° C., and 57 mg (0.16 mmol) of 3-(1H-imidazol-4-yl)propylamine bis(trifluoroacetate) are added with 0.05 mL (0.3 mmol) of diisopropylamine. The solution is stirred for 5 minutes at 80° C. and for 16 hours at room temperature. The reaction is stopped by adding aqueous 1N sodium hydroxide solution and then extracted with dichloromethane. The organic phase is washed with water and then dried over sodium sulfate, filtered and evaporated to dryness. The oil obtained is chromatographed (eluent: 90/10 DCM/MeOH). 40 mg of ethyl 4-cyclohexyl-1-((R)-3-(3,4-dichlorophenyl)-2-{3-[3-(1H-imidazol-4-yl)propyl]ureido}-propionyl)piperidine-4-carboxylate in the form of a colourless oil are obtained in a yield of 44%.

$^1$H NMR/DMSO$_{D6}$ 100° C.: δ=0.92-1.20 (m, 6H); 1.22 (t, 3H, 7.2 Hz); 1.27 (m, 2H); 1.61 (m, 2H); 1.72-1.84 (m, 3H); 1.98 (m, 3H); 2.82-3.22 (m, 6H); 3.64 (m, 4H); 3.93 (t, 2H, 6.8 Hz); 4.14 (quart., 2H, 7.2 Hz); 4.87 (quart., 1H, 6.4 Hz); 6.01 (m, 2H); 6.87 (s, 1H); 7.07 (s, 1H); 7.18 (d, 1H, 6.8 Hz); 7.40 (d, 1H, 2.4 Hz); 7.47 (d, 1H, 8.4 Hz); 7.52 (s, 1H)

EXAMPLE 22

Ethyl 4-cyclohexyl-1-[(R)-2-{3-[2-(1H-imidazol-4-yl)ethyl]-thioureido}-3-(4-methoxyphenyl)propionyl]piperidine-4-carboxylate (Compound 47)

22-1 Ethyl 1-[(R)-2-amino-3-(4-methoxyphenyl) propionyl]-4-cyclohexylpiperidine-4-carboxylate trifluoroacetate To 10 g (19.4 mmol) of ethyl 1-[(R)-2-tert-butoxycarbonylamino-3-(4-methoxyphenyl)-propionyl]-4-cyclohexylpiperidine-4-carboxylate (cf. preparation 19-1) in 80 mL of dichloromethane are added, at room temperature, 20 mL of trifluoroacetic acid. The reaction medium is stirred for 2 hours and the solvents are then evaporated off. Diethyl ether and a few drops of dichloromethane are added to the oil obtained, and the white solid obtained is filtered off and then dried. 8 g of ethyl 1-[(R)-2-amino-3-(4-methoxyphenyl)propionyl]-4-cyclohexylpiperidine-4-carboxylate trifluoroacetate are obtained in a yield of 78%.

22-2 Ethyl 4-cyclohexyl-1-[(R)-2-isothiocyanato-3-(4-methoxyphenyl)propionyl]-piperidine-4-carboxylate To 500 mg (0.94 mmol) of ethyl 1-[(R)-2-amino-3-(4-methoxyphenyl)propionyl]-4-cyclohexylpiperidine-4-carboxylate trifluoroacetate dissolved in 5 mL of CH$_2$Cl$_2$ and 0.5 mL (2.8 mmol) of diisopropylethylamine are added 219 mg (0.94 mmol) of thiocarbonic acid O,O-bis(2-pyridyl)ester. After stirring the reaction medium for 2 hours at room temperature, the solvents are evaporated off and the crude product obtained is chromatographed on silica gel (eluent: 6/4 heptane/EtOAc). 421 mg of ethyl 4-cyclohexyl-1-[(R)-2-isothiocyanato-3-(4-methoxyphenyl)propionyl]piperidine-4-carboxylate in the form of a colourless oil are obtained in a yield of 97%.

22-3 Ethyl 4-cyclohexyl-1-[(R)-2-{3-[2-(1H-imidazol-4-yl)ethyl]thioureido}-3-(4-methoxyphenyl)propionyl]piperidine-4-carboxylate To 400 mg (0.87 mmol) of ethyl 4-cyclohexyl-1-[(R)-2-isothiocyanato-3-(4-methoxy-phenyl)propionyl]piperidine-4-carboxylate in 5 mL of DMF are added 97 mg (0.87 mmol) of histamine and then 0.130 mL (0.87 mmol) of 1,8-diazabicyclo[5.4.0]undec-7-ene. The reaction medium is stirred for 2 hours and then hydrolysed by adding aqueous 5% citric acid solution. The organic compounds are extracted with dichloromethane. The organic phase is dried over MgSO$_4$, filtered and concentrated. The crude product obtained is chromatographed on silica gel (eluent: 80/20 CH$_2$Cl$_2$/MeOH). 265 mg of ethyl 4-cyclohexyl-1-[(R)-2-{3-[2-(1H-imidazol-4-yl)ethyl]thioureido}-3-(4-methoxyphenyl)propionyl]piperidine-4-carboxylate in the form of a pale yellow powder are obtained in a yield of 53%.

HPLC: (method U); retention time: 16.05 min, 95%, M+H: 569.

Table I illustrates the examples of compounds according to the invention.

In this table:

- in the "salt" column, TFA represents a compound in trifluoroacetate form
- purity (%) represents the purity of the product obtained from the HPLC spectrum
- mass (M+H) represents the mass+H obtained from the mass spectrum associated with the HPLC peak of the expected product

TABLE I

| No. | Name | Salt | Purity (%) | HPLC retention time (min) | Mass (M + H) | HPLC method used | 1H NMR/DMSOD6 100° C. | Synthetic route used: refer to Example No. |
|---|---|---|---|---|---|---|---|---|
| 1 | 1-[(S)-2-(4-Butyryl-4-phenylpiperidin-1-yl)-1-(4-methoxybenzyl)-2-oxoethyl]-3-[2-(1H-imidazol-4-yl)ethyl]urea | TFA | 98.0 | 15.87 | 545 | A1 | | 1 |
| 2 | 1-[2-(1H-Imidazol-4-yl)ethyl]-3-[1-(4-methoxybenzyl)-2-oxo-2-(4-oxo-1-phenyl-1,3,8-triaza-spiro[4.5]dec-8-yl)ethyl]urea | — | | | | | δ = 1.66 (dl, J = 13.2 Hz, 2H); 2.24-2.32 (m, 1H); 2.61 (t, J = 7.2 Hz, 2H); 2.75 (dd, J = 13.6 Hz, J = 6.8 Hz, 1H); 2.86-2.93 (m, 5H); 3.22-3.28 (m, 2H); 3.42-3.73 (m, 1H); 3.74 (s, 3H); 4.60 (s, 2H); 4.87 (q1, J = 7.2 Hz, 1 H); 5.94 (t, J = 5.6 Hz, 1H); 6.08 (d, J = 8.4 Hz, 1H); 6.72 (s, 1H); 6.77-6.83 (m, 5H); 7.07-7.13 (m, 2H); 7.21 (t, J = 7.6 Hz, 2H); 7.44 (s, 1H); 8.334 (s, 1H). | 2 |
| 3 | 1-[2-(4-Cyano-4-phenylpiperidin-1-yl)-1-(4-methoxybenzyl)-2-oxoethyl]-3-[2-(1H-imidazol-4-yl)ethyl]urea | — | | | | | δ = 1.92-2.13 (m, 2H); 2.62 (t, J = 7.2 Hz, 2H); 2.72-2.99 (m, 8H); 3.26 (q1, J = 5.6-7.2 Hz, 2H); 3.67 (s, 3H); 4.87 (q1, J = 8.4 Hz, 1H) 5.95 (t1, 1H); 6.10 (d, J = 8.4 Hz, 1H); 6.74 (s, 1H); 6.83 (d, J = 8.8 Hz, 2H); 7.11-7.14 (m, 2H); 7.34-7.53 (m, 7H). | 2 |
| 4 | 1-[2-(1H-Imidazol-4-yl))ethyl]-3-[1-(4-methoxybenzyl)-2-oxo-2-(4-phenylpiperidin-1-yl)ethyl]urea | — | | | | | δ = 1.72-1.76 (m, 2H); 2.64 (t, J = 6.8 Hz, 2H); 2.67-2.96 (m, 8H); 3.26 (q1, J = 5.6-7.2 Hz, 2H); 3.73 (s, 3H); 4.89 (q1, J = 8.4 Hz, 1H); 5.96 (t1, J = 5.6 Hz, 1H); 6.04 (d, J = 8.8 Hz, 1H); 6.77 (s, 1H); 6.83-6.86 (m, 2H); 7.11-7.20 (m, 5H); 7.28 (t, J = 7.6 Hz, 2H); 7.53 (s, 1H). | 2 |
| 5 | 1-[2-(1H-Imidazol-4-yl)ethyl]-3-[1-(4-methoxybenzyl)-2-oxo-2-piperidin-1-ylethyl]urea | TFA | 90.0 | 13.16 | 400 | A | | 2 |
| 6 | Ethyl 4-cyclohexyl-1-[2-{3-[2-(1H-imidazol-4-yl)ethyl]ureido}-3-(4-methoxyphenyl)-propionyl]-piperidine-4-carboxylate | — | | | | | δ = 0.87-0.90 (m, 2H); 1.07- 1.37 (m, 13H?); 1.57-1.64 (m, 3H); 1.72-1.75 (m, 2H), 1.92-1.96 (m, 2H); 2.66-2.82 (m, 4H?); 3.29-3.35 (m, 2H); 3.74 (s, 3H); 4.13 (q, J = 6.8-7.2 Hz, 2H); 4.80 (m, 1H); 6.00-6.10 (m, 1H); 6.82 (d, J = 8.4 Hz, 2H); 7.07 (d, J = 8.4 Hz, 2H); 7.30 (s, 1H); 8.80 (s, 1H) | 3 |
| 7 | N-{l-[2-{3-[2-(1H-Imidazol-4-yl)-ethyl]ureido}-3-(4-methoxyphenyl)-propionyl]piperidin-4-yl}-N-phenyl-propionamide | — | | | | | δ = 0.91 (t, J = 7.6 Hz, 3H); 1.01-1.07 (m, 2H); 1.75-1.77 (m, 2H); 1.87 (q, J = 7.2 Hz, 2H); 2.54-2.79 (m, 6H?); 3.20 (q1, J = 6.0-6.8 Hz, 2H); 3.74 (s, 3H); 4.00-4.30 (m, 2H?); 4.53-4.59 (m, 1H); 4.76 (q1, J = 6.8-8.8 Hz, 1H); 5.87-5.94 (m, 2H); 6.74 (d1, J = 8.4 Hz, 3H); 6.99 (d1, J = 8.8 Hz, 2H); 7.12-7.14 (d1, 2H); 7.39-7.46 (m, 4H) | 2 |
| 8 | 1-[2-{3-[2-(1H-Imidazol-4-yl)ethyl]-ureido}-3-(4-methoxyphenyl)-proponyl]-3-phenylazetidin-3-yl butyrate | — | 86.0 | 12.15 | 534 | B | | 4 |
| 9 | Ethyl 1-[2-{3-[2-(1H-imidazol-4-yl)ethyl]ureido}-3-(4-methoxy-phenyl)propionyl]piperidine-4-carboxylate | — | | | | | δ = 1.20 (t, J = 7.2 Hz, 2H); 1.35-1.41 (m, 1H?); 1.72-1.76 (m, 2H); 2.63 (t, J = 6.8 Hz, 2H); 2.70-2.94 (m, 9H?); 3.25 (q1, J = 6-6.4 Hz, 2H); 3.73 (s, 3H); 3.91-3.95 (m, 1H?); 4.09 (q, J = 7.2 Hz, 2H); 4.82 (q1, J = 7.6 Hz, 1H); 5.94 (t1, J = 5.6 Hz, 1H); 6.00 (d, J = 8.8 Hz, 1H); 6.79-6.83 (m, 3H); 7.08 (d, J = 8.8 Hz, 2H); 7.60 (s1, 1H). | 2 |
| 10 | 1-[2-(1H-Imidazol-4-yl)ethyl]-3-{1-(4-methoxybenzyl)-2-[4-(2-methoxyphenyl)piperidin-1-yl]-2-oxoethyl}urea | — | | | | | δ = 1.61-1.70 (m, 2H); 2.64 (t, J = 6.8 Hz, 2H); 2.72-3.10 (m, 8H); 3.26 (q1, J = 6-6.8 Hz, 2H); 3.73 (s, 3H); 3.80 (s, 3H); 4.88 (q1, J = 7.6 Hz, 1H); 5.97 (t1, J = 5.2 Hz, 1H); 6.06 (d, J = 8.8 Hz, 1H); 6.78 (s, 1H); 6.82-6.99 (m, 5H); 7.11-7.19 (m, 3H); 7.55 (s, 1H). | 2 |
| 11 | 1-[2-(3-Butoxy-3-phenylazetidin-1-yl)-1-(4-methoxybenzyl)-2-oxoethyl]-3-[2-(1H-imidazol-4-yl)ethyl]urea | — | 93.0 | 11.6 | 520 | C | | 5 |

TABLE I-continued

| No. | Name | Salt | Purity (%) | HPLC retention time (min) | Mass (M + H) | HPLC method used | 1H NMR/DMSOD6 100° C. | Synthetic route used: refer to Example No. |
|---|---|---|---|---|---|---|---|---|
| 12 | Methyl 4-cyclohexyl-1-[2-{3-[2-(1H-imidazol-4-yl)ethyl]-ureido}-3-(4-methoxyphenyl)-propionyl]piperidine-4-carboxylamide | — | 97.0 | 11.82 | 539 | D | | 6 |
| 13 | 1-[2-(3-Cyclohexanecarbonyl-azetidin-1-yl)-1-(4-methoxy-benzyl)-2-oxoethyl]-3-[2-(1H-imidazol-4-yl)ethyl]urea | — | 86.0 | 12.36 | 482 | E | | 7 |
| 14 | Ethyl 4-cyclohexyl-1-[2-{3-ethyl-3-[2-(1H-imidazol-4-yl)ethyl]ureido}-3-(4-methoxyphenyl)propionyl]-piperidine-4-carboxylate | — | 91.0 | 20.72 | 582 | F | | 8 |
| 15 | N-Cyclopropyl-N-{1-[2-{3-[2-(1H-imidazol-4-yl)ethyl]ureido}-3-(4-methoxyphenyl)propionyl]-piperidin-4-yl}propionamide | — | 92.2 | 12.46 | 511 | G | | 9 |
| 16 | Ethyl 4-cyclohexyl-1-(2-{3-[2-(1H-imidazol-4-yl)ethyl]ureido}-3-phenyl-propionyl)piperidine-4-carboxylate | TFA | 99.0 | 10.14 | 524 | I | | 3 |
| 17 | 1-[2-(4-Butyryl-4-cyclohexyl-piperidin-1-yl)-1-(4-methoxybenzyl)-2-oxoethyl]-3-[2-(3H-imidazol-4-yl)-ethyl]urea | TFA | 97.0 | 21.49 | 552 | J | | 10 |
| 18 | 1-[2-(4-Butoxy-4-cyclohexyl-piperidin-1-yl)-1-(4-methoxybenzyl)-2-oxoethyl]-3-[2-(1H-imidazol-4-yl)-ethyl]urea | — | | | | | δ = 0.87-0.94 (m, 4H); 1.06-1.23 (m, 5H); 1.33-1.68 (m, 12H); 1.72-1.80 (m, 3H); 2.63 (t, J = 7.6 Hz, 2H); 2.71-2.83 (m, 4H); 2.91-3.09 (m, 2H); 3.19-3.28 (m, 4H); 3.73 (s, 3H); 4.84 (ql, J = 6.4-8.4 Hz, 1H); 5.96-6.02 (m, 2H); 6.79 (d, J = 5.6 Hz, 2H); 6.82 (s, 1H); 7.08 (d, J = 8.0 Hz, 2H); 7.58 (s, 1H). | 11 |
| 19 | Ethyl 4-cyclohexyl-1-(2-{3-[2-(1H-imidazol-4-yl)ethyl]ureido}-2-phenyl-acetyl)piperidine-4-carboxylate | — | 99.0 | 19.9 | 510 | K | | 3 |
| 20 | Methyl 4-cyclohexyl-1-[2-{3-[2-(1H-imidazol-4-yl)ethyl]ureido}-3-(4-methoxyphenyl)propionyl]piperidine-4-carboxylate | — | | | | | δ = 0.84-0.88 (m, 2H); 1.03-1.28 (m, 5H); 1.56-1.63 (m, 3H); 1.71-1.74 (m, 2H); 1.86-1.94 (m, 2H); 2.62 (t, J = 7.2 Hz, 2H); 2.71-2.83 (m, 6H); 3.24 (ql, J = 6.0-6.8 Hz, 2H); 3.64 (s, 3H); 3.74 (s, 3H); 3.90-4.10 (m, 1H); 4.81 (ql, J = 6.0-8.4 Hz, 1H); 5.93 (tl, J = 5.2-5.6 Hz); 6.01 (d1, J = 8.8 Hz, 1H); 6.73 (s, 1H); 6.82 (d, J = 8.0 Hz, 2H); 7.08 (d, J = 8.4 Hz, 2H); 7.45 (s, 1H); 7.97 (s, 1H). | 3 |
| 21 | 1-[2-(4-Cyclohexyl-4-ethoxy-piperidin-1-yl)-1-(4-methoxybenzyl)-2-oxoethyl]-3-[2-(1H-imidazol-4-yl)ethyl]urea- | — | | | | | δ = 0.88-0.93 (m, 2H); 1.06-1.29 (m, 8H); 1.36-1.68 (m, 7H); 1.72-1.76 (m, 2H); 2.62 (tl, J = 6.8-7.2 Hz, 2H); 2.71-2.84 (m, 3H); 3.22-3.29 (m, 4H); 3.73 (s, 3H); 3.90-4.10 (m, 2H); 4.85 (ql, J = 6.4-8.0 Hz, 1H); 5.96 (tl, J = 5.2-6.0 Hz, 1H); 6.01 (d1, J = 8.4 Hz, 1H); 6.74 (s, 1H); 6.81 (d, J = 8.4 Hz, 2H); 7.08 (d, J = 8.8 Hz; 1H); 7.47 (s, 1H). | 11 |
| 22 | 1-[2-(4-Acetyl-4-cyclohexylpiperidin-1-yl)-1-(4-methoxybenzyl)-2-oxoethyl]-3-[2-(1H-imidazol-4-yl)ethyl]urea | TFA | 96.0 | 15.61 | 524 | L | | 10 |
| 23 | Methyl 4-cyclohexyl-1-(2-{3-[2-(1H-imidazol-4-yl)ethyl]ureido}-2-phenyl-acetyl)piperidine-4-carboxylate | — | 99.0 | 10.34 | 496 | M | | 3 |
| 24 | Ethyl 4-ethyl-1-[2-{3-[2-(1H-imidazol-4-yl)ethyl]ureido}-3-(4-methoxyphenyl)propionyl]-piperidine-4-carboxylate | — | 93.0 | 9.32 | 500 | M | | 12 |
| 25 | 1-[2-(4-Cyclohexyl-4-propoxy-piperidin-1-yl)-1-(4-methoxybenzyl)-2-oxoethyl]-3-[2-(1H-imidazol-4-yl)ethyl]urea | TFA | | | | | δ = 0.90 (tl, J= 7.2-7.6 Hz, 4H); 1.17-1.21 (m, 3H); 1.45-1.63 (m, 8H); 1.73-1.76 (m, 2H); 2.71-2.83 (m, 6H); 3.00-3.40 (m, 9H); 3.73 (s, 3H); 4.00-1.10 (m, 1H); 4.83 (tl, 1H); 5.90-6.10 (m, 2H); 6.82 (d, J = 8.4 Hz, 2H); 7.07 (d, J = 8.0 Hz, 2H); 7.32 (s, 1H); 8.82 (s, 1H). | 11 |

TABLE I-continued

| No. | Name | Salt | Purity (%) | HPLC retention time (min) | Mass (M + H) | HPLC method used | 1H NMR/DMSOD6 100° C. | Synthetic route used: refer to Example No. |
|---|---|---|---|---|---|---|---|---|
| 26 | Cyclohexyl-1-[2-[3-[2-(1H-imidazol-4-yl)ethyl]ureido}-3-(4-methoxyphenyl)propionyl]-piperidine-4-carboxylic acid | TFA | 96.0 | 14.75 | 526 | L | | 13 |
| 27 | 1-[2-(1H-Imidazol-4-yl)ethyl]-3-{1-(4-methoxybenzyl)-2-[3-(2-methyl-cyclohexyl)-3-propoxyazetidin-1-yl]-2-oxoethyl}urea | TFA | | | | | δ = 0.79-0.86 (m, 3H); 0.88-0.95 (m, 3H); 1.10-1.30 (m, 2H); 1.40-1.50 (m, 8H); 1.63-1.73 (m, 2H); 1.98-2.05 (m, 1H); 2.78 (q1, J = 6.8-8.8 Hz, 5H); 3.22-3.38 (m, 2H); 3.56-3.70 (m, 3H); 3.75 (s, 3H); 3.80-4.20 (m, 1H); 4.34 (t1, J = 7.2 Hz, 1H); 5.90-6.20 (m, 2H); 6.85 (d1, 2H); 7.10 (d, J = 8.0 Hz, 2H); 7.31 (s, 1H); 8.82 (s, 1H). | 14 |
| 28 | Propyl 4-cyclohexyl-1-[2-{3-[2-(1H-imidazol-4-yl)ethyl]ureido}-3-(4-methoxyphenyl)propionyl]piperidine-4-carboxylate | TFA | | | | | δ = 0.85-0.92 (m, 5H); 1.02-1.24 (m, 5H); 1.59-1.65 (m, 5H); 1.69-1.73 (m, 2H); 1.85-1.94 (m, 2H); 2.48-2.54 (m, 1H); 2.69-2.81 (m, 5H); 3.29-3.31 (m, 2H); 3.72 (s, 4H); 3.90-4.06 (m, 4H); 4.78 (m, 1H); 5.95-6.20 (m, 2H); 6.81 (d1, J = 7.2 Hz, 2H); 7.06 (d1, J = 7.6 Hz, 2H); 7.30 (s, 1H); 8.79 (s, 1H). | 3 |
| 29 | 1-[2-(1H-Imidazol-4-yl)ethyl]-3-[1-(4-methoxybenzyl)-2-oxo-2-(3-pentyl-3-phenylazetidin-1-yl)ethyl]urea | — | 97.0 | 10.55 | 518 | N | | 15 |
| 30 | Ethyl 1-((R)-3-(4-chlorophenyl)-2-{3-[2-(1H-imidazol-4-yl)ethyl]ureido}-propionyl)-4-cyclohexylpiperidine-4-carboxylate | — | 96.0 | 11.01 | 558 | N | | 16 |
| 31 | Ethyl 1-((S)-3-(4-chlorophenyl)-2-{3-[2-(1H-imidazol-4-yl)ethyl]ureido}-propionyl)-4-cyclohexylpiperidine-4-carboxylate | — | 98.0 | 11 | 558 | N | | 16 |
| 32 | 1-[2-(4-Cyclohexyl-4-propionylpiperidin-1-yl)-1-(4-methoxybenzyl)-2-oxoethyl]-3-[2-(1H-imidazol-4-yl)ethyl]urea | TFA | 97.0 | 9.98 | 538 | N | | 17 |
| 33 | 1-[2-(4-Cyclohexyl-4-propionylpiperidin-1-yl)-1-(4-methoxybenzyl)-2-oxoethyl]-3-(1H-imidazol-4-ylmethyl)urea | TFA | 98.0 | 9.93 | 524 | N | | 18 |
| 34 | Ethyl 4-cyclohexyl-1-[(R)-2-{3-[2-(1H-imidazol-4-yl)ethyl]ureido}-3-(4-methoxyphenyl)propionyl]piperidine-4-carboxylate | — | | | | | | 19 |
| 35 | Ethyl 4-cyclopropylmethyl-1-[2-{3-[2-(1H-imidazol-4-yl)ethyl]ureido}-3-(4-methoxyphenyl)propionyl]piperidine-4-carboxylate | TFA | 2 pics: 69% + 30% | 2 pics: 18.53 + 18.73 | 526 | O | | 12 |
| 36 | Propyl 4-cyclohexyl-1-(2-{3-[2-(1H-imidazol-4-yl)ethyl]ureido}-3-phenyl-propionyl)piperidine-4-carboxylate | TFA | 98.0 | 10.91 | 538 | N | | 3 |
| 37 | Ethyl 4-cyclopentyl-1-[2-{3-[2-(1H-imidazol-4-yl)ethyl]ureido}-3-(4-methoxy-phenyl)propionyl]piperidine-4-carboxylate | TFA | 93.0 | 16.99 | 510 | P | | 12 |
| 38 | Ethyl 4-cyclohexyl-1-[(S)-2-{3-[2-(1H-imidazol-4-yl)ethyl]ureido}-3-(4-methoxy-phenyl)propionyl]piperidine-4-carboxylate | TFA | 98.0 | 9.92 | 540 | Q | | 12 |
| 39 | Ethyl 4-cyclohexyl-1-[(S)-2-{3-[2-(1H-imidazol-4-yl)ethyl]ureido}-3-(4-methoxyphenyl)propionyl]piperidine-4-carboxylate | — | 100.0 | 10.33 | 554 | N | | 19 |
| 40 | 1-[(R)-2-(4-Butyryl-4-cyclohexyl-piperidin-1-yl)-1-(4-methoxybenzyl)-2-oxoethyl]-3-[2-(1H-imidazol-4-yl)-ethyl]urea | — | | | | | δ = 0.87-1.22 (m, 10H); 1.38-1.54 (m, 5H); 1.59-1.62 (m, 2H); 1.70-1.73 (m, 2H); 1.85-1.98 (m, 2H); 2.40 (t, J = 7.2 Hz, 2H); 2.61 (t, J = 7.2 Hz, 2H); 2.70-2.94 (m, 2H); 3.24 (q1, J = 6.4-6.8 Hz, 2H); 3.73 (s, 3H); 3.75-4.05 (m, 4H); 4.79 (q1, J = 6.8-8.0 Hz, 1H); 5.92 (t1, J = 4.8-5.6 Hz, 1H); 5.99 (d1, J = | 20 |

TABLE I-continued

| No. | Name | Salt | Purity (%) | HPLC retention time (min) | Mass (M + H) | HPLC method used | 1H NMR/DMSOD6 100° C. | Synthetic route used: refer to Example No. |
|---|---|---|---|---|---|---|---|---|
| 41 | 1-[(R)-2-(4-Butyryl-4-cyclohexyl-piperidin-1-yl)-1-(4-fluorobenzyl)-2-oxoethyl]-3-[2-(1H-imidazol-4-yl)-ethyl]urea | — | 99.0 | 18.04 | 540 | R | 8.0 Hz, 1H); 6.72 (s, 1H); 6.81 d1, J = 8.4 (Hz, 2H); 7.07 (d1, J = 7.6 Hz, 2H); 7.44 (s, 1H); 11.45 (s1, 1H). | 20 |
| 42 | 1-[(R)-1-Benzyl-2-(4-butyryl-4-cyclohexylpiperidin-1-yl)-2-oxoethyl]-3-[2-(1H-imidazol-4-yl)ethyl]urea | — | 99.0 | 17.95 | 522 | R | | 20 |
| 43 | 1-[(R)-2-(4-Butyryl-4-cyclohexyl-piperidin-1-yl)-1-(4-methoxybenzyl)-2-oxoethyl]-3-[2-(3-methyl-3H-imidazol-4-yl)ethyl]urea | — | 98.0 | 15.69 | 566 | S | | 20 |
| 44 | 1-[(R)-2-(4-Butyryl-4-cyclohexyl-piperidin-1-yl)-1-(4-chlorobenzyl)-2-oxoethyl]-3-[2-(1H-imidazol-4-yl)-ethyl]urea | — | 92.0 | 16.54 | 556 | S | | 20 |
| 45 | Ethyl 4-cyclohexyl-1-((R)-3-(3,4-dichlorophenyl)-2-{3-[3-(1H-imidazol-4-yl)propyl]ureido}propionyl)piperidine-4-carboxylate | — | | | 606 | | δ = 0.92-1.20(m, 6H); 1.22(t, 3H, 7.2 Hz); 1.27(m, 2H); 1.61(m, 2H); 1.72-1.84(m, 3H); 1.98(m, 3H); 2.82-3.22(m, 6H); 3.64(m, 4H); 3.93(t, 2H, 6.8 Hz); 4.14(qua, 2H, 7.2 Hz); 4.87(qua, 1H, 6.4 Hz); 6.01 (m, 2H); 6.87(s, 1H); 7.07(s, 1H); 7.18(d, 1H, 6.8 Hz); 7.40 (d, 1H, 2.4 Hz); 7.47 (d, 1H, 8.4 Hz); 7.52(s, 1H) | 21 |
| 46 | Ethyl 4-cyclohexyl-1-((R)-3-(4-methoxyphenyl)-2-{3-[2-(3-methyl-3H-imidazol-4-yl)etnyl]ureido}propionyl)-piperidine-4-carboxylate | — | | | 567 | | δ: 0.89(m, 2H); 1.06-1.19(m, 4H); 1.21(m, 3H); 1.28(m, 2H); 1.60(m 3H); 1.72(m, 2H); 1.93(m, 2H); 2.63(t, 2H, 6.8 Hz); 2.76(m, 6H); 3.21(qua, 2H, 6.8 Hz); 3.52(s, 3H); 3.73(s, 3H); 4.13(qua, 2H, 7.2 Hz); 4.82(qua, 1H, 7.6 Hz); 6.02(m, 2H); 6.65(s, 1H); 6.82 (d, 2H, 8 Hz); 7.08(d, 2H, 8 Hz); 7.40 (s, 1H); 7.96(s, 1H) | 19 |
| 47 | Ethyl 4-cyclohexyl-1-[(R)-2-{3-[2-(1H-imidazol-4-yl)ethyl]thioureido}-3-(4-methoxyphenyl)propionyl]piperidine-4-carboxylate | — | 95.0 | 16.05 | 569 | U | | 22 |

EXAMPLE 23

Transactivation Test

Cells:
The lines HEK293 are transfected with vectors pCRE-Luc and hMC1R. The cells are cultured at 37° C. and 5% $CO_2$, in DMEM medium supplemented with 10% foetal calf serum.

Test Principle:
In the presence of an activator (agonist), the melanocortin receptor will activate the cAMP pathway, which, via the vector CRE-Luc, will lead to the synthesis of luciferase. After addition of a lysis buffer containing a luminescent luciferase substrate, the luminescence proportional to the degree of activation or inhibition of receptor may be measured.

Testing the Products:
The products are dissolved at 10 mM in DMSO. They are tested as a response dose at 0.1% of DMSO final. The range comprising 10 points and a zero starts at 10 μM with four-fold dilutions. To test agonists, the products are tested alone. To determine the antagonist behaviour, the products of interest are tested in the presence of 1 nM NDP-MSH (reference agonist). The cells are inoculated at a rate of 5000 cells per well (384-well plate) in serum-free DMEM medium and incubated overnight at 37° C. and 5% $CO_2$.

The products and the reference ligand (NDP-MSH) are added the following day and the plates are reincubated for 6 hours at 37° C. and 5% $CO_2$. After adding the lysis buffer containing luciferin, the plates are read in a Top-Count machine. The results are normalized as percentage of activity using the 100% (cells+NDP-MSH at 10 nM) and 0% (cells alone) controls. An EC50 is calculated for each product using the XLFit software. The results are given in nM.

| Compound No. | EC50 hMC1-R (nM) |
|---|---|
| 34 | 60 |
| 40 | 120 |

EXAMPLE 24

Test of Metabolic Stability in the Presence of Liver Microsomes

Liver Microsomes:
The microsomes are cellular endoplasmic reticulum vesicles obtained after purification, from liver tissue. They contain membrane enzymes (Cytochromes P450) involved in oxidative metabolism (phase I).

Test Principle:

In a buffered reaction medium at 37° C., the test product is incubated in the presence of microsomes from different species. Samples of the incubate are taken at different times (kinetics). Quantification by LC/MS/MS analysis makes it possible to measure the disappearance of parent product associated with the phase I liver metabolism.

Testing the Products:

The products are dissolved at 10 mM in DMSO. They are incubated at 10 µM in the presence of microsomes (0.5 mg/ml). The reaction medium is formed from 100 mM phosphate buffer at pH 7.4, G6PDH (0.4 U/ml), 0.01% Pluronic acid and cofactors $MgCl_2$ 5 mM, NADP and G6P (1.3 mM and 3.3 mM, respectively). Samples of the reaction medium are taken at 0, 5, 10, 15, 30 and 60 minutes. At each time, the enzymatic reaction is stopped by adding methanol. After centrifugation (3000 rpm, 30 minutes), the samples are analysed by LC/MS/MS. The concentration of parent product remaining is quantified over time and allows a half-life to be calculated for each product.

| Compound No. | t½ (min) |
|---|---|
| 34 | 3-4 min |
| 40 | 3-4 min |

EXAMPLE 25

Lod P and Loci D by HPLC-MS

Definition:

Log P, also known as Log Kow, (octanol/water partition coefficient) enables characterization of the lipophilic nature of a molecule.

$$\text{Log P} = \text{Log}(C_{oct}/C_{water})$$

In contrast with Log P, Log D is a determination of a given pH.

Preparation of the Samples

The molecule at $10^{-2}$M in DMSO is placed in an octanol-water mixture (50/50 volume/volume).

After stirring for ten hours, the sample is centrifuged and the two phases are separated in order to be analysed. The octanol phase is diluted in methanol before assay.

The concentrations of test molecule present in each phase are determined by an LC/MS/MS analysis.

$$\text{Log P} = \text{Log}(\text{area}_{oct} * \text{Dilution factor}/\text{area}_{aq})$$

| Compound No. | logD (pH 6.5) |
|---|---|
| 34 | 4 |
| 40 | 4.8 |

EXAMPLE 26

Figure 2:
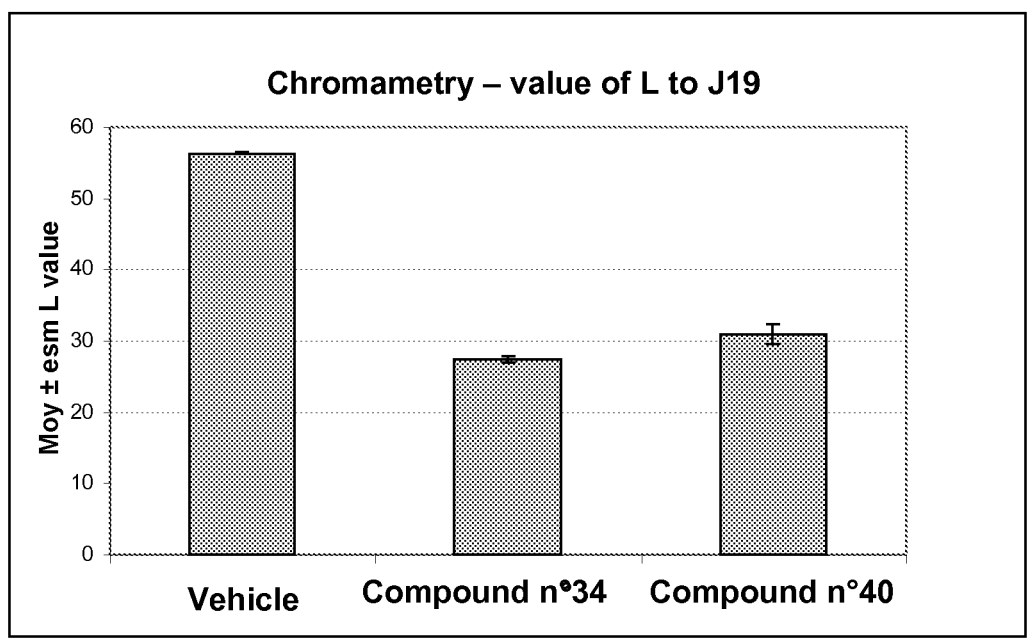
FIG. 2 is a bar graph showing the modulation of the pigmentation of hair during regrowth after depilation in mice, where the L value measures color on a scale where the smaller the value of L, the darker the hair, for two compounds of the invention diluted in ethanol and applied topically each day for 11 days after depilation.

Modulation of the Pigmentation of Hair During Regrowth After Depilation in Mice: (Results in Table of FIG. 2)

Female 8-week-old B6.Cg-Ay mice are shaved and then subjected to depilation with cold wax under gaseous anaesthesia to synchronize all the hair follicles at the start of the anagenic phase.

After depilation, the MC1R agonists diluted to 5% in ethanol are applied topically every day to the depilated area for 11 days. Nineteen days after depilation, the pigmentation of the hairs is measured by chromametry on the area of regrowth: the L value measures the colour on a scale ranging from black to white (the smaller the value of L, the darker the hair).

| | Value of L at D19 | |
|---|---|---|
| | Mean | SEM |
| Vehicle | 56.33 | 0.10 |
| Compound 34 | 27.42 | 0.48 |
| Compound 40 | 31.00 | 1.45 |

The invention claimed is:
1. A compound of formula (I):

in which:

R1 represents a hydrogen atom; an aryl which is an unsubstituted phenyl or naphthyl; a substituted aryl which is a phenyl or naphthyl substituted with one or more groups of atoms selected from the group consisting of a lower alkyl having up to 4 carbon atoms, a lower alkoxy having up to 4 carbon atoms, a halogen, a hydroxyl, a cyano, a trifluoromethyl and a nitro; a lower alkyl having up to 4 carbon atoms; a cycloalkyl having 3 to 7 carbon ring atoms; or a cycloalkyl(lower alkyl) wherein the cycloalkyl portion has 3 to 7 carbon ring atoms and the lower alkyl portion has up to 4 carbon atoms;

R2 represents a hydrogen atom; a lower alkyl which is a linear or branched, saturated or unsaturated hydrocarbon-based chain having up to 4 carbon atoms; a substituted lower alkyl which is a linear or branched, saturated or unsaturated hydrocarbon-based chain having up to 4 carbon atoms and substituted with one or more halogen atoms or with a hydroxyl; a higher alkyl which is a linear or branched, saturated or unsaturated hydrocarbon-based chain having from 5 to 10 carbon atoms; a substituted higher alkyl which is a linear or branched, saturated or unsaturated hydrocarbon-based chain having from 5 to 10 carbon atoms and substituted with one or more halogen atoms or with a hydroxyl; a lower alkoxy which is an oxygen atom substituted with a linear or branched, saturated or unsaturated hydrocarbon-based chain having up to 4 carbon atoms; a substituted lower alkoxy which is an oxygen atom substituted with a linear or branched, saturated or unsaturated hydrocarbon-based chain having up to 4 carbon atoms and substituted with one or more halogen atoms or with a hydroxyl; an acyloxy which is an oxygen substituted with a carbonyl substituted with a lower alkyl having up to 4 carbon atoms; an acyl which is a carbonyl substituted with a lower alkyl having up to 4 carbon atoms; a (lower alkoxy)carbonyl which is a carbonyl substituted with a lower alkoxy having up to 4 carbon atoms; a carboxamide which is a carbonyl substituted with a mono(lower alkyl)amino having up to 4 carbon atoms or with a di(lower alkyl)amino wherein each lower alkyl has up to 4 carbon atoms; a carboxylic acid; a cyano; or an amino disubstituted with an acyl, which is a carbonyl substituted with a lower alkyl having up to 4 carbon atoms, and with a lower alkyl having up to 4 carbon atoms or aryl which is an unsubstituted phenyl or naphthyl;

R3 represents an aralkyl which is a lower alkyl having up to 4 carbon atoms substituted with an unsubstituted phenyl or naphthyl; or a substituted aralkyl which is a lower alkyl having up to 4 carbon atoms substituted with a phenyl or naphthyl substituted with one or more groups of atoms selected from the group consisting of a lower alkyl having up to 4 carbon atoms, a lower alkoxy having up to 4 carbon atoms, a halogen, a hydroxyl, a cyano, a trifluoromethyl and a nitro;

R4 represents an imidazolyl(lower alkyl) which is a lower alkyl having up to 4 carbon atoms substituted with an imidazole or a substituted imidazolyl(lower alkyl) which is a lower alkyl having up to 4 carbon atoms substituted with an imidazole substituted with one or more lower alkyl groups each having up to 4 carbon atoms;

R5 represents a hydrogen atom or a lower alkyl having up to 4 carbon atoms;

X represents an oxygen atom or a sulfur atom; and
each of n and m is equal to 1 or 2;
or a corresponding salt or enantiomer.

2. The compound according to claim 1, in which:
R1 represents a hydrogen atom, an aryl, a substituted aryl, a lower alkyl, a cycloalkyl or a cycloalkyl(lower alkyl),
R2 represents a hydrogen atom, a lower alkyl, a substituted lower alkyl, a higher alkyl, a substituted higher alkyl, a lower alkoxy, a substituted lower alkoxy, an acyloxy, an acyl, a (lower alkoxy)carbonyl, a carboxamide or a cyano, and
R5 represents a hydrogen atom,
or a corresponding salt or enantiomer.

3. The compound according to claim 2, in which:
R1 represents a cycloalkyl or a cycloalkyl(lower alkyl),
R2 represents a lower alkoxy, an acyl, a (lower alkoxy)carbonyl or a cyano, and
each of n and m is equal to 2;
or a corresponding salt or enantiomer.

4. The compound according to claim 3, in which:
R1 represents a cycloalkyl,
R2 represents a lower alkoxy, an acyl or an alkoxycarbonyl, and
R4 represents an imidazolyl(lower alkyl),
or a corresponding salt or enantiomer.

5. The compound according to claim 4, in which:
R2 represents an acyl or a (lower alkoxy)carbonyl,
or a corresponding salt or enantiomer.

6. The compound which is selected from the group consisting of:
1-[(S)-2-(4-Butyryl-4-phenylpiperidin-1-yl)-1-(4-methoxybenzyl)-2-oxoethyl]-3-[2-(1H-imidazol-4-yl)ethyl]urea;
1-[2-(4-Cyano-4-phenylpiperidin-1-yl)-1-(4-methoxybenzyl)-2-oxoethyl]-3-[2-(1H-imidazol-4-yl)ethyl]urea;
1-[2-(1H-Imidazol-4-yl)ethyl]-3-[1-(4-methoxybenzyl)-2-oxo-2-(4-phenylpiperidin-1-yl)ethyl]urea;
1-[2-(1H-Imidazol-4-yl)ethyl]-3-[1-(4-methoxybenzyl)-2-oxo-2-piperidin-1-yl-ethyl]urea;
Ethyl 4-cyclohexyl-1-[2-{3-[2-(1H-imidazol-4-yl)ethyl]ureido}-3-(4-methoxyphenyl)-propionyl]piperidine-4-carboxylate;
N-{1-[2-{3-[2-(1H-Imidazol-4-yl)ethyl]ureido}-3-(4-methoxyphenyl)propionyl]piperidin-4-yl}-N-phenyl-propionamide;
1-[2-{3-[2-(1H-Imidazol-4-yl)ethyl]ureido}-3-(4-methoxyphenyl)propionyl]-3-phenylazetidin-3-yl butyrate;
Ethyl 1-[2-{3-[2-(1H-imidazol-4-yl)ethyl]ureido}-3-(4-methoxyphenyl)propionyl]piperidine-4-carboxylate;
1-[2-(1H-Imidazol-4-yl)ethyl]-3-{1-(4-methoxybenzyl)-2-[4-(2-methoxyphenyl)piperidin-1-yl]-2-oxoethyl}urea;
1-[2-(3-Butoxy-3-phenylazetidin-1-yl)-1-(4-methoxybenzyl)-2-oxoethyl]-3-[2-(1H-imidazol-4-yl)ethyl]urea;
Methyl 4-cyclohexyl-1-[2-{3-[2-(1H-imidazol-4-yl)ethyl]ureido}-3-(4-methoxyphenyl)-propionyl]piperidine-4-carboxylamide;
1-[2-(3-Cyclohexanecarbonylazetidin-1-yl)-1-(4-methoxybenzyl)-2-oxoethyl]-3-[2-(1H-imidazol-4-yl)ethyl]urea;
Ethyl 4-cyclohexyl-1-[2-{3-ethyl-3-[2-(1H-imidazol-4-yl)ethyl]ureido}-3-(4-methoxyphenyl)propionyl]piperidine-4-carboxylate;
N-Cyclopropyl-N-{1-[2-{3-[2-(1H-imidazol-4-yl)ethyl]ureido}-3-(4-methoxyphenyl)propionyl]piperidin-4-yl}propionamide;
Ethyl 4-cyclohexyl-1-(2-{3-[2-(1H-imidazol-4-yl)ethyl]ureido}-3-phenylpropionyl)piperidine-4-carboxylate;
1-[2-(4-Butyryl-4-cyclohexylpiperidin-1-yl)-1-(4-methoxybenzyl)-2-oxoethyl]-3-[2-(3H-imidazol-4-yl)ethyl]urea;
1-[2-(4-Butoxy-4-cyclohexylpiperidin-1-yl)-1-(4-methoxybenzyl)-2-oxoethyl]-3-[2-(1H-imidazol-4-yl)ethyl]urea;
Ethyl 4-cyclohexyl-1-(2-{3-[2-(1H-imidazol-4-yl)ethyl]ureido}-2-phenylacetyl)piperidine-4-carboxylate;
Methyl 4-cyclohexyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-ethoxypiperidin-1-yl)-1-(4-methoxybenzyl)-2-oxoethyl]-3-[2-(1H-imidazol-4-yl)ethyl]urea;
1-[2-(4-Acetyl-4-cyclohexylpiperidin-1-yl)-1-(4-methoxybenzyl)-2-oxoethyl]-3-[2-(1H-imidazol-4-yl)ethyl]urea;
Methyl 4-cyclohexyl-1-(2-{3-[2-(1H-imidazol-4-yl)ethyl]ureido}-2-phenylacetyl)piperidine-4-carboxylate;
Ethyl 4-ethyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-propoxypiperidin-1-yl)-1-(4-methoxybenzyl)-2-oxoethyl]-3-[2-(1H-imidazol-4-yl)ethyl]urea;
4-Cyclohexyl-1-[2-{3-[2-(1H-imidazol-4-yl)ethyl]ureido}-3-(4-methoxyphenyl)propionyl]piperidine-4-carboxylic acid;

1-[2-(1H-Imidazol-4-yl)ethyl]-3-{1-(4-methoxybenzyl)-2-[3-(2-methylcyclohexyl)-3-propoxyazetidin-1-yl]-2-oxoethyl}urea;
Propyl 4-cyclohexyl-1-[2-{3-[2-(1H-imidazol-4-yl)ethyl]ureido}-3-(4-methoxyphenyl)propionyl]piperidine-4-carboxylate;
1-[2-(1H-Imidazol-4-yl)ethyl]-3-[1-(4-methoxybenzyl)-2-oxo-2-(3-pentyl-3-phenylazetidin-1-yl)ethyl]urea;
Ethyl 1-((R)-3-(4-chlorophenyl)-2-{3-[2-(1H-imidazol-4-yl)ethyl]ureido}propionyl)-4-cyclohexylpiperidine-4-carboxylate;
Ethyl 1-((S)-3-(4-chlorophenyl)-2-{3-[2-(1H-imidazol-4-yl)ethyl]ureido}propionyl)-4-cyclohexylpiperidine-4-carboxylate;
1-[2-(4-Cyclohexyl-4-propionylpiperidin-1-yl)-1-(4-methoxybenzyl)-2-oxoethyl]-3-[2-(1H-imidazol-4-yl)ethyl]urea;
1-[2-(4-Cyclohexyl-4-propionylpiperidin-1-yl)-1-(4-methoxybenzyl)-2-oxoethyl]-3-(1H-imidazol-4-ylmethyl)urea;
Ethyl 4-cyclohexyl-1-[(R)-2-{3-[2-(1H-imidazol-4-yl)ethyl]ureido}-3-(4-methoxyphenyl)propionyl]piperidine-4-carboxylate;
Ethyl 4-cyclopropylmethyl-1-[2-{3-[2-(1H-imidazol-4-yl)ethyl]ureido}-3-(4-methoxyphenyl)propionyl]piperidine-4-carboxylate;
Propyl 4-cyclohexyl-1-(2-{3-[2-(1H-imidazol-4-yl)ethyl]ureido}-3-phenylpropionyl)piper dine-4-carboxylate;
Ethyl 4-cyclopentyl-1-(2-{3-[2-(1H-imidazol-1-yl)ethyl]ureido}-3-phenylpropionyl)piperidine-4-carboxylate;
Ethyl 4-cyclopentyl-1-[2-{3-[2-(1H-imidazol-4-yl)ethyl]ureido}-3-(4-methoxyphenyl)propionyl]piperidine-4-carboxylate;
Ethyl 4-cyclohexyl-1-[(S)-2-{3-[2-(1H-imidazol-4-yl)ethyl]ureido}-3-(4-methoxyphenyl)propionyl]piperidine-4-carboxylate;
1-[(R)-2-(4-Butyryl-4-cyclohexylpiperidin-1-yl)-1-(4-methoxybenzyl)-2-oxoethyl]-3-[2-(1H-imidazol-4-yl)ethyl]urea;
1-[(R)-2-(4-Butyryl-4-cyclohexylpiperidin-1-yl)-1-(4-fluorobenzyl)-2-oxoethyl]-3-[2-(1H-imidazol-4-yl)ethyl]urea;
1-[(R)-1-Benzyl-2-(4-butyryl-4-cyclohexylpiperidin-1-yl)-2-oxoethyl]-3-[2-(1H-imidazol-4-yl)ethyl]urea;
1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea;
1-[(R)-2-(4-Butyryl-4-cyclohexylpiperidin-1-yl)-1-(4-chlorobenzyl)-2-oxoethyl]-3-[2-(1H-imidazol-4-yl)ethyl]urea;
Ethyl 4-cyclohexyl-1-((R)-3-(3,4-dichlorophenyl)-2-{3-[3-(1H-imidazol-4-yl)propyl]ureido}propionyl)piperidine-4-carboxylate;
Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate;
Ethyl 4-cyclohexyl-1-[(R)-2-{3-[2-(1H-imidazol-4-yl)ethyl]thioureido}-3-(4-methoxyphenyl)propionyl]piperidine-4-carboxylate;
1-[(R)-2-(4-Butyryl-4-cyclohexylpiperidin-1-yl)-1-(4-methoxybenzyl)-2-oxoethyl]-3-[2-(1H-imidazol-4-yl)ethyl]thiourea;
1-[(R)-2-(4-Cyclohexyl-4-propoxypiperidin-1-yl)-1-(4-methoxybenzyl)-2-oxoethyl]-3-[2-(1H-imidazol-4-yl)ethyl]thiourea;
1-[(R)-1-Benzyl-2-(4-cyclohexyl-4-propoxypiperidin-1-yl)-2-oxoethyl]-3-[2-(1H-imidazol-4-yl)ethyl]thiourea;
1-[(R)-1-Benzyl-2-(4-cyclohexyl-4-propoxypiperidin-1-yl)-2-oxoethyl]-3-[2-(1H-imidazol-4-yl)ethyl]urea;
Ethyl 4-cyclohexyl-1-((R)-3-(4-methoxyphenyl)-2-{3-[2-(3-methyl-3H-Imidazol-4-yl)ethyl]thioureido}propionyl)piperidine-4-carboxylate;
Ethyl 4-cyclohexyl-1-((R)-2-{3-[2-(3-methyl-3H-Imidazol-4-yl)ethyl]ureido}-3-phenylpropionyl)piperidine-4-carboxylate;
1-[(R)-2-(4-Cyclohexyl-4-propoxypiperidin-1-yl)-1-(4-methoxybenzyl)-2-oxoethyl]-3-[2-(3-methyl-3H-imidazol-4-yl)ethyl]urea;
Ethyl 1-((R)-3-(4-chlorophenyl)-2-{3-[2-(3-methyl-3H-imidazol-4-yl)ethyl]ureido}propionyl)-4-cyclohexylpiperidine-4-carboxylate;
Ethyl 4-cyclohexyl-1-((R)-3-(4-fluorophenyl)-2-{3-[2-(3-methyl-3H-imidazol-4-yl)ethyl]ureido}propionyl)piperidine-4-carboxylate;
Ethyl 4-cyclohexyl-1-((R)-3-(4-fluorophenyl)-2-{3-[2-(1H-imidazol-4-yl)ethyl]ureido}propionyl)piperidine-4-carboxylate;
Ethyl 4-cyclohexyl-1-((R)-3-(4-fluorophenyl)-2-{3-[2-(1H-imidazol-4-yl)ethyl]thioureido}propionyl)piperidine-4-carboxylate;
Ethyl 1-((R)-3-(4-chlorophenyl)-2-{3-[2-(1H-imidazol-4-yl)ethyl]thioureido}propionyl)-4-cyclohexylpiperidine-4-carboxylate;
Ethyl 1-((R)-3-(4-chlorophenyl)-2-{3-[2-(3-methyl-3H-imidazol-4-yl)ethyl]thioureido}propionyl)-4-cyclohexylpiperidine-4-carboxylate;
1-[(R)-2-(4-Cyclohexyl-4-propoxypiperidin-1-yl)-1-(4-fluorobenzyl)-2-oxoethyl]-3-[2-(1H-imidazol-4-yl)ethyl]urea;
1-[(R)-1-(4-Chlorobenzyl)-2-(4-cyclohexyl-4-propoxypiperidin-1-yl)-2-oxoethyl]-3-[2-(1H-imidazol-4-yl)ethyl]urea; and
respective salts and enantiomers thereof.

7. The compound according to claim 6, which is selected from the group consisting of:
1-[(S)-2-(4-Butyryl-4-phenylpiperidin-1-yl)-1-(4-methoxybenzyl)-2-oxoethyl]-3-[2-(1H-imidazol-4-yl)ethyl]urea;
1-[2-(4-Cyano-4-phenylpiperidin-1-yl)-1-(4-methoxybenzyl)-2-oxoethyl]-3-[2-(1H-imidazol-4-yl)ethyl]urea;
1-[2-(1H-Imidazol-4-yl)ethyl]-3-[1-(4-methoxybenzyl)-2-oxo-2-(4-phenylpiperidin-1-yl)ethyl]urea;
Ethyl 4-cyclohexyl-1-[2-{3-[2-(1H-imidazol-4-yl)ethyl]ureido}-3-(4-methoxyphenyl)-propionyl]piperidine-4-carboxylate;
Ethyl 1-[2-{3-[2-(1H-imidazol-4-yl)ethyl]ureido}-3-(4-methoxyphenyl)propionyl]piperidine-4-carboxylate;
1-[2-(1H-Imidazol-4-yl)ethyl]-3-{1-(4-methoxybenzyl)-2-[4-(2-methoxyphenyl)-piperidin-1-yl]-2-oxoethyl}urea;
1-[2-(3-Butoxy-3-phenylazetidin-1-yl)-1-(4-methoxybenzyl)-2-oxoethyl]-3-[2-(1H-imidazol-4-yl)ethyl]urea;
Methyl 4-cyclohexyl-1-[2-{3-[2-(1H-imidazol-4-yl)ethyl]ureido}-3-(4-methoxyphenyl)-propionyl]piperidine-4-carboxylamide;
1-[2-(3-Cyclohexanecarbonylazetidin-1-yl)-1-(4-methoxybenzyl)-2-oxoethyl]-3-[2-(1H-imidazol-4-yl)ethyl]urea;
Ethyl 4-cyclohexyl-1-[2-{3-ethyl-3-[2-(1H-imidazol-4-yl)ethyl]ureido}-3-(4-methoxyphenyl)propionyl]piperidine-4-carboxylate;

Ethyl 4-cyclohexyl-1-(2-{3-[2-(1H-imidazol-4-yl)ethyl]ureido}-3-phenylpropionyl)piperidine-4-carboxylate;
1-[2-(4-Butyryl-4-cyclohexylpiperidin-1-yl)-1-(4-methoxybenzyl)-2-oxoethyl]-3-[2-(3H-imidazol-4-yl)ethyl]urea;
1-[2-(4-Butoxy-4-cyclohexylpiperidin-1-yl)-1-(4-methoxybenzyl)-2-oxoethyl]-3-[2-(1H-imidazol-4-yl)ethyl]urea;
Ethyl 4-cyclohexyl-1-(2-{3-[2-(1H-imidazol-4-yl)ethyl]ureido}-2-phenylacetyl)piperidine-4-carboxylate;
Methyl 4-cyclohexyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-ethoxypiperidin-1-yl)-1-(4-methoxybenzyl)-2-oxoethyl]-3-[2-(1H-imidazol-4-yl)ethyl]urea;
1-[2-(4-Acetyl-4-cyclohexylpiperidin-1-yl)-1-(4-methoxybenzyl)-2-oxoethyl]-3-[2-(1H-imidazol-4-yl)ethyl]urea;
Methyl 4-cyclohexyl-1-(2-{3-[2-(1H-imidazol-4-yl)ethyl]ureido}-2-phenylacetyl)piperidine-4-carboxylate;
Ethyl 4-ethyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-propoxypiperidin-1-yl)-1-(4-methoxybenzyl)-2-oxoethyl]-3-[2-(1H-imidazol-4-yl)ethyl]urea;
1-[2-(1H-Imidazol-4-yl)ethyl]-3-{1-(4-methoxybenzyl)-2-[3-(2-methylcyclohexyl)-3-propoxyazetidin-1-yl]-2-oxoethyl}urea;
Propyl 4-cyclohexyl-1-[2-{3-[2-(1H-imidazol-4-yl)ethyl]ureido}-3-(4-methoxyphenyl)propionyl]piperidine-4-carboxylate;
1-[2-(1H-Imidazol-4-y)ethyl]-3-[1-(4-methoxybenzyl)-2-oxo-2-(3-pentyl-3-phenylazetidin-1-yl)ethyl]urea;
Ethyl 1-((R)-3-(4-chlorophenyl)-2-{3-[2-(1H-imidazol-4-yl)ethyl]ureido}propionyl) 4-cyclohexylpiperidine-4-carboxylate;
Ethyl 1-((S)-3-(4-chlorophenyl)-2-{3-[2-(1H-imidazol-4-yl)ethyl]ureido}propionyl)-4-cyclohexylpiperidine-4-carboxylate;
1-[2-(4-Cyclohexyl-4-propionylpiperidin-1-yl)-1-(4-methoxybenzyl)-2-oxoethyl]-3-[2-(1H-imidazol-4-yl)ethyl]urea;
1-[2-(4-Cyclohexyl-4-propionylpiperidin-1-yl)-1-(4-methoxybenzyl)-2-oxoethyl]-3-(1H-imidazol-4-ylmethyl)urea;
Ethyl 4-cyclohexyl-1-[(R)-2-{3-[2-(1H-imidazol-4-yl)ethyl]ureido}-3-(4-methoxyphenyl)propionyl]piperidine-4-carboxylate;
Ethyl 4-cyclopropylmethyl-1-[2-{3-[2-(1H-imidazol-4-yl)ethyl]ureido}-3-(4-methoxyphenyl)propionyl]piperidine-4-carboxylate;
Propyl 4-cyclohexyl-1-(2-{3-[2-(1H-imidazol-4-yl)ethyl]ureido}-3-phenylpropionyl)piperidine-4-carboxylate;
Ethyl 4-cyclopentyl-1-(2-{3-[2-(1H-imidazol-4-yl)ethyl]ureido}-3-phenylpropionyl)piperidine-4-carboxylate;
Ethyl 4-cyclopentyl-1-[2-{3-[2-(1H-imidazol-4-yl)ethyl]ureido}-3-(4-methoxyphenyl)propionyl]piperidine-4-carboxylate;
Ethyl 4-cyclohexyl-1-[(S)-2-{3-[2-(1H-imidazol-4-yl)ethyl]ureido}-3-(4-methoxyphenyl)propionyl]piperidine-4-carboxylate;
1-[(R)-2-(4-Butyryl-4-cyclohexylpiperidin-1-yl-1-(4-methoxybenzyl)-2-oxoethyl]-3-[2-(1H-imidazol-4-yl)ethyl]urea;
1-[(R)-2-(4-Butyryl-4-cyclohexylpiperidin-1-yl)-1-(4-fluorobenzyl)-2-oxoethyl]-3-[2-(1H-imidazol-4-yl)ethyl]urea;
1-[(R)-1-Benzyl-2-(4-butyryl-4-cyclohexylpiperidin-1-yl)-2-oxoethyl]-3-[2-(1H-imidazol-4-yl)ethyl]urea;
1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea;
1-[(R)-2-(4-Butyryl-4-cyclohexyl piperidin-1-yl)-1-(4-chlorobenzyl)-2-oxoethyl]-3-[2-(1H-imidazol-4-yl)ethyl]urea;
Ethyl 4-cyclohexyl-1-((R)-3-(3,4-dichlorophenyl)-2-{3-[3-(1H-imidazol-4-yl)propyl]ureido}propionyl)piperidine-4-carboxylate;
Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate;
Ethyl 4-cyclohexyl-1-[(R)-2-{3-[2-(1H-imidazol-4-yl)ethyl]thioureido}-3-(4-methoxyphenyl)propionyl]piperidine-4-carboxylate; and
respective salts and enantiomers thereof.

8. The compound according to claim 6, which is selected from the group consisting of:
Ethyl 4-cyclohexyl-1-[2-{3-[2-(1H-imidazol-4-yl)ethyl]ureido}-3-(4-methoxyphenyl)-propionyl]piperidine-4-carboxylate;
Ethyl 4-cyclohexyl-1-(2-{3-[2-(1H-imidazol-4-yl)ethyl]ureido}-3-phenylpropionyl)piperidine-4-carboxylate;
1-[2-(4-Butyryl-4-cyclohexylpiperidin-1-yl)-1-(4-methoxybenzyl)-2-oxoethyl]-3-[2-(3H-imidazol-4-yl)ethyl]urea;
1-[2-(4-Butoxy-4-cyclohexylpiperidin-1-yl)-1-(4-methoxybenzyl)-2-oxoethyl]-3-[2-(1H-imidazol-4-yl)ethyl]urea;
Methyl 4-cyclohexyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-ethoxypiperidin-1-yl)-1-(4-methoxybenzyl)-2-oxoethyl]-3-[2-(1H-imidazol-4-yl)ethyl]urea;
1-[2-(4-Acetyl-4-cyclohexylpiperidin-1-yl)-1-(4-methoxybenzyl)-2-oxoethyl]-3-[2-(1H-imidazol-4-yl)ethyl]urea;
Ethyl 4-ethyl-1-[2-{3-[2-(1H-imidazol-4-yl)ethyl]ureido}-3-(4-methoxyphenyl)propionyl]piperidine-4-carboxylate;
1-[2-(4-Cyclohexyl-4-propoxypiperidin-1-yl)-1-(4-methoxybenzyl)-2-oxoethyl]-3-[2-(1H-imidazol-4-yl)ethyl]urea;
Propyl 4-cyclohexyl-1-[2-{3-[2-(1H-imidazol-4-yl)ethyl]ureido}-3-(4-methoxyphenyl)propionyl]piperidine-4-carboxylate;
Ethyl 1-((R)-3-(4-chlorophenyl)-2-{3-[2-(1H-imidazol-4-yl)ethyl]ureido}propionyl)-4-cyclohexylpiperidine-4-carboxylate;
1-[2-(4-Cyclohexyl-4-propionylpiperidin-1-yl)-1-(4-methoxybenzyl)-2-oxoethyl]-3-[2-(1H-imidazol-4-yl)ethyl]urea;
1-[2-(4-Cyclohexyl-4-propionylpiperidin-1-yl)-1-(4-methoxybenzyl)-2-oxoethyl]-3-(1H-imidazol-4-ylmethyl)urea;
Ethyl 4-cyclohexyl-1-[(R)-2-{3-[2-(1H-imidazol-4-yl)ethyl]ureido}-3-(4-methoxyphenyl)propionyl]piperidine-4-carboxylate;
Ethyl 4-cyclopropylmethyl-1-[2-{3-[2-(1H-imidazol-4-yl)ethyl]ureido}-3-(4-methoxyphenyl)propionyl]piperidine-4-carboxylate;

Propyl 4-cyclohexyl-1-(2-{3-[2-(1H-imidazol-4-yl)ethyl]ureido}-3-phenylpropionyl)piperidine-4-carboxylate;

Ethyl 4-cyclopentyl-1-[2-{3-[2-(1H-imidazol-4-yl)ethyl]ureido}-3-(4-methoxyphenyl)propionyl]piperidine-4-carboxylate;

Ethyl 4-cyclohexyl-1-[(S)-2-{3-[2-(1H-imidazol-4-yl)ethyl]ureido}-3-(4-methoxyphenyl)propionyl]piperidine-4-carboxylate;

1-[(R)-2-(4-Butyryl-4-cyclohexylpiperidin-1-yl)-1-(4-methoxybenzyl)-2-oxoethyl]-3-[2-(1H-imidazol-4-yl)ethyl]urea;

1-[(R)-2-(4-Butyryl-4-cyclohexyl piperidin-1-yl)-1-(4-fluorobenzyl)-2-oxoethyl]-3-[2-(1H-imidazol-4-yl)ethyl]urea;

1-[(R)-1-Benzyl-2-(4-butyryl-4-cyclohexylpiperidin-1-yl)-2-oxoethyl]-3-[2-(1H-imidazol-4-yl)ethyl]urea;

1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea;

1-[(R)-2-(4-Butyryl-4-cyclohexylpiperidin-1-yl)-1-(4-methoxybenzyl)-2-oxoethyl]-3-[2-(1H-imidazol-4-yl)ethyl]urea;

1-[(R)-2-(4-Butyryl-4-cyclohexylpiperidin-1-yl)-1-(4-chlorobenzyl)-2-oxoethyl]-3-[2-(1H-imidazol-4-yl)ethyl]urea;

Ethyl 4-cyclohexyl-1-((R)-3-(3,4-dichlorophenyl)-2-{3-[3-(1H-imidazol-4-yl)propyl]ureido}propionyl)piperidine-4-carboxylate;

Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate;

Ethyl 4-cyclohexyl-1-[(R)-2-{3-[2-(1H-imidazol-4-yl)ethyl]thioureido}-3-(4-methoxyphenyl)propionyl]piperidine-4-carboxylate; and respective salts and enantiomers thereof.

9. The compound according to claim 6, which is selected from the group consisting of:

Ethyl 4-cyclohexyl-1-[2-{3-[2-(1H-imidazol-4-yl)ethyl]ureido}-3-(4-methoxyphenyl)-propionyl]piperidine-4-carboxylate;

Ethyl 4-cyclohexyl-1-(2-{3-[2-(1H-imidazol-4-yl)ethyl]ureido}-3-phenylpropionyl)piperidine-4-carboxylate;

1-[2-(4-Butyryl-4-cyclohexylpiperidin-1-yl)-1-(4-methoxybenzyl)-2-oxoethyl]-3-[2-(3H-imidazol-4-yl)ethyl]urea;

1-[2-(4-Butoxy-4-cyclohexyl piperidin-1-yl)-1-(4-methoxybenzyl)-2-oxoethyl]-3-[2-(1H-imidazol-4-yl)ethyl]urea;

Methyl 4-cyclohexyl-1-[2-{3-[2-(1H-imidazol-4-yl)ethyl]ureido}-3-(4-methoxyphenyl)propionyl]piperidine-4-carboxylate;

1-[2-(4-Cyclohexyl-4-ethoxypiperidin-1-yl)-1-(4-methoxybenzyl)-2-oxoethyl]-3-[2-(1H-imidazol-4-yl)ethyl]urea;

1-[2-(4-Acetyl-4-cyclohexylpiperidin-1-yl)-1-(4-methoxybenzyl)-2-oxoethyl]-3-[2-(1H-imidazol-4-yl)ethyl]urea;

1-[2-(4-Cyclohexyl-4-propoxypiperidin-1-yl)-1-(4-methoxybenzyl)-2-oxoethyl]-3-[2-(1H-imidazol-4-yl)ethyl]urea;

Propyl 4-cyclohexyl-1-[2-{3-[2-(1H-imidazol-4-yl)ethyl]ureido}-3-(4-methoxyphenyl)propionyl]piperidine-4-carboxylate;

Ethyl 1-((R)-3-(4-chlorophenyl)-2-{3-[2-(1H-imidazol-4-yl)ethyl]ureido}propionyl)-4-cyclohexylpiperidine-4-carboxylate;

1-[2-(4-Cyclohexyl-4-propionylpiperidin-1-yl)-1-(4-methoxybenzyl)-2-oxoethyl]-3-[2-(1H-imidazol-4-yl)ethyl]urea;

Ethyl 4-cyclohexyl-1-[(R)-2-{3-[2-(1H-imidazol-4-yl)ethyl]ureido}-3-(4-methoxyphenyl)propionyl]piperidine-4-carboxylate;

Propyl 4-cyclohexyl-1-(2-{3-[2-(1H-imidazol-4-yl)ethyl]ureido}-3-phenylpropionyl)piperidine-4-carboxylate;

Ethyl 4-cyclopentyl-1-[2-{3-[2-(1H-imidazol-4-yl)ethyl]ureido}-3-(4-methoxyphenyl)propionyl]piperidine-4-carboxylate;

Ethyl 4-cyclohexyl-1-[(S)-2-{3-[2-(1H-imidazol-4-yl)ethyl]ureido}-3-(4-methoxyphenyl)propionyl]piperidine-4-carboxylate;

1-[(R)-2-(4-Butyryl-4-cyclohexylpiperidin-1-yl)-1-(4-methoxybenzyl)-2-oxoethyl]-3-[2-(1H-imidazol-4-yl)ethyl]urea;

1-[(R)-2-(4-Butyryl-4-cyclohexylpiperidin-1-yl)-1-(4-fluorobenzyl)-2-oxoethyl]-3-[2-(1H-imidazol-4-yl)ethyl]urea;

1-[(R)-1-Benzyl-2-(4-butyryl-4-cyclohexylpiperidin-1-yl)-2-oxoethyl]-3-[2-(1H-imidazol-4-yl)ethyl]urea;

1-[(R)-2-(4-Butyryl-4-cyclohexylpiperidin-1-yl)-1-(4-methoxybenzyl)-2-oxoethyl]-3-[2-(3-methyl-3H-imidazol-4-yl)ethyl]urea;

1-[(R)-2-(4-Butyryl-4-cyclohexylpiperidin-1-yl)-1-(4-chlorobenzyl)-2-oxoethyl]-3-[2-(1H-imidazol-4-yl)ethyl]urea;

Ethyl 4-cyclohexyl-1-((R)-3-(4-methoxyphenyl)-2-(3-[2-(3-methyl-3H-imidazol-4-yl)ethyl]ureido)propionyl)piperidine-4-carboxylate;

Ethyl 4-cyclohexyl-1-[(R)-2-{3-[2-(1H-imidazol-4-yl)ethyl]thioureido}-3-(4-methoxyphenyl)propionyl]piperidine-4-carboxylate; and respective salts and enantiomers thereof.

10. The compound according to claim 6, which is selected from the group consisting of:

Ethyl 4-cyclohexyl-1-[2-{3-[2-(1H-imidazol-4-yl)ethyl]ureido}-3-(4-methoxyphenyl)-propionyl]piperidine-4-carboxylate;

Ethyl 4-cyclohexyl-1-(2-{3-[2-(1H-imidazol-4-yl)ethyl]ureido}-3-phenylpropionyl)piperidine-4-carboxylate;

1-[2-(4-Butyryl-4-cyclohexylpiperidin-1-yl)-1-(4-methoxybenzyl)-2-oxoethyl]-3-[2-(3H-imidazol-4-yl)ethyl]urea;

Methyl 4-cyclohexyl-1-[2-{3-[2-(1H-imidazol-4-yl)ethyl]ureido}-3-(4-methoxyphenyl)propionyl]piperidine-4-carboxylate;

1-[2-(4-Acetyl-4-cyclohexylpiperidin-1-yl)-1-(4-methoxybenzyl)-2-oxoethyl]-3-[2-(1H-imidazol-4-yl)ethyl]urea;

Propyl 4-cyclohexyl-1-[2-{3-[2-(1H-imidazol-4-yl)ethyl]ureido}-3-(4-methoxyphenyl)propionyl]piperidine-4-carboxylate;

Ethyl 1-((R)-3-(4-chlorophenyl)-2-{3-[2-(1H-imidazol-4-yl)ethyl]ureido}propionyl)-4-cyclohexylpiperidine-4-carboxylate;

1-[2-(4-Cyclohexyl-4-propionylpiperidin-1-yl)-1-(4-methoxybenzyl)-2-oxoethyl]-3-[2-(1H-imidazol-4-yl)ethyl]urea;

Ethyl 4-cyclohexyl-1-[(R)-2-{3-[2-(1H-imidazol-4-yl)ethyl]ureido}-3-(4-methoxyphenyl)propionyl]piperidine-4-carboxylate;

Propyl 4-cyclohexyl-1-(2-{3-[2-(1H-imidazol-4-yl)ethyl]ureido}-3-phenylpropionyl)piperidine-4-carboxylate;

1-[(R)-2-(4-Butyryl-4-cyclohexylpiperidin-1-yl)-1-(4-methoxybenzyl)-2-oxoethyl]-3-[2-(1H-imidazol-4-yl)ethyl]urea;

1-[(R)-2-(4-Butyryl-4-cyclohexylpiperidin-1-yl)-1-(4-fluorobenzyl)-2-oxoethyl]-3-[2-(1H-imidazol-4-yl)ethyl]urea;

1-[(R)-1-Benzyl-2-(4-butyryl-4-cyclohexylpiperidin-1-yl)-2-oxoethyl]-3-[2-(1H-imidazol-4-yl)ethyl]urea;

1-[(R)-2-(4-Butyryl-4-cyclohexylpiperidin-1-yl)-1-(4-chlorobenzyl)-2-oxoethyl]-3-[2-(1H-imidazol-4-yl)ethyl]urea;

Ethyl 4-cyclohexyl-1-((R)-3-(4-methoxyphenyl)-2-{3-[2-(3-methyl-3H-imidazol-4-yl)ethyl]ureido}propionyl)piperidine-4-carboxylate;

Ethyl 4-cyclohexyl-1-[(R)-2-{3-[2-(1H-imidazol-4-yl)ethyl]thioureido}-3-(4-methoxyphenyl)propionyl]piperidine-4-carboxylate; and respective salts and enantiomers thereof.

11. A method for treating:
a pigmentation disorder selected from the group consisting of vitiligo, albinism, a post-inflammatory hypopigmentation disorder and piebaldism;
the method comprising administering to a subject in need of such treatment a pharmaceutical composition comprising a compound according to claim 1 and an acceptable support or medium.

12. A pharmaceutical composition comprising, in a physiologically acceptable medium, at least one compound of formula (I) as defined in claim 1.

13. The composition according to claim 12, wherein the concentration of the compound of formula (I) is between 0.001% and 10% by weight relative to the total weight of the composition.

14. The composition according to claim 12, which is formulated for topical application and wherein the concentration of the compound of formula (I) is between 0.01% and 5% by weight relative to the total weight of the composition.

15. The compound of formula (I) according to claim 1, which is ethyl 4-cyclohexyl-1-[(R)-2-{3-[2-(1H-imidazol-4-yl)ethyl]ureido}-3-(4-methoxyphenyl)propionyl]piperidine-4-carboxylate or 1-[(R)-2-(4-butyryl-4-cyclohexylpiperidin-1-yl)-1-(4-methoxybenzyl)-2-oxoethyl]-3-[2-(1H-imidazol-4-yl)ethyl]urea.

16. The method according to claim 11, wherein the compound of formula (I) administered is ethyl 4-cyclohexyl-1-[(R)-2-{3-[2-(1H-imidazol-4-yl)ethyl]ureido}-3-(4-methoxyphenyl)propionyl]piperidine-4-carboxylate or 1-[(R)-2-(4-butyryl-4-cyclohexylpiperidin-1-yl)-1-(4-methoxybenzyl)-2-oxoethyl]-3-[2-(1H-imidazol-4-yl)ethyl]urea.

17. The method according to claim 11, for treating vitiligo.

18. The method according to claim 17, wherein the compound of formula (I) administered is ethyl 4-cyclohexyl-1-[(R)-2-{3-[2-(1H-imidazol-4-yl)ethyl]ureido}-3-(4-methoxyphenyl)propionyl]piperidine-4-carboxylate or 1-[(R)-2-(4-butyryl-4-cyclohexylpiperidin-1-yl)-1-(4-methoxybenzyl-2-oxoethyl]-3-[2-(1H-imidazol-4-yl)ethyl]urea.

19. The composition according to claim 12, wherein the compound of formula (I) is ethyl 4-cyclohexyl-1-[(R)-2-{3-[2-(1H-imidazol-4-yl)ethyl]ureido}-3-(4-methoxyphenyl)propionyl]piperidine-4-carboxylate or 1-[(R)-2-(4-butyryl-4-cyclohexylpiperidin-1-yl)-1-(4-methoxybenzyl-2-oxoethyl]-3-[2-(1H-imidazol-4-yl)ethyl]urea.

20. The composition according to claim 13, wherein the compound of formula (I) is ethyl 4-cyclohexyl-1-[(R)-2-{3-[2-(1H-imidazol-4-yl)ethyl]ureido}-3-(4-methoxyphenyl)propionyl]piperidine-4-carboxylate or 1-[(R)-2-(4-butyryl-4-cyclohexylpiperidin-1-yl)-1-(4-methoxybenzyl)-2-oxoethyl]-3-[2-(1H-imidazol-4-yl)ethyl]urea.

21. The composition according to claim 14, wherein the compound of formula (I) is ethyl 4-cyclohexyl-1-[(R)-2-{3-[2-(1H-imidazol-4-yl)ethyl]ureido}-3-(4-methoxyphenyl)propionyl]piperidine-4-carboxylate or 1-[(R)-2-(4-butyryl-4-cyclohexylpiperidin-1-yl)-1-(4-methoxybenzyl)-2-oxoethyl]-3-[2-(1H-imidazol-4-yl)ethyl]urea.

22. A method for activating a melanocortin receptor MC1-R in a cell, said method comprising contacting said cell with an MC1-R-activating amount of a compound of formula (I), or salt or enantiomer thereof, according to claim 1.

23. A method for activating a melanocortin receptor MC1-R in a cell, said method comprising contacting said cell with an MC1-R-activating amount of a compound of formula (I) or salt or enantiomer thereof, according to claim 2.

24. A method for activating a melanocortin receptor MC1-R in a cell, said method comprising contacting said cell with an MC1-R-activating amount of a compound of formula (I) or salt or enantiomer thereof, according to claim 3.

25. A method for activating a melanocortin receptor MC1-R in a cell, said method comprising contacting said cell with an MC1-R-activating amount of a compound of formula (I) or salt or enantiomer thereof, according to claim 4.

26. A method for activating a melanocortin receptor MC1-R in a cell, said method comprising contacting said cell with an MC1-R-activating amount of a compound of formula (I) or salt or enantiomer thereof, according to claim 5.

27. A method for activating a melanocortin receptor MC1-R in a cell, said method comprising contacting said cell with an MC1-R-activating amount of a compound or salt or enantiomer thereof, according to claim 6.

28. A method for activating a melanocortin receptor MC1-R in a cell, said method comprising contacting said cell with an MC1-R-activating amount of a compound or salt or enantiomer thereof, according to claim 7.

29. A method for activating a melanocortin receptor MC1-R in a cell, said method comprising contacting said cell with an MC1-R-activating amount of a compound or salt or enantiomer thereof, according to claim 8.

30. A method for activating a melanocortin receptor MC1-R in a cell, said method comprising contacting said cell with an MC1-R-activating amount of a compound or salt or enantiomer thereof, according to claim 9.

31. A method for activating a melanocortin receptor MC1-R in a cell, said method comprising contacting said cell with an MC1-R-activating amount of a compound or salt or enantiomer thereof, according to claim 10.

32. A method for activating a melanocortin receptor MC1-R in a cell, said method comprising contacting said cell with an MC1-R-activating amount of a compound of formula (I) or salt or enantiomer thereof, according to claim 15.

33. A method for treating:
a pigmentation disorder selected from the group consisting of vitiligo, albinism, a post-inflammatory hypopigmentation disorder and piebaldism;
the method comprising administering to a subject in need of such treatment a pharmaceutical composition comprising a compound according to claim 6 and an acceptable support or medium.

34. A pharmaceutical composition comprising, in a physiologically acceptable medium, at least one compound as defined in claim 6.

35. The composition according to claim 34, wherein the concentration of the compound is between 0.001% and 10% by weight relative to the total weight of the composition.

36. The composition according to claim 34, which is formulated for topical application and wherein the concentration of the compound is between 0.01% and 5% by weight relative to the total weight of the composition.

\* \* \* \* \*